United States Patent
Kolesnick et al.

(10) Patent No.: US 12,214,218 B2
(45) Date of Patent: Feb. 4, 2025

(54) PERFUSION MODULATED TUMOR DOSE SCULPTING WITH SINGLE DOSE RADIOTHERAPY

(71) Applicants: MEMORIAL SLOAN KETTERING CANCER CENTER, New York, NY (US); FUNDAçÃO D. ANNA DE SOMMER CHAMPALIMAUD E DR. CARLOS MONTEZ CHAMPALIMAUD, Lisbon (PT)

(72) Inventors: Richard Kolesnick, New York, NY (US); Zvi Fuks, New York, NY (US); Carlo Greco, Lisbon (PT)

(73) Assignees: MEMORIAL SLOAN KETTERING CANCER CENTER, New York, NY (US); FUNDAçÃO D. ANNA DE SOMMER CHAMPALIMAUD E DR. CARLOS MONTEZ CHAMPALIMAUD, Lisbon (PT)

( * ) Notice: Subject to any disclaimer, the term of this patent is extended or adjusted under 35 U.S.C. 154(b) by 255 days.

(21) Appl. No.: 17/631,152

(22) PCT Filed: Jul. 30, 2020

(86) PCT No.: PCT/PT2020/050027
§ 371 (c)(1),
(2) Date: Jan. 28, 2022

(87) PCT Pub. No.: WO2021/020979
PCT Pub. Date: Feb. 4, 2021

(65) Prior Publication Data
US 2022/0296926 A1   Sep. 22, 2022

Related U.S. Application Data

(60) Provisional application No. 62/883,074, filed on Aug. 5, 2019, provisional application No. 62/883,078, filed
(Continued)

(51) Int. Cl.
*A61N 5/10* (2006.01)
*A61K 41/00* (2020.01)

(52) U.S. Cl.
CPC ........ *A61N 5/1031* (2013.01); *A61K 41/0038* (2013.01); *A61N 2005/1087* (2013.01); *A61N 2005/1098* (2013.01)

(58) Field of Classification Search
CPC .......... A61N 5/1031; A61N 2005/1087; A61N 2005/1098; A61K 41/0038
See application file for complete search history.

(56) References Cited

U.S. PATENT DOCUMENTS

| | | |
|---|---|---|
| 2012/0197058 A1 | 8/2012 | Shukla et al. |
| 2013/0324784 A1 | 12/2013 | Fredriksson |

(Continued)

OTHER PUBLICATIONS

International Search Report and Written Opinion on PCT PCT/PT2020/050027 dated Nov. 13, 2020 (16 pages).

*Primary Examiner* — Kiho Kim
(74) *Attorney, Agent, or Firm* — Foley & Lardner LLP

(57) ABSTRACT

The present disclosure provides methods and systems for treating tumors with radiotherapy, wherein a first dose of radiation is administered to a first sub-volume of the tumor and a second dose of radiation is administered to a second sub-volume of the tumor.

20 Claims, 16 Drawing Sheets

Specification includes a Sequence Listing.

Related U.S. Application Data on Aug. 5, 2019, provisional application No. 62/880,797, filed on Jul. 31, 2019.

(56) References Cited

U.S. PATENT DOCUMENTS

| | | |
|---|---|---|
| 2016/0051841 A1 | 2/2016 | Nguyen |
| 2016/0144201 A1 | 5/2016 | Schulte |
| 2017/0056689 A1* | 3/2017 | D'Agostino ........... A61B 90/08 |

* cited by examiner

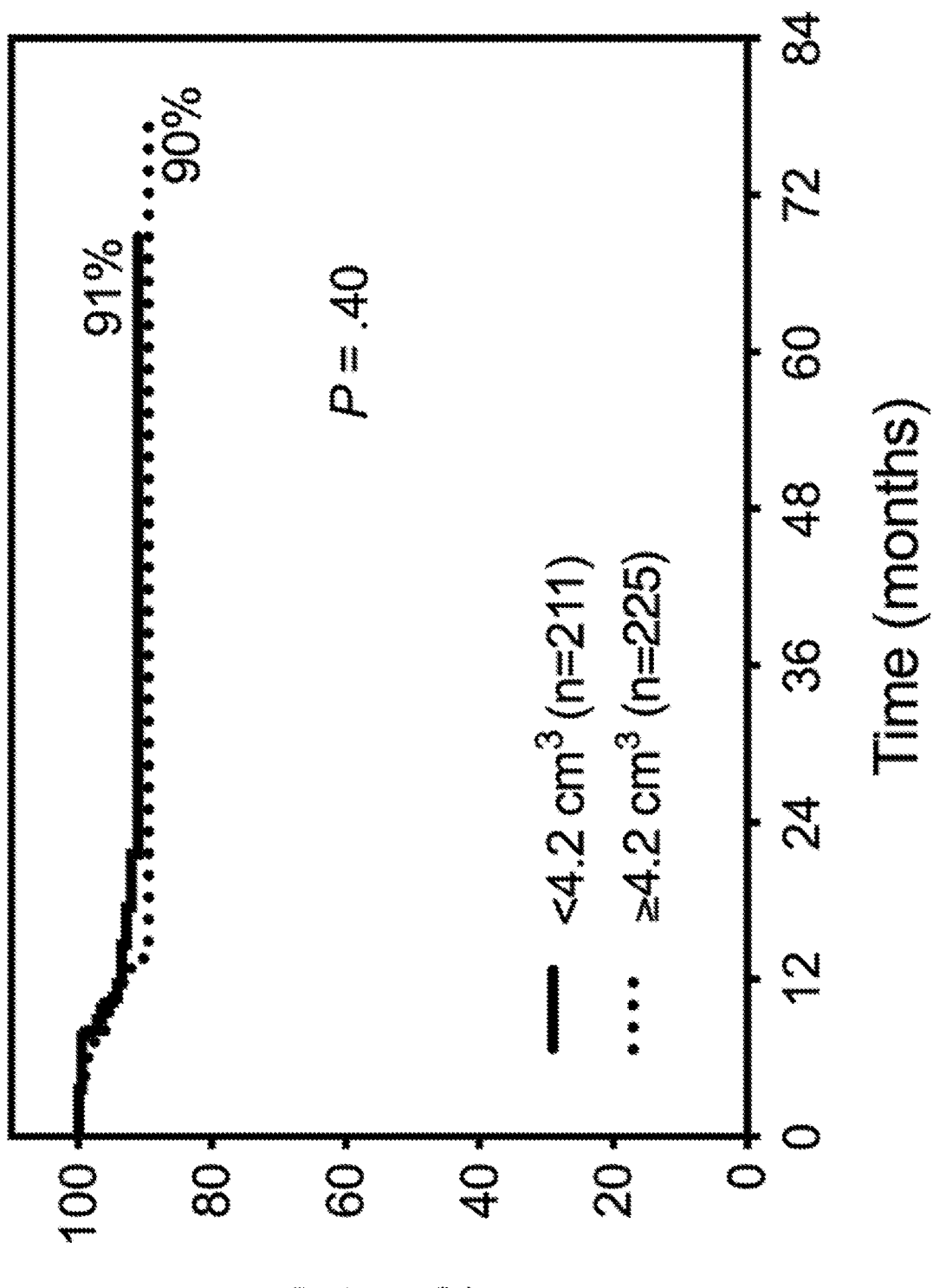

```
                        SEQUENCE LISTING

<160> NUMBER OF SEQ ID NOS: 10

<210> SEQ ID NO 1
<211> LENGTH: 214
<212> TYPE: PRT
<213> ORGANISM: Artificial Sequence
<220> FEATURE:
<223> OTHER INFORMATION: Ranibizumab Light Chain

<400> SEQUENCE: 1

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
```

```
<211> LENGTH: 231
<212> TYPE: PRT
<213> ORGANISM: Artificial Sequence
<220> FEATURE:
<223> OTHER INFORMATION: Ranibizumab Heavy Chain

<400> SEQUENCE: 2
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

```
<210> SEQ ID NO 3
<211> LENGTH: 11
<212> TYPE: PRT
<213> ORGANISM: Artificial Sequence
<220> FEATURE:
<223> OTHER INFORMATION: R84 VL CDR1

<400> SEQUENCE: 3
```

Arg Ala Ser Gln Ser Ile Ser Ser Tyr Leu Asn
1               5                   10

```
<210> SEQ ID NO 4
<211> LENGTH: 7
<212> TYPE: PRT
<213> ORGANISM: Artificial Sequence
<220> FEATURE:
<223> OTHER INFORMATION: R84 VL CDR2

<400> SEQUENCE: 4
```

Ala Ala Ser Ser Leu Gln Ser
1               5

```
<210> SEQ ID NO 5
<211> LENGTH: 9
<212> TYPE: PRT
<213> ORGANISM: Artificial Sequence
<220> FEATURE:
<223> OTHER INFORMATION: R84 VL CDR3

<400> SEQUENCE: 5

Gln Gln Ser Tyr Ser Thr Pro Leu Thr
1               5

<210> SEQ ID NO 6
<211> LENGTH: 5
<212> TYPE: PRT
<213> ORGANISM: Artificial Sequence
<220> FEATURE:
<223> OTHER INFORMATION: R84 VH CDR1

<400> SEQUENCE: 6

Ser Tyr Ala Ile Ser
1               5

<210> SEQ ID NO 7
<211> LENGTH: 16
<212> TYPE: PRT
<213> ORGANISM: Artificial Sequence
<220> FEATURE:
<223> OTHER INFORMATION: R84 VH CDR2

<400> SEQUENCE: 7

Gly Phe Asp Pro Glu Asp Gly Glu Thr Ile Tyr Ala Gln Lys Phe Gln
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: R84 VH CDR3

<400> SEQUENCE: 8

Gly Arg Ser Met Val Arg Gly Val Ile Ile Pro Phe Asn Gly Met Asp
1               5                   10                  15

<210> SEQ ID NO 9
<211> LENGTH: 107
<212> TYPE: PRT
<213> ORGANISM: Artificial Sequence
<220> FEATURE:
<223> OTHER INFORMATION: R84 light chain variable region

<400> SEQUENCE: 9

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95
```

```
Thr Phe Gly Gly Gly Thr Lys Val Glu Ile Lys
            100                 105

<210> SEQ ID NO 10
<211> LENGTH: 126
<212> TYPE: PRT
<213> ORGANISM: Artificial Sequence
<220> FEATURE:
<223> OTHER INFORMATION: R84 heavy chain variable region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
            100                 105                 110

Met Asp Val Trp Gly Gln Gly Thr Thr Val Thr Val Ser Ser
            115                 120                 125
```

PERFUSION MODULATED TUMOR DOSE SCULPTING WITH SINGLE DOSE RADIOTHERAPY

CROSS-REFERENCE TO RELATED APPLICATIONS

This application is a U.S. National Stage Application under 35 U.S.C. § 371 of International Patent Application No. PCT/PT2020/050027, filed on Jul. 30, 2020, which claims the benefit of U.S. Provisional Application No. 62/880,797, filed Jul. 31, 2019, U.S. Provisional Application No. 62/883,074, filed Aug. 5, 2019, and U.S. Provisional Application No. 62/883,078, filed Aug. 5, 2019, all of which are herein incorporated by reference in their entireties.

INCORPORATION BY REFERENCE OF SEQUENCE LISTING

The contents of the text file submitted electronically herewith are incorporated herein by reference in their entirety: A computer readable format copy of the Sequence Listing (filename: CERA_010_03WO_SeqList_ST25.TXT, date created: Jul. 27, 2020, file size: about 7.6 kilobytes).

FIELD

The present disclosure relates to methods of radiotherapy, for example in the treatment of solid tumors.

BACKGROUND

The past decade has brought about major advances in tumor radiotherapy. Success of conventional fractionated radiotherapy has been limited, curing only ~65% of patients treated with a curative intent. More recently, single dose radiotherapy (SDRT) has been used to treat human tumors, delivering single high doses of radiation (~24 Gy) to achieve local tumor cure rates of 90-95%. However, the anatomical proximity of a tumor to normal organs limits the implementation of SDRT in a high percentage of patients. Reduction of the whole tumor radiation dose delivered in SDRT to spare normal organs is associated with high frequencies of local tumor relapses.

BRIEF DESCRIPTION OF DRAWINGS

FIG. 5A-FIG. 5B illustrate actuarial local relapse free survival (LRFS) of oligometastatic (OM) tumors from the time of 24 Gy SDRT delivery. FIG. 5A show the effect of planning target volume (PTV) on LRFS dichotomized by the median PTV. FIG. 5B show the effect of lesion maximum standardized uptake value ($SUV_{Max}$) of 18F-fluorodeoxy-glucose positron emission topography (PET [$^{18}$F]FDG) on LRFS dichotomized by the median $SUV_{Max}$.

FIG. 6A show the effect of systemic therapy given prior to SDRT. FIG. 6B show the effect of systemic therapy given as adjuvant to SDRT.

FIG. 8A illustrates incidence of local failure for lesions grouped by the $PTV_{PMDS}$ penumbra dose. FIG. 8B illustrates incidence of local failure for lesions grouped by the combination of $PTV_{PMDS}$ penumbra dose and the percentage volume of the $PTV_{HD}$ carried to 24 Gy (V100) relative to the total volume of the PTV.

FIG. 9A shows an axial view of the dose distribution to the dominant $PTV_{HD}$ (24 Gy) and dose gradient in the intersection volume within the small bowel PRV (indicated by an arrow). FIG. 9B shows the axial (right) and sagittal (left) views of the dose distribution in the two PTV sub-volumes: the dominant $PTV_{HD}$ (indicated in each image by white right-ward facing arrows; 1.5 cm$^3$) is covered by the 24 Gy prescription dose and the conformal avoidance volume, $PTV_{PMDS}$ (indicated in each image by hatched left-ward facing arrows; 0.7 cm$^3$) is exposed to a steep dose gradient to fulfil dose/volume constraints for the small bowel ($D_{max}$=14 Gy). FIG. 9C shows dose-volume histograms for the $PTV_{HD}$, CTV, PTV, $PTV_{PMDS}$, small bowel, and small bowel PRV.

FIG. 10A illustrates the radiation dose-response of MCA/129 fibrosarcomas in mice treated with radiation alone. FIG. 10B illustrates the radiation dose-response of MCA/129 fibrosarcomas in mice treated with DC101 prior to radiation. FIG. 10C compares the fitted curves of radiation dose-response for these two groups.

SUMMARY

Figure 1:
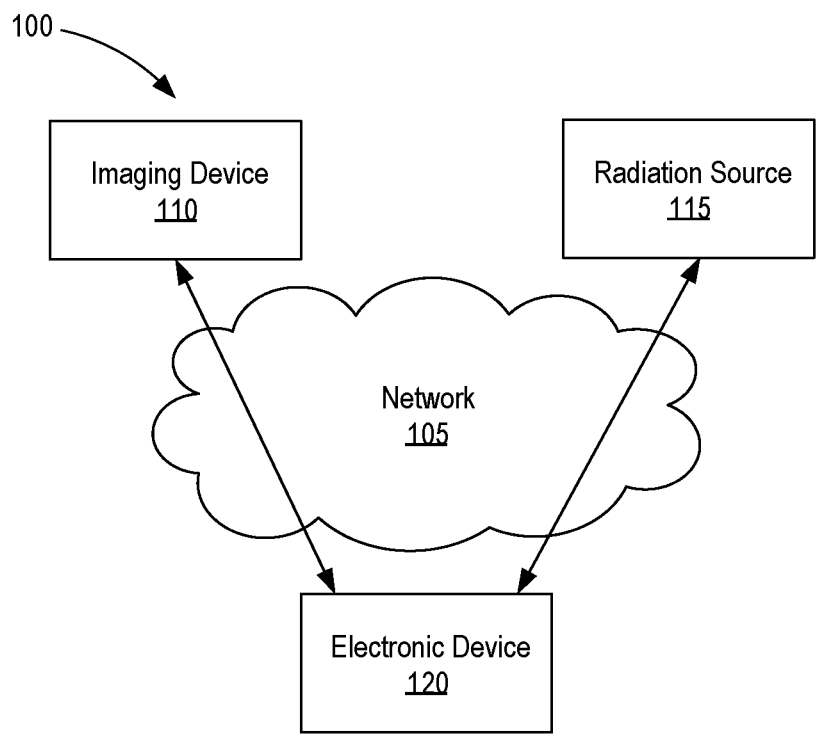
FIG. 1-FIG. 2 are schematic illustrations of at least a portion of a system for treating a tumor in a subject in need thereof, according to an embodiment.

There is a need in the art for methods of radiotherapy that enable delivery of single dose radiation therapy sufficient to ablate tumors while avoiding toxicities to nearby organs at risk (OAR).

In some embodiments, the present disclosure provides a method of treating a tumor in a subject in need thereof, said tumor comprising: a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$); wherein the method comprises delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$, and wherein the dose of radiation delivered to the $PTV_{PMDS}$ is insufficient to treat the tumor when delivered to the entirety of the $PTV_{TOTAL}$.

In some embodiments, the present disclosure provides a system for treating a tumor comprising: a) a radiation source; and b) an electronic device, the electronic device including at least a memory and a processor operatively coupled to the memory and configured to execute instructions stored on the memory, the processor configured to: i) define a total planning target volume ($PTV_{TOTAL}$) comprising the tumor's total volume, wherein said $PTV_{TOTAL}$ comprises a first planning target sub-volume ($PTV_{HD}$) and a second planning target sub-volume ($PTV_{PMDS}$); ii) define a radiotherapy treatment plan for said $PTV_{TOTAL}$; and iii) send, to the radiation source, a signal indicative of an instruction to deliver radiation doses to the $PTV_{TOTAL}$, wherein the dose of radiation delivered to the $PTV_{PMDS}$ is less the dose of radiation delivered to the $PTV_{HD}$; wherein the dose of radiation delivered to the $PTV_{PMDS}$ is insufficient to treat the tumor when delivered to the entirety of the $PTV_{TOTAL}$.

In some embodiments, the radiation source is selected from the group consisting of an x-ray emitter, an electron beam emitter, a proton beam emitter, and a linear accelerator. In some embodiments, the radiation source comprises a radioactive element selected from the group consisting of radioactive cesium, iridium, iodine, cobalt, and combinations thereof.

In some embodiments, the present disclosure provides a method of treating a tumor in a subject in need thereof comprising: defining, at a processor, a total planning target volume ($PTV_{TOTAL}$) of the tumor; dividing, at the processor, the $PTV_{TOTAL}$ of the tumor into at least a first planning target sub-volume ($PTV_{HD}$) and a second planning target sub-volume ($PTV_{PMDS}$); sending, from the processor and to a radiation source, a signal associated with a perfusion modulated dose sculpting (PMDS) radiotherapy plan; and delivering, from the radiation source, a dose of radiation to each of the $PTV_{HD}$ and the $PTV_{PMDS}$ based on the PMDS radiotherapy plan, wherein the dose of radiation covering 95% of the $PTV_{PMDS}$ ($PTV_{PMDS}$-D95) is lower than the dose of radiation covering 95% of the $PTV_{HD}$ ($PTV_{HD}$-D95) and wherein the $PTV_{PMDS}$-D95 is lower than the dose of radiation covering 95% of the total PTV ($PTV_{TOTAL}$-D95) required to treat the tumor.

In some embodiments, the present disclosure provides a method of defining a perfusion modulated dose sculpting (PMDS) radiotherapy plan for treating a tumor in a subject in need thereof, the method comprising: defining, at a processor, a total planning target volume ($PTV_{TOTAL}$) of the tumor; dividing, at the processor, the $PTV_{TOTAL}$ of the tumor into at least a first planning target sub-volume ($PTV_{HD}$) and a second planning target sub-volume ($PTV_{PMDS}$); defining a dose of radiation for each of the $PTV_{HD}$ and the $PTV_{PMDS}$; and defining the PMDS radiotherapy plan for treating the tumor wherein the dose of radiation covering 95% of the $PTV_{PMDS}$ ($PTV_{PMDS}$-D95) is lower than the dose of radiation covering 95% of the $PTV_{HD}$ ($PTV_{HD}$-D95) and wherein the $PTV_{PMDS}$-D95 is lower than the dose of radiation covering 95% of the total PTV ($PTV_{TOTAL}$-D95) required to treat the tumor.

In some embodiments of the methods and systems described herein, the $PTV_{HD}$ comprises at least 60% of the $PTV_{TOTAL}$. In some embodiments, the $PTV_{HD}$ comprises at least 60% of the tumor's total volume. In some embodiments, the $PTV_{PMDS}$ comprises 40% or less of the $PTV_{TOTAL}$. In some embodiments, the $PTV_{PMDS}$ comprises at least 5% of the $PTV_{TOTAL}$. In some embodiments, the $PTV_{PMDS}$ comprises at least 5% of the tumor's total volume. In some embodiments, the tumor is adjacent to a dose limiting organ at risk (OAR). In some embodiments, the OAR is a serial OAR.

In some embodiments of the methods and systems described herein, the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, or at least 26 Gy. In some embodiments, the dose of radiation delivered to the $PTV_{HD}$ is between about 22 Gy and about 25 Gy. In some embodiments, the dose of radiation delivered to the $PTV_{PMDS}$ is less than about 23 Gy. In some embodiments, the dose of radiation delivered to the $PTV_{PMDS}$ is between about 12 Gy and 23 Gy. In some embodiments, the dose of radiation delivered to the $PTV_{PMDS}$ is less than about 18 Gy. In some embodiments, the dose of radiation delivered to the $PTV_{PMDS}$ is between about 12 Gy and 18 Gy. In some embodiments, the dose of radiation delivered to the $PTV_{PMDS}$ is less than about 12 Gy. In some embodiments, the dose of radiation delivered to the $PTV_{PMDS}$ is at least 10% lower than the dose of radiation delivered to the $PTV_{HD}$. In some embodiments, the dose of radiation delivered to the $PTV_{PMDS}$ is between about 10% and about 50% lower than the dose of radiation delivered to the $PTV_{HD}$. In some embodiments, the dose of radiation delivered to the $PTV_{PMDS}$ is at least 50% lower than the dose of radiation delivered to the $PTV_{HD}$.

In some embodiments of the methods and systems described herein, the dose of radiation delivered to 99% of the $PTV_{PMDS}$ ($PTV_{PMDS}$-D99) is at least 20% lower than the dose of radiation delivered to 99% of the $PTV_{HD}$ ($PTV_{HD}$-D99). In some embodiments, the dose of radiation delivered to 95% of the $PTV_{PMDS}$ ($PTV_{PMDS}$-D95) is at least 20% lower than the dose of radiation delivered to 95% of the $PTV_{HD}$ ($PTV_{HD}$-D95).

In some embodiments, the methods described herein reduce incidence of local relapse compared to fractionated radiotherapy methods. In some embodiments, the dose of radiation delivered to the $PTV_{HD}$ and the dose of radiation delivered to the $PTV_{PMDS}$ are delivered in the same treatment session. In some embodiments, the dose of radiation delivered to the $PTV_{HD}$ and the dose of radiation delivered to the $PTV_{PMDS}$ are delivered simultaneously in the same treatment session.

DETAILED DESCRIPTION

Overview

The present disclosure provides methods of radiotherapy that enable the delivery of single dose radiation therapy (SDRT) sufficient to ablate tumors while avoiding toxicities to nearby organs at risk (OAR). The present methods utilize localized dose-sculpting of a tumor portion proximal to an adjacent OAR, generating a distal penumbra isodose surface that complies with the OAR radiation tolerance. The disclosed methods compensate for the attenuated local control probability of the dose sculpted tumor portion based on a novel bystander mechanism of SDRT-induced ischemic stress leading to tumor cell death. The methods thus render a novel approach to SDRT tumor ablation when adjusted to meet dose-limiting specificities of adjacent OARs.

Definitions

As used in this specification and the appended claims, the singular forms "a," "an" and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10% or less in either direction (greater than or less than) of the stated reference value unless otherwise stated or otherwise evident from the context (e.g., except where such number would exceed 100% of a possible value or fall below 0% of a possible value).

The term "sample" refers to a biological composition (e.g., a cell or a portion of a tissue) that is subjected to analysis and/or modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein. In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

"Administration" refers herein to introducing an agent, composition, or radiation into a subject.

"Treating" as used herein refers to delivering an agent, composition, or radiation to a subject to affect a physiologic outcome.

As used herein, the term "effective amount" refers to the minimum amount of an agent, composition, or radiation required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

"Synergistic effect," "synergy," or "synergistic tumor response" means the effect of two or more active agents (including radiation), administered as described herein is greater than the sum of the effects each agent would produce had the agents been administered alone.

"Additive effect," "stackable effect," or "combined effect" means that the effect of two or more active agents (including radiation), administered as described herein would be greater than the effect of administering only one of the agents. In some cases, additive effects can be unexpected, particularly when the two or more active agents operate under the same or similar mechanisms.

The terms "tumor" or "neoplasm" refer to an abnormal mass of tissue that results from aberrant cell proliferation or persistence. Tumors may be benign (non-cancerous) or malignant (cancerous).

"Gross tumor volume" or "GTV" refers to the gross volume of the clinical or subclinical malignant growth. The GTV can comprise the primary tumor, the regional lymph nodes, and/or the distant metastases according to the clinical situation. The GTV is delineated based on anatomic (e.g. CT or MRI) or functional (e.g. PET with various tracers) imaging modalities. Unless otherwise stated, the GTV refers to the gross volume of a tumor comprising a continuous mass of cells, and metastases are considered separate tumors for which separate GTV calculations would be required.

"Clinical target volume" (CTV, also referred to as "Target Volume") is a volume of tissue that contains a demonstrable GTV and/or subclinical malignant disease with a certain probability of occurrence considered relevant for therapy. There is no general consensus on what probability is considered relevant for therapy, but typically a probability of occult disease higher than about 5% to about 10% is assumed to require treatment.

"Planning target volume" or "PTV" refers to a conceptual volume comprising the total CTV and the surrounding margin. The PTV is a geometrical concept to shape absorbed-dose distributions to ensure that the prescribed absorbed dose will actually be delivered to all parts of the CTV with a clinically acceptable probability, despite geometrical uncertainties such as organ motion and setup variations. It surrounds the representation of the CTV with a margin such that the planned absorbed dose is delivered to the CTV. This margin takes into account both the internal and the setup uncertainties. The setup margin accounts specifically for uncertainties in patient positioning and alignment of the therapeutic beams during the treatment planning, and through all treatment sessions. Recommendations have been published on how to calculate margins to delineate PTVs (See e.g., vanHerk, Errors and margins in radiotherapy. *Semin Radiat Oncol* 2004; 14:52-64).

"Planning target sub-volume" or "$PTV_{SV}$" refers to a portion of the PTV that is less than the total of the PTV. A single PTV can be divided into multiple sub-volumes, e.g., $PTV_{SV1}$, $PTV_{SV2}$, $PTV_{SV3}$, each of which can be prescribed a different absorbed radiation dose. In some embodiments, sub-volumes are referred to herein as $PTV_{HD}$, e.g., a first planning target sub-volume, and $PTV_{PMDS}$, e.g., a second planning target sub-volume. In some embodiments, the $PTV_{HD}$ and the $PTV_{PMDS}$ can form and/or comprise a total planning target volume, total PTV, and/or $PTV_{TOTAL}$.

"Organs at risk" or "OAR" are critical normal structures or tissues which, if exposed to radiation, could suffer significant morbidity and thus might influence the treatment planning and/or the absorbed-dose prescription. In principle, all non-target tissues could be considered organs at risk. However, delineation of normal tissues and structures as OARs will typically depend on the location of the CTV and/or the prescribed radiation dose. Recent recommendations have been published regarding normal tissue radiation tolerance (See e.g., Bentzen et al., Quantitative analyses of normal tissue effects in the clinic (QUANTEC): an introduction to the scientific issues. *Int J Radiat Oncol Biol Phys* 2010; 76:S3-9; and Benedict et al.: Stereotactic body radiation therapy: The report of TG101, Medical Physics, Vol. 37, No. 8, August 2010). In some embodiments, the tissues listed in Tables 1A and 1B are organs at risk for the purposes of this disclosure.

Various points in the disclosure of the invention describe the presence of an adjacent OAR. "Adjacent" as used herein, refers to an OAR or other tissue that is sufficiently close to a tumor, such that radiation treatment of the tumor would result in radiation exposure for the OAR or tissue (e.g., the penumbra of the radiation dose delivered to the tumor would overlap with a least a portion of the OAR). Persons having skill in the art will recognize that the term "adjacent" encompasses OARs that are in actual contact, or even slightly separated from tumors. Depending on the positions and shapes of the tumor and OAR, the term adjacent may also encompass OARs that are substantially separated from the tumor, but which are nonetheless at risk of radiation exposure during the radiation treatment of the tumor.

"Dose-limiting organ at risk" or "dose limiting OAR" refers to an organ or tissue that has a radiation threshold for a single radiation exposure that is lower than the cumulative absorbed-dose prescription for the treatment of a tumor. In some embodiments, the dose limiting OAR is a serial organ (e.g., those shown in Table 1A) or a parallel organ (e.g., those shown in Table 1).

"Planning organ at risk volume" or "PRV" refers to a volume comprising the OAR volume and the surrounding margins. In this way, the PRV and is analogous to the PTV. Because of uncertainties and variations in the position of the OAR during treatment, margins may be added to the OARs in order to avoid serious complications resulting from normal tissue exposure to radiation. Calculation of OAR margin will depend on the structure and nature of the OAR.

"Radiation absorbed dose" or "absorbed dose" or "rad" is the amount of energy that radioactive sources (with any type of ionizing radiation) deposit in materials (e.g., water, tissue, air) through which they pass. An absorbed dose of 1 rad means that 1 gram of material has absorbed 100 ergs of energy as a result of exposure to radiation. The related international system unit for the absorbed dose is the gray (Gy). 1 Gy is equivalent to an absorbed dose of 100 rad or 1 Joule/kilogram. (See the United States Nuclear Regulatory Commission (USNRC)—Measuring Radiation, available at the USNRC website).

"Dose equivalent" or "effective dose" refers to the amount of radiation absorbed and the medical effects of that type of radiation. Units for dose equivalent are the roentgen equivalent man (rem) and sievert (Sv), where 100 rem is equivalent to 1 Sv. The dose equivalent is calculated as the product of the absorbed dose (rad or gray) in tissue multiplied by a quality factor to obtain a quantity that expresses the biological damage (rem or Sv) to an exposed individual on a common scale for all ionizing radiation. (See Title 10, Section 20.1004, of the Code of Federal Regulations (10 CFR 20.1004), "Units of Radiation Dose"). The dose equivalent measurement is used because some types of radiation are more biologically damaging internally than other types. For example, the dose equivalent for beta and gamma radiation is the same as the absorbed dose, while the dose equivalent for alpha and neutron radiation is greater than the absorbed dose because these types of radiation are more damaging to the human body. (See the United States Nuclear Regulatory Commission (USNRC)—Measuring Radiation, available at the USNRC website).

The term "dose tolerance limit" refers to a specified radiation dose, fractionation, and volume, with an associated estimated risk of developing a complication of a specified endpoint within a specified follow-up time (Asbell et al. Introduction and clinical overview of the DVH risk map. Semin Radiat Oncol 2016; 26:89-96). A "dose tolerance limit" may also be referred to as "normal tissue complication probabilities" or "NTCP".

The term "dose-volume relationship" refers to the dose tolerance limit of a particular radiotherapy treatment determined across volumes of tumor exposure. (Asbell et al. Introduction and clinical overview of the DVH risk map. Semin Radiat Oncol 2016; 26:89-96). The term "dose-volume constraints" refers to the tolerance of a particular organ to radiation exposure and depends on the dose-volume relationship (i.e., depends on the dose of radiation employed as well as the volume of the tissue that is exposed).

"Bystander effect" refers to the ability of cells affected by irradiation to convey manifestations of damage to other cells—i.e., an irradiated cell can send out a signal and induce a response in a cell that was not directly hit by radiation or was exposed to a lower dose of radiation. (See Ray and Stick, Chapter 32—Radiation and Health Effects, Handbook of Toxicology of Chemical Warfare Agents ($2^{nd}$ Edition), 2015, p. 431-446 and Tomita, Mechanisms and biological importance of photon-induced bystander responses: do they have an impact on low-dose radiation responses, Journal of Radiation Research (2015) 56: 205-219).

"Radiation penumbra" or "penumbra" as used herein refers to the region at the periphery of the radiation beam wherein the radiation dose falls off sharply.

Radiation Therapy and Organs at Risk (OAR)

Oncological radiation therapy (also referred to herein as radiotherapy or radiation therapy) is used clinically to control, eliminate, or ablate cancerous growths (e.g., malignant tumors). Radiation therapy comprises administration of ionizing radiation such as high energy photons (e.g., x-rays or gamma rays), proton or neutron particles, or the like to tumors in order to induce tumor cell death through cellular DNA damage.

An ideal radiotherapy treatment delivers a dose of radiation to the tumor that is sufficient to induce tumor cell death and eliminate the tumor, while minimizing the radiation exposure of the surrounding normal tissue. Determination of appropriate radiotherapy parameters for delivering a selected radiation dose is a complex task involving the optimization of the angles and orientation of multiple radiation beams, tumor type, size, and shape, and the anatomical location of the tumor.

In particular, radiation dose is often limited by the radiation tolerance of the tissues and structures surrounding the tumor. Normal organs and tissues differ in their respective tolerance to radiation. "Serial normal organs", including tissues of the central nervous system (e.g., the spinal cord and brainstem), large nerve trunks, mucosa-lined organs (e.g., pulmonary bronchi and gastrointestinal organs) and the bladder, display type-specific intolerance to a single dose of radiation exposure within the range of 12-18 Gy, even if no more than a point volume is exposed (e.g., $\leq 0.035$ cm$^3$, See Benedict, 2010). In some embodiments, serial organs include those shown in Table 1A.

Other critical normal organs, termed "parallel organs", exhibit relative tolerance towards single radiation doses, including the parenchyma of the lung, liver and kidney. Threshold radiation doses for multiple organs are provided in Table 1A and Table 1B below, excerpted from Benedict et al., Stereotactic body radiation therapy: The report of AAPM Task Group 101. Med. Phys. 37(8), August 2010. In some embodiments, parallel organs include those shown in Table 1B.

In some embodiments, methods are provided herein for single-dose radiation treatment of tumors that are adjacent to a dose limiting organ at risk. In some embodiments, the dose limiting organ at risk is a serial organ. In some embodiments, the serial organ is an organ or tissue shown in Table 1A. In some embodiments, the dose limiting organ at risk is a parallel organ. In some embodiments, the parallel organ is an organ or tissue shown in Table 1B.

TABLE 1A

Summary of suggested dose constraints for various serial tissues

| Serial tissue | Max critical volume above threshold | One fraction | | Three fractions | |
|---|---|---|---|---|---|
| | | Threshold dose (Gy) | Max point dose (Gy)$^a$ | Threshold dose (Gy) | Max point dose (Gy)$^a$ |
| Optic pathway | <0.2 cc | 8 | 10 | 15.3 (5.1 Gy/fx) | 17.4 (5.8 Gy/fx) |
| Cochlea | | | 9 | | 17.1 (5.7 Gy/fx) |
| Brainstem (not medulla) | <0.5 cc | 10 | 15 | 18 (6 Gy/fx) | 23.1 (7.7 Gy/fx) |
| Spinal cord | <0.35 cc | 10 | 14 | 18 (6 Gy/fx) | 21.9 (7.3 Gy/fx) |
| Spinal cord and medulla | <1.2 cc | 7 | | 12.3 (4.1 Gy/fx) | |
| Spinal cord sub volume (5-6 mm above and below level treated per Ryu) | <10% of sub volume | 10 | 14 | 18 (6 Gy/fx) | 21.9 (7.3 Gy/fx) |
| Cauda equina | <5 cc | 14 | 16 | 21.9 (7.3 Gy/fx) | 24 (8 Gy/fx) |
| Sacral plexus | <5 cc | 14.4 | 16 | 22.5 (7.5 Gy/fx) | 24 (8 Gy/fx) |
| Esophagus$^b$ | <5 cc | 11.9 | 15.4 | 17.7 (5.9 Gy/fx) | 25.2 (8.4 Gy/fx) |
| Brachial plexus | <3 cc | 14 | 17.5 | 20.4 (6.8 Gy/fx) | 24 (8 Gy/fx) |
| Heart/pericardium | <15 cc | 16 | 22 | 24 (8 Gy/fx) | 30 (10 Gy/fx) |
| Great vessels | <10 cc | 31 | 37 | 39 (13 Gy/fx) | 45 (15 Gy/fx) |
| Trachea and large bronchus$^b$ | <4 cc | 10.5 | 20.2 | 15 (5 Gy/fx) | 30 (10 Gy/fx) |
| Bronchus-smaller airways | <0.5 cc | 12.4 | 13.3 | 18.9 (6.3 Gy/fx) | 23.1 (7.7 Gy/fx) |
| Rib | <1 cc | 22 | 30 | 28.8 (9.6 Gy/fx) | 36.9 (12.3 Gy/fx) |
| | <30 cc | | | 30.0 (10.0 Gy/fx) | |
| Skin | <10 cc | 23 | 26 | 30 (10 Gy/fx) | 33 (11 Gy/fx) |
| Stomach | <10 cc | 11.2 | 12.4 | 16.5 (5.5 Gy/fx) | 22.2 (7.4 Gy/fx) |
| Duodenum$^b$ | <5 cc | 11.2 | 12.4 | 16.5 (5.5 Gy/fx) | 22.2 (7.4 Gy/fx) |
| | <10 cc | 9 | | 11.4 (3.8 Gy/fx) | |
| Jejunum/ileum$^b$ | <5 cc | 11.9 | 15.4 | 17.7 (5.9 Gy/fx) | 25.2 (8.4 Gy/fx) |
| Colon$^b$ | <20 cc | 14.3 | 18.4 | 24 (8 Gy/fx) | 28.2 (9.4 Gy/fx) |
| Rectum$^b$ | <20 cc | 14.3 | 18.4 | 24 (8 Gy/fx) | 28.2 (9.4 Gy/fx) |
| Bladder wall | <15 cc | 11.4 | 18.4 | 16.8 (5.6 Gy/fx) | 28.2 (9.4 Gy/fx) |
| Penile bulb | <3 cc | 14 | 34 | 21.9 (7.3 Gy/fx) | 42 (14 Gy/fx) |
| Femoral heads (right and left) | <10 cc | 14 | | 21.9 (7.3 Gy/fx) | |
| Renal hilum/ vascular trunk | <2/3 volume | 10.6 | 18.6 (6.2 Gy/fx) | | |

| | Five fractions | | |
|---|---|---|---|
| Serial tissue | Threshold dose (Gy) | Max point dose (Gy)$^a$ | End point (Grade3) |
| Optic pathway | 23 (4.6 Gy/fx) | 25 (5 Gy/fx) | Neuritis |
| Cochlea | | 25 (5 Gy/fx) | Hearing loss |
| Brainstem (not medulla) | 23 (4.6 Gy/fx) | 31 (6.2 Gy/fx) | Cranial neuropathy |
| Spinal cord | 23 (4.6 Gy/fx) | 30 (6 Gy/fx) | Myelitis |
| Spinal cord and medulla | 14.5 (2.9 Gy/fx) | | Myelitis |
| Spinal cord sub volume (5-6 mm above and below level treated per Ryu) | 23 (4.6 Gy/fx) | 30 (6 Gy/fx) | Myelitis |
| Cauda equina | 30 (6 Gy/fx) | 32 (6.4 Gy/fx) | Neuritis |
| Sacral plexus | 30 (6 Gy/fx) | 32 (6.4 Gy/fx) | Neuropathy |
| Esophagus$^b$ | 19.5 (3.9 Gy/fx) | 35 (7 Gy/fx) | Stenosis/fistula |
| Brachial plexus | 27 (5.4 Gy/fx) | 30.5 (6.1 Gy/fx) | Neuropathy |
| Heart/pericardium | 32 (6.4 Gy/fx) | 38 (7.6 Gy/fx) | Pericarditis |
| Great vessels | 47 (9.4 Gy/fx) | 53 (10.6 Gy/fx) | Aneurysm |
| Trachea and large bronchus$^b$ | 16.5 (3.3 Gy/fx) | 40 (8 Gy/fx) | Stenosis/fistula |

TABLE 1A-continued

Summary of suggested dose constraints for various serial tissues

| | | | |
|---|---|---|---|
| Bronchus-smaller airways | 21 (4.2 Gy/fx) | 33 (6.6 Gy/fx) | Stenosis with atelectasis |
| Rib | 35 (7 Gy/fx) | 43 (8.6 Gy/fx) | Pain or fracture |
| Skin | 36.5 (7.3 Gy/fx) | 39.5 (7.9 Gy/fx) | Ulceration |
| Stomach | 18 (3.6 Gy/fx) | 32 (6.4 Gy/fx) | Ulceration/fistula |
| Duodenum[b] | 18 (3.6 Gy/fx) 12.5 (2.5 Gy/fx) | 32 (6.4 Gy/fx) | Ulceration |
| Jejunum/ileum[b] | 19.5 (3.9 Gy/fx) | 35 (7 Gy/fx) | Enteritis/obstruction |
| Colon[b] | 25 (5 Gy/fx) | 38 (7.6 Gy/fx) | Colitis/fistula |
| Rectum[b] | 25 (5 Gy/fx) | 38 (7.6 Gy/fx) | Proctitis/fistula |
| Bladder wall | 18.3 (3.65 Gy/fx) | 38 (7.6 Gy/fx) | Cystitis/fistula |
| Penile bulb | 30 (6 Gy/fx) | 50 (10 Gy/fx) | Impotence |
| Femoral heads (right and left) | 30 (6 Gy/fx) | | Necrosis |
| Renal hilum/vascular trunk | 23 (4.6 Gy/fx) | | Malignant Hypertension |

[a]"Point" defined as 0.035 cc or less.
[b]Avoid circumferential irradiation.

TABLE 1B

Summary of suggested dose constraints for various parallel tissues

| Parallel tissue | Minimum critical volume below threshold | One fraction | | Three fractions | | Five fractions | | End point (Grade3) |
|---|---|---|---|---|---|---|---|---|
| | | Threshold dose (Gy) | Max point dose (Gy)[a] | Threshold dose (Gy) | Max point dose (Gy)[a] | Threshold dose (Gy) | Max point dose (Gy)[a] | |
| Lung (right and left) | 1500 cc | 7 | NA-Parallel tissue | 11.6 (2.9 Gy/fx) | NA-Parallel tissue | 12.5 (2.5 Gy/fx) | NA-Parallel tissue | Basic lung function |
| Lung (right and left) | 1000 cc | 7.4 | NA-Parallel tissue | 12.4 (3.1 Gy/fx) | NA-Parallel tissue | 13.5 (2.7 Gy/fx) | NA-Parallel tissue | Pneumonitis |
| Liver | 700 cc | 9.1 | NA-Parallel tissue | 19.2 (4.8 Gy/fx) | NA-Parallel tissue | 21 (4.2 Gy/fx) | NA-Parallel tissue | Basic liver function |
| Renal cortex (right and left) | 200 cc | 8.4 | NA-Parallel tissue | 16 (4 Gy/fx) | NA-Parallel tissue | 17.5 (3.5 Gy/fx) | NA-Parallel tissue | Basic renal function |

Conventional Radiation Treatment

The first step in planning a radiation treatment is the accurate definition of the Clinical Target Volume (CTV) and the Planning Target Volume(s) (PTV(s)). Conventional radiotherapy defines the CTV in relation to bony or other detectable tissue landmarks. Multiple beams are delivered from different pre-planned directions to create a central region of high dose distribution. This method is simple and quick, but is imprecise and mandates wide normal tissue safety margins to avoid inadvertent tumor missing by radiation treatment, thereby resulting in the irradiation of significant volumes of adjacent normal tissues.

Typically, conventional radiation treatment utilizes low, non-tumor ablative, doses of radiation (1.8-2.5 Gy) delivered daily to eventually render a cumulative ablative dose. This approach is termed "fractionated radiotherapy", described in further detail below. At these doses, normal tissues repair radiation damage more efficiently than tumor cells. However, significant volumes of normal tissues were frequently included in the treatment fields, and the build-up of the fractionated radiation was associated with significant toxicity of the surrounding normal tissue. Conventional radiotherapy therefore did not allow for sufficient dose escalation to tumor-ablative levels because of the risk of significant collateral toxicity of the surrounding normal tissue.

Image-Guided Radiation Therapy and Conformal Radiotherapy

One notable avenue for reducing radiation exposure to non-tumor tissues is the use of image-guided radiation therapy. Recent technical innovations have led to the emergence of computer-guided precision treatment techniques that enable the confined delivery of ablative radiation doses to tumors, while reducing to minimum normal tissue exposure to toxic radiation levels. For example, the introduction of tween machines that combine linear accelerators and CT scanners provide improved on-line imaging of tumors and the surrounding normal structures, dramatically improving treatment accuracy. The introduction of multi-leaf collimation technology enables shaping of radiation fields to conform to the outline of the tumor in 3D, in a process referred to as "conformal radiotherapy." 3D conformal radiotherapy improves the spatial distribution of the dose and optimizes the avoidance of normal structures, thereby reducing toxicity and morbidity (See Dearnaley et al., Comparison of radiation side-effects of conformal and conventional radiotherapy in prostate cancer: a randomized trial. Lancet 1999; 353(9149): 267-72).

Reduced morbidity associated with these more precise treatment options enables the use of escalating radiation doses, thus improving treatment outcomes. However, the increase in toxicity risks associated with high-dose radiation has limited the use of early versions of 3D conformal radiotherapy to clinical settings that do not involve risk of surrounding OAR exposure to radiation.

Another approach used to maximize tumor ablative potentials while minimizing damage to OARs is the use of intensity modulated radiotherapy (IMRT). The IMRT technique employs dynamic multi-leaf collimation to modulate the beam intensity across the exposed tumor. This allows a practitioner to deliver or "paint" different pre-planned doses of radiation to different parts of the PTV. The goal of IMRT has been to generate dose homogeneity within the tumor with superior conformality compared to conventional 3D conformal radiotherapy. This process is referred to as "dose sculpting" and enables delivery of targeted radiation to the tumor while mitigating exposure of the surrounding OARs to radiation.

Dose Fractionation

Classical fractionated radiotherapy delivers daily radiation doses of between about 1.8 Gy and about 2.5 Gy over the course of several weeks. Thus, depending on the tumor type being treated, classical fractionated radiotherapy protocols may require 20, 30, 40, 50, 60 or more individual doses of radiation to be administered in order to achieve a cumulative biologically equivalent ablative dose.

The biologic basis for classical dose fractionation was predicated on early discoveries that although a single radiation dose of 1.8-2.5 Gy lacks curative potential, it nonetheless induces extensive DNA damage, including potentially lethal DNA double-strand breaks (DSBs) (Foray N, Radiation-induced DNA double-strand breaks and the radiosensitivity of human cells: a closer look. *Biochimie*. 1997; 79 (9-10):567-575). Repair of these DSBs determines post-radiation cellular viability. Radioresistant tumors repair damage faithfully and remain viable, while radiosensitive tumors have DNA repair defects leading to unrepaired or misrepaired DSBs and promoting genomic instability, lethal chromosomal aberrations, and cell death. (Rothkamm, Misrepair of radiation-induced DNA double-strand breaks and its relevance for tumorigenesis and cancer treatment. *Int J Oncol*. 2002; 21(2):433-440).

Thus, the classic theory fractionated radiation-mediated tumor cure posits that outcomes depend solely on the fidelity of tumor cell autonomous repair of DNA damage. This theory underlies the preeminent rule of radiotherapy—that DNA in the cell nucleus is the critical target of radiation and that DSBs are the critical radiation-induced lesions mediating tumor lethality, such that tumor cure requires every single tumor cell be exposed to an ablative dose of radiation. (See e.g., Little, Cellular radiation effects and the bystander response, Mutation Research (2006) 597:113-118 and ICRU Report 83).

Although classical fractionation therapy partially mitigates the risk of OAR toxicity, it nonetheless frequently results in collateral toxicity before a tumoricidal dose is reached, restricting the overall local tumor cure rate to 65% (See Leibel et al., The biological basis for conformal three-dimensional radiation therapy. *Int J Radiat Oncol Biol Phys*. 1991; 21(3):805-811).

Technological breakthroughs enabling dynamic high precision tumor targeting yielded effective exclusion of normal tissues from treatment fields, promoting safe delivery of daily doses exceeding 1.8-2.5 dose range/fraction. This approach, termed "hypofractionated radiotherapy" reduces the number of treatment fractions by increasing the dose administered in each fraction to generate an iso-cure probability rendered by classical fractionation, provided that the dose/fraction does not exceed 10 Gy/fraction (Guerrero M, Li X A. Extending the linear-quadratic model for large fraction doses pertinent to stereotactic radiotherapy. Phys Med Biol. 2004; 49:4825-35). Hypofractionation employing <10 Gy/fraction is termed "Stereotactic Body Radiotherapy" or "SBRT". Hypofractionation employing >10 Gy/fraction is termed "Stereotactic Ablative Radiotherapy" or "SABR". When clinically feasible, 3×18-20 Gy SABR provides high rates of tumor ablation (Folkert M R, and Timmerman R D).

Single Dose Radiation Therapy

"Single dose radiation therapy" or "SDRT" refers to a radiation therapy protocol in which a single high dose exposure is prescribed to ablate a tumor during a single clinical visit. SDRT demonstrates high local cancer cure rates after tumor exposure to a single high dose of ≥24 Gy, delivery of which is made possible by the intensity modulation and image guidance technologies described above. Phase I-II studies with SDRT report a steep tumor dose response curve, with a plateau of 92%-97% toxicity-free tumor ablation at 5 years achieved by 24-40 Gy SDRT (Gandhidasan et al. Single Fraction Stereotactic Ablative Body Radiotherapy for Oligometastasis: Outcomes from 132 Consecutive Patients. *Clin Oncol (R Coll Radiol)*. 2018; 30(3):178-84; Greco et al. Predictors of local control after single-dose stereotactic image-guided intensity-modulated radiotherapy for extracranial metastases. *Int J Radiat Oncol Biol Phys*. 2011; 79(4):1151-7; Meyer et al. A Phase I Dose-Escalation Trial of Single-Fraction Stereotactic Radiation Therapy for Liver Metastases. *Ann Surg Oncol*. 2016; 23(1):218-24; Yamada et al. High-dose, single-fraction image-guided intensity-modulated radiotherapy for metastatic spinal lesions. *Int J Radiat Oncol Biol Phys*. 2008; 71(2):484-90), regardless of tumor size, type, or organ in which the tumor is targeted (See Greco et al., Phenotype-Oriented Ablation of Oligometastatic Cancer with Single Dose Radiation Therapy. Int J Radiation Oncol Biol Phys, 2019).

However, in 24% of lesions, application of SDRT was not feasible because of tumor adherence or proximity to a serial OAR, rendering a potential unacceptable risk of severe OAR toxicity (Greco et al. 2019, supra). In these instances, an established non-toxic SBRT schedule, such as 3 doses of 9 Gy (3×9 Gy) is frequently used instead. However, the 3×9 Gy SBRT yields a 5-year tumor ablation in only 38% of lesions. (Greco et al. 2019, supra).

Perfusion Modulated Dose Sculpting (PMDS) Radiotherapy

In some embodiments, the present disclosure teaches "Perfusion Modulated Dose Sculpting radiotherapy" or "PMDS radiotherapy". The present disclosure leverages the present inventor's discovery that SDRT operates a unique mechanism of tumor cure, which fundamentally differs from the classical tumor cell-autonomous mechanism driving fractionated radiotherapy. The present inventors discovered that, beginning at a threshold of 12 Gy, SDRT employs a dual tumor target model, triggering both DSB DNA breaks in tumor cells, as well as an acute endothelial acid sphingomyelinase (ASMase)-mediated ischemia/reperfusion (I/R) response in the tumor stroma. In some embodiments, ASMase-induced I/R attenuates repair of tumor cell DNA DSBs, rendering synthetic tumor lethality (Bodo et al. Single-dose radiotherapy disables tumor cell homologous recombination via ischemia/reperfusion injury. *J Clin Invest*. 2019; 129(2):786-801).

The present inventors thus discovered that the ASMase-mediated I/R injury is an effector of the SDRT response, and the intensity of microvascular dysfunction is the rate-limiting variable regulating tumor clonogen lethality—a discovery that overturned conventional precepts that had dominated the past fifty years of radiation-based therapies. This new understanding of radiation-based tumor therapies was further supported by clinical studies demonstrating that human tumors treated with ablative 24 Gy SDRT induce the acute I/R response, while tumors treated with 3×9 Gy hypofractionated SBRT failed to induce this response and did not result in tumor cure.

Data provided herein further indicates that, in some embodiments, ASMase-mediated ischemic stress can be induced by high radiation doses directed at only a portion of the PTV through a radiosensitization effect. In some embodiments, the term "bystander effect" or "bystander radiosensitization" refers to the radiosensitization of the $PTV_{PMDS}$ sub-volume triggered by ASMase/hypoxia induced in the $PTV_{HD}$ sub-volume exposed to a high radiation dose (e.g., 24 Gy).

Without wishing to be bound by any one theory, the present inventors believe that the bystander radiosensitization of the $PTV_{PMDS}$ (the PTV receiving a lower radiation dosage) is effected by an ASMase/hypoxia induced by the high dose (e.g., 24 Gy-exposed) $PTV_{HD}$. Although the ASMase/hypoxia is induced in only a portion of the PTV (i.e., the $PTV_{HD}$), the $PTV_{HD}$ ASMase/hypoxia unexpectedly signals bystander radiosensitization of the low-dose, low ASMase/hypoxia-producing $PTV_{PMDS}$, but not of the OAR, yielding an iso-$PTV_{HD}$ tumor ablation in the $PTV_{PMDS}$, while sparing the OAR. Without wishing to be bound by theory, it is thought that the ASMase/hypoxia dissipates through the tumor interstitial space to render radiosensitization and tumor cell lethality in another portion of the tumor planned to undergo dose sculpting to a low, potentially non-curing dose level. This model is consistent with the unique pathophysiologic structure of tumor blood supply, constituting an interconnected tumor-confined network of neo-angiogenic microvessels, with SDRT-activated ASMase/hypoxia communicating freely throughout the unified interstitial space of the $PTV_{HD}$ and the $PTV_{PMDS}$, rendering a dynamic equilibrium of hypoxia throughout the tumor volume.

The present methods exploit this bystander radiosensitization effect, wherein radiation-induced, ASMase-mediated ischemic stress in one portion of the tumor radiosensitizes another portion of the tumor to overcome the limitations of SDRT implementation due to OAR risk toxicity thresholds. The presently disclosed methods thus provide effective treatments for tumors with adjacent OARs that had previously been considered untreatable. These methods are referred to herein as "Perfusion Modulated Dose Sculpting" methods or "PMDS".

In principle, PMDS tumor dose sculpting defies a basic rule of classical radiotherapy, which requires that every single tumor cell be directly exposed to a tumoricidal radiation dose, and which teaches that dose reduction is the dominant cause of local tumor recurrences. The $PTV_{PMDS}$ dose sculpting is planned to generate a dose fall-off at the penumbra encountering the OAR to a distal iso-dose surface that accommodates the dose/volume constraints of the OAR.

In some embodiments, the inventors discovered that despite the dose reduction, relapse free survival was achieved when at least 60% of the total PTV was exposed to the high dose radiation. The studies reported here show that when the high radiation (e.g., 24 Gy) treated $PTV_{HD}$ volume constituted ≥60% of the combined $PTV_{HD}+PTV_{PMDS}$ (whole tumor PTV), dose sculpting to any level, even as low as ≤12 Gy, yielded non-toxic tumor ablation at a rate equivalent to that observed in tumors not requiring SDRT-PMDS. These data provide compelling support for the bystander radiosensitization hypothesis, and serve as a guideline for future safe and effective use of SDRT-PMDS therapy.

Radiosensitizing Agents, Including Acid Sphingomyelinase (ASMase)/Ceramide Activating Agents In some embodiments, the methods described herein comprise delivering radiation to a subject in need thereof after or simultaneously with the administration of radiosensitizing agent. In some embodiments, the radiosensitizing agent is an ASMase/Ceramide (ASM/Cer) activating agent.

Single dose radiotherapy (SDRT) has proven successful in treating cancers previously considered radioresistant. While the exact mechanism of SDRT response has not been completely characterized, it is known that the endothelial cell ASMase/ceramide pathway plays a significant role in mediating this response. Radiation induces rapid endothelial cell ASMase activation, and radiation-induced apoptosis is ASMase dependent, as endothelium of mice lacking ASMase is resistant to apoptosis. Furthermore, the defect in apoptosis is rescued by addition of exogenous ceramide.

Previous studies have shown that serum ASMase activity increases in a dose dependent manner following irradiation. Significant differences in serum ASMase activity elevation at 24 hours post-radiation were observed when 15, 27, and 40 Gy were applied, but no significant changes occurred after 9 Gy. Importantly, the SDRT-induced serum ASMase activity increased linearly over the range of 15 to 40 Gy and correlated closely to complete response, suggesting that serum ASMase could be used a potential biomarker of ASMase/ceramide pathway activity in clinical SDRT scenarios. Further, tumors exhibiting a complete or partial response to SDRT demonstrated higher fold changes in ASMase activity, directly linking radiation responsiveness to ASMase/ceramide pathway activation. Accordingly, increase of ASMase activity as much as feasible without inducing toxicity in the treated subject emerges as a goal of treatment optimization. (See U.S. 2017-0333413). Thus, in some embodiments, pharmacological interventions to increase ASMase activity, such as administration of ASM/Cer activating agents prior to or concurrent with radiation treatment will further enhance responses to SDRT.

Thus, in some embodiments, the methods described herein comprise delivering an ASM/Cer activating agent to a subject in need thereof prior to or simultaneously with the administration of radiation. In some embodiments, the administration of the ASM/Cer activating agent further sensitizes the tumor to radiation. In some embodiments, the administration of the ASM/Cer activating agent reduces the volume of the tumor required to receive the $PTV_{HD}$. In some embodiments, the administration of the ASM/Cer activating agent reduces the dose of radiation delivered to the $PTV_{HD}$ and/or the $PTV_{PMDS}$.

Herein, an "ASM/Cer activating agent" refers to an agent that is capable of increasing the activity or expression of ASMase and/or increasing the level of ceramide present in a cell. In some embodiments, ASMase activity is assessed by measuring ASMase activity, or deducing ASMase activity by measuring a surrogate, such as one or more pro-apoptotic ceramides. ASMase activity can be assessed by dynamic intravoxel incoherent motion (IVIM)-based diffusion-weighted magnetic resonance imaging (DW-MRI). Suitable pro-apoptotic ceramides include C16:0 ceramide and C18:0 ceramide.

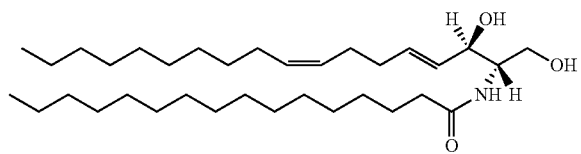

C16:0 Ceramide (CAS Number 24696-26-2)

-continued

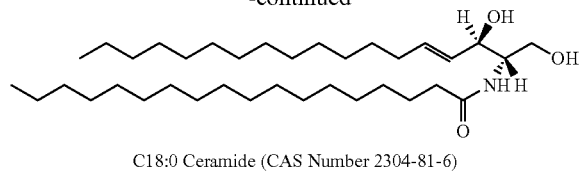

C18:0 Ceramide (CAS Number 2304-81-6)

In some embodiments, the radiosensitizing agent (e.g., the ASM/Cer activating agent) is or has been administered about 0 to 48 hours, 0 to 24 hours, 0 to 12 hours, 0 to 10 hours, 0 to 5 hours, about 0 to 4 hours, about 0 to 3 hours, about 0 to 2 hours, about 0 to 1 hours, about 0 to 1 hour, 0.5 to 48 hours, 0.5 to 24 hours, 0.5 to 12 hours, 0.5 to 10 hours, 0.5 to 5 hours, about 0.5 to 4 hours, about 0.5 to 3 hours, about 0.5 to 2 hours, about 0.5 to 1.5 hours, about 0.5 to 1 hour, 1 to 5 hours, about 1 to 4 hours, about 1 to 3 hours, about 1 to 2 hours, about 1 to 1.5 hour, 1.5 to 5 hours, about 1.5 to 4 hours, about 1.5 to 3 hours, about 1.5 to 2 hours, 2 to 5 hours, about 2 to 4 hours, about 2 to 3 hours, about 3 to 5 hours, about 3 to 4 hours, about 4 to 5 hours, about 10 to 48 hours, about 10 to 24 hours, about 10 to 12 hours, about 12 to 48 hours, about 12 to 24 hours, or about 24 to 48 hours before delivery of radiation. In some embodiments, the ASM/Cer activating agent is or has been administered no more than about 2 hours before delivery of radiation. In some embodiments, the ASM/Cer activating agent is or has been administered no more than about 1.5 hours before delivery of radiation. In some embodiments, the ASM/Cer activating agent is or has been administered no more than about 1 hour before delivery of radiation. In some embodiments, the ASM/Cer activating agent is or has been administered within a half-hour before delivery of radiation.

In some embodiments, the ASM/Cer activating agent is selected from the group consisting of: a vector comprising a polynucleotide encoding an ASMase protein, an anti-angiogenic agent, a composition comprising ceramide, and a recombinant ASMase protein.

The effective amount of a radiosensitizing agent (e.g., the ASM/Cer activating agent) administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

In some embodiments, the radiosensitizing agent (e.g., the ASM/Cer activating agent) is administered by injection, irrigation, inhalation, consumption, electro-osmosis, hemodialysis, iontophoresis, and other methods known in the art. In some embodiments, the administration route is local or systemic. In some embodiments administration route is intraarterial, intracranial, intradermal, intraduodenal, intramammary, intrameningeal, intraperitoneal, intrathecal, intratumoral, intravenous, intravitreal, ophthalmic, parenteral, spinal, subcutaneous, ureteral, urethral, vaginal, or intrauterine.

ASMase Vectors

In some embodiments, the ASM/Cer activating agent is a vector comprising a polynucleotide encoding the ASMase protein. Vectors can be nucleic acid vectors or non-nucleic acid vectors.

The term "nucleic acid vector" is used herein to refer to a nucleic acid molecule capable transferring or transporting another nucleic acid molecule. The transferred nucleic acid is generally linked to, e.g., inserted into, the vector nucleic acid molecule. A nucleic acid vector may include sequences that direct autonomous replication in a cell, or may include sequences sufficient to allow integration into host cell DNA. Nucleic acid vectors include, without limitation, replicons, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and viruses. In order to express the ASMase protein in a cell, an expression cassette encoding the ASMase protein can be inserted into appropriate nucleic acid vector. The term "expression cassette" as used herein refers to genetic sequences within a nucleic acid vector which can express a protein. In some embodiments, the cassette has its 3' and 5' ends adapted for ready insertion into a nucleic acid vector, e.g., it has restriction endonuclease sites at each end. In some embodiments, the cassette can be removed and inserted into a plasmid or viral vector as a single unit.

In some embodiments, the nucleic acid vector comprising a polynucleotide encoding the ASMase protein is a plasmid. Numerous suitable plasmid vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the cell targeted for ASMase expression. Depending on the cell type, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544). In some embodiments, cells targeted by the plasmid or other vector are tumor cells or tumor endothelial cells.

In some embodiments, the nucleic acid vector comprising the polynucleotide encoding the ASMase protein is a viral vector. Suitable viral vectors include, but are not limited to, viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al, PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al, Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Examples of vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells.

In some embodiments, the viral vector is a non-integrating viral vector, including but not limited to, an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus.

In some embodiments, the polynucleotide sequence encoding ASMase is operably linked to a control element, e.g., a transcriptional control element, such as a promoter. "Control elements" refer those non-translated regions of the nucleic acid vector (e.g., origin of replication, selection cassettes, promoters, enhancers, translation initiation signals (Shine Dalgarno sequence or Kozak sequence), introns, a polyadenylation sequence, 5' and 3' untranslated regions) which interact with host cellular proteins to carry out transcription and translation. The term "promoter" as used herein refers to a recognition site of a polynucleotide (DNA or RNA) to which an RNA polymerase binds. An RNA polymerase initiates and transcribes polynucleotides operably linked to the promoter. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1α) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, the human ROSA 26 locus (Irions et al., *Nature Biotechnology* 25, 1477-1482 (2007)), a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter, and mouse metallothionein-1.

In some embodiments, the polynucleotide sequence encoding the ASMase protein is operably linked to a constitutive promoter such that the ASMase protein is constitutively and/or ubiquitously expressed. In some embodiments, the polynucleotide sequence encoding the ASMase protein is operably linked to an inducible promoter such that the ASMase protein is conditionally expressed. As used herein, "conditional expression" may refer to any type of conditional expression including, but not limited to, inducible expression; repressible expression; expression in cells or tissues having a particular physiological, biological, or disease state (e.g., cell type or tissue specific expression) etc. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

In some embodiments, the polynucleotide sequence encoding the ASMase protein is operably linked to a cell-specific promoter such that the ASMase protein is expressed in a particular cell type or tissue. In some embodiments, the cell-specific promoter is an endothelial cell-specific promoter. Endothelial cell-specific promoters include, but are not limited to, endoglin promoter, the fms-like tyrosine kinase-1 (Flt-1) promoter, the intercellular adhesion molecule-2 (ICAM-2) promoter, the von Willebrand factor (vWF) promoter, the tyrosine kinase with immunoglobulin and epidermal growth factor homology domains (TIE) promoter, the kinase-like domain receptor (KDR) promoter, the cadherin 5 (CDH5) promoter, the P-selectin promoter, the preproendothelin-1 (PPE-1) promoter, the platelet endothelial cell adhesion molecule-1 (PECAM-1) promoter, the VE-cadherin (VECD) promoter, or modified or synthetic versions thereof (See e.g., Dai et al., J Virol. 2004 June; 78(12): 6209-6221). In some embodiments, the promoter is the modified PPE-1 promoter, PPE1-3X.

In some embodiments, the control element comprises one or more enhancer sequences that drive expression of the ASMase protein in angiogenic cells. Non-limiting examples of suitable enhancer sequences include hypoxia-inducible factor-1α (HIF-1α) binding motifs or MEF2 binding motifs.

In some embodiments, the polynucleotide encoding the ASMase protein further comprises a transcription termination signal. Elements directing the efficient termination and polyadenylation of the heterologous nucleic acid transcripts increases heterologous gene expression. Transcription termination signals are generally found downstream of the polyadenylation sequence. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. In some embodiments, the poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art. In some embodiments, the polynucleotide encoding the ASMase protein further comprises a sequence encoding a signal peptide (e.g., for nuclear localization, nucleolar localization, mitochondrial localization, endoplasmic reticulum (ER) localization).

In some embodiments, the vector comprising the polynucleotide encoding the ASMase protein is a non-nucleic acid vector. Non-nucleic acid vectors refer to non-nucleic acid delivery vehicles suitable for delivering the ASMase-encoding polynucleotide into a cell. Exemplary non-nucleic acid vectors include nanoparticles (e.g. lipid nanoparticles), exosomes, liposomes, and lipoplexes. In such embodiments, the polynucleotide encoding the ASMase protein can be an mRNA polynucleotide.

In some embodiments, the vector comprising the polynucleotide encoding the ASMase protein is an adenoviral vector, wherein the ASMase-encoding polynucleotide is operably linked to a control element comprising the PPE1-3× promoter and the HIF-1αenhancer (See US Patent Application Publication No. 20180015183).

In some embodiments, the ASM/Cer activating agent is an mRNA encoding an ASMase protein. Methods producing mRNAs for in vivo administration are known in the art, including those disclosed in (U.S. Pat. No. 10,519,189).

Anti-Angiogenic Agents

Angiogenesis is the process whereby new blood vessels are formed from the pre-existing ones and is a hallmark of tumor development and metastasis. During tumorigenesis, as cancer cells rapidly proliferate, tumors expand beyond the support capacity of the existing vasculature, leading to hypoxia, depletion of nutrients and accumulation of metabolic wastes. Tumor cells in turn adapt to these conditions by upregulating pro-angiogenic factors, such as vascular endothelial growth factor (VEGF), basic fibroblast growth factor (bFGF), and platelet-derived endothelial growth factor (PDGF). These factors cause activation of endothelial cells, promoting the growth of new blood vessels. Since tumors require a vascular supply to grow, the inhibition of tumor growth by anti-angiogenic drugs has long been identified as an important target for research and approach to treatment and has spurred the development of several anti-angiogenic agents (AAA). In some embodiments, anti-angiogenic agents have also been shown to have specific roles in ASMase signaling, derepressing ASMase pathways (e.g., as described in U.S. Pat. No. 10,413,533).

Angiogenesis inhibitors are classified into either direct inhibitors that target endothelial cells in the growing vasculature or indirect inhibitors that prevent the expression or block the activity of angiogenesis inducers from other tumor stromal cells.

In some embodiments, radiosensitizing agent and/or the ASM/Cer activating agent is an anti-angiogenic agent (AAA, also referred to as angiogenesis inhibitors). Exemplary anti-angiogenic agent includes, but are not limited to, ADH-1, Anginex (betapep-25), Axitinib (Inlyta®), AZD4547, Bevacizumab (Avastin®), Bortezomib, Brivanib, anti-BV8 antibodies, Cabozantinib (Cometriq®), Cediranib, Celecoxib, (AZD-2171 or Recentin), Cilengitide, Dasatinib, Dacinostat, Dovitinib, DX-2400, Everolimus (Afinitor®), Gossypol, JNJ-28312141, Lenalidomide (Revlimid®), Lenvatinib mesylate (Lenvima®), Nintedanib, NVP-AUY922, Pazopanib (Votrient®), PI-88, Ponatinib (Iclusig), Ramucirumab (Cyramza®), Regorafenib (Stivarga®), Repertaxin, Sorafenib (Nexavar®), Sunitinib (Sutent®), SU6668 (Oratinib), Thalidomide (Synovir, Thalomid®), Tipifarnib, Vatalanib, Vandetanib (Caprelsa®), Volociximab, Ziv-aflibercept (Zaltrap®), Zoledronic acid. (See e.g., El-Kenawi & El-Remessy, Br J Pharmacol. 2013 October; 170(4): 712-729; and "Angiogenesis Inhibitors Fact Sheet" available at cancer.gov).

In some embodiments, the AAA is a short-acting AAA (See US Patent Application Publication No. 20170333413). Short-acting AAAs have shorter average decay periods as compared to long-acting AAAs such as bevacizumab and DC101. Suitable AAAs include, but are not limited to: cediranib (average plasma half-life of about 22 to 27 hours and a peak plasma concentration of 2-8 hours after administration), axitinib (average half-life 2.5 to 6 h), anginex (half-life 50 minutes), sunitinib (average half-life of 40-60 hours), sorafenib (average half-life of about 25-48 hours), pazopanib (average half-life of about 30 hours), vatalanib (average half-life of 4.7 hours), cabozantinib (average half-life of 55 hours), ponatinib (average half-life of 24 hours); lenvatinib (average half-life of 28 hours) and SU6668 (average half-life of 3.6 hours). In some embodiments, the short-acting AAA is Semaxanib/SU5416 (average half-life about 0.5 to 1 hour).

In some embodiments, the anti-angiogenic agents (AAAs) are selected from retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2 (3 h)-oxazolone, methotrexate, mitoxantrone, heparin, interferons, interferon alpha ligand modulators, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, and metalloproteinase inhibitors such as BB-94.

In some embodiments, the anti-angiogenic agent is an antagonist against one or more angiogenic growth factors and/or their receptors. In some embodiments, the angiogenic growth factors include FGF family growth factors, VEGF family growth factors, PDGF family growth factors, HGF family growth factors and Angiopoietin family growth factors. In some embodiments, the angiogenic growth factors include beta-FGF, alpha-FGF, FGF-5, VEGF isoforms, VEGF-C, PDGF, HGF/SF, and Ang-1/Ang-2. In some embodiments, the antagonist is a small molecule antagonist (e.g., a kinase inhibitor against one or more growth factor receptors). In some embodiments, the antagonist is an antibody (e.g., monoclonal antibody) or its binding fragment thereof against the one or more angiogenic growth factors and/or their receptors. In some embodiments, the antagonist is a peptide, polypeptide, aptamer, nucleic acid or its mimic, siRNA or antisense oligonucleotide, viral vector, antibody-drug conjugate, or other molecules that inhibits the signaling of the angiogenic growth factors or their receptors. In some embodiments, the antagonist is a binding fragment of an antibody that has shorter plasma half-life than the corresponding full antibody. Non-limiting examples of such binding fragments include single chain variable fragment (scFv), Diabody (non-covalent dimer of scFv), tandem scFv, bivalent or divalent scFv, antigen-binding fragment (Fab), Fab', F(ab')$_2$. In some embodiments, the antagonist is a scFv or its variant (e.g., Diabody, tandem scFv, bivalent or divalent scFv). In some embodiments, the antagonist is a Fab.

Examples of VEGF receptor antagonists include, but are not limited to, apatinib mesylate, pazopanib, ranibizumab (comprising VL of SEQ ID No. 1 and VH of SEQ ID No. 2), DCB-R0237, X-82, MGCD-265, nintedanib, cabozantinib, vandetanib, altiratinib, MG-516, ramucirumab, lenvatinib mesylate, Duta-101, ponatinib, conbercept, PZ-1, anlotinib hydrochloride, lucitanib hydrochloride, sorafenib, STI-A0168, regorafenib, fruquintinib, NT-503-ECT, regorafenib, axitinib, pegaptanib, PAN-90806, sunitinib, RGX-314, tivozanib, ENMD-2076, UCM-037, cediranib, sulfatinib, GFB-204, AFG-2, JI-101, BNC-420, brivanib alaninate, dovitinib, TAS-115, TTAC-0001, LCB-19, GNR-011, DA-3131, IMC-3C5, HLX-06, rebastinib, motesanib diphosphate, ODM-203, AG-119, PSI-001, famitinib, CLS-1002, DE-120, KN-027, ningetinib, OMP-305B83, Debio-1144, LAU-0901, foretinib, WXH-520, DIG-KT, CYC-116, sevacizumab, APX-004, PMX-20005, vatalanib, D-181, elpamotide, OTSGC-A24, DP-317, UB-924, muparfostat sodium, Angiozyme, ilorasertib, AL-2846, AL-3818, BMS-817378, AL-8326, PTC-299, PRS-050, UBP-1212, RAF-265, CEP-11981, CG-203306, A-1014907, MDX-1, WS-006, ZLJ-33, ABS-393, S-209, MP-0250, KIN-4104, TLK-60404, KN-014, SAR-397769, SAR-131675, CS-3158, golvatinib tartrate, ABT-165, OSI-930, orantinib, icrucumab, PLG-201, PLG-101, BGB-102, squalamine, CS-2164, AR-639, NX-278-L, KBP-7018, IBI-302, AG-321, BFH-772, AD-051.4, TAK-632, IPS-04003, QLNC-3A6, IPS-04001, AP-202, LP-590, telatinib, SCR-1515, BRN-103, LMV-12, PTZ-09, ENMD-1198, ACTB-1011, 4SC-203, AS-3, IXS-312, linifanib, MRC-202, XV-615, mitothiorole, IMC-1C11, NT-502, pegdinetanib, ESBA-903, GSK-2136773, KRN-633, BMS-584622, PF-337210, SA-20896, alacizumab pegol, CLT-007, CLT-006, ZK-261991, SU-14813, DCC-2157, XL-999, BMS-690514, TAK-593, NM-3, PRS-055, AMG-273, BIW-8556, BMS-645737, DMS-3008, NSTPBP-01250, C11C1, EG-3306, AAL-881, AE-941, semaxanib, LY-2401401, OSI-632, Hu2C3, LEO-A, BIBF-100, AG-028262, TX-2036, GFB-111, AB-434, EHT-0204, RG-8803, ZD-4190, ZK-304709, HuMV833, AG-013958, L-000021649, AZD-9935, JNJ-17029259, DX-1235, AG-28345, AG-28191, VGA-1102, R-123942, CEP-5214, KP-0201448, ZK-229561, TBC-2576, CHIR-200131, KM-2550, TG-100-344, AG-13925, LU-343505, TBC-1635, SU-9902, SU-9803, SU-4158, NX-213, SoRI-8790. Additional examples of VEGF/VEGFR antagonists include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP))), anti-VEGF antibodies (e.g., bevacizumab, sevacizumab, ranibizumab, VGX-100 (U.S. Pat. No. 7,423,125), r84 (comprising VL CDR1 of SEQ ID No. 3, VL CDR 2 of SEQ ID No. 4, VL CDR 3 of SEQ ID No. 5, VH CDR 1 of SEQ ID No. 6, VH CDR 2 of SEQ ID No. 7, and VH CDR 3 of SEQ ID No. 8; see U.S. Pat. No. 8,034,905), aflibercept (U.S. Pat. No. 5,952,199), IMC-18F1 (U.S. Pat. No. 7,972,596), IMC-1C11 (PCT/US2000/02180), and ramucirumab (U.S. Pat. No. 7,498,414)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms. In some embodiments, the antagonist is an antigen binding fragment (e.g., scFv or its variant, Fab) of the antibodies described herein. Additional small molecule VEGFR antagonists include 3-amino-5-phenylisothiazole derivatives, conjugated 3-(indolyl)- and 3-(azaindolyl)-4-arylmaleimide compounds, oxetane 3,3-dicarboxamide compounds, 1,6-napthyridine-4-ketone fused heterocyclic, Itraconazole, 3-phenyl-5-ureidoisothiazole-4-carboxamide and 3-amino-5-phenylisothiazole derivatives, and thioether derivatives. Additional anti-VEGFR antibodies include BCD-021 (developed by Biocad), BCD500 (developed by BIOCND), Krabeva (developed by Biocon), CT-P16 (developed by Celltrion), CHS-5217 (developed by Coherus), DRZ_BZ (developed by Dr Reddy's Lab), Cizumab (developed by Hetero), Bevax (developed by mAbxience), ONS-1045 (developed by Oncobiologics/Viropro), HD204 (developed by Prestige Biopharma), Bevacirel (developed by Reliance Life Sciences/Lupin), RPH 001 (developed by R-Pharm), r84 (developed by Avid Biosciences, VL SEQ ID No. 9 and VH SEQ ID No. 10).

In some embodiments, the radiosensitizing agent is a biosimilar of ranibizumab. Thus, in some embodiments, the radiosensitizing agent is a drug selected from the group consisting of: BCD300 (BIOCND, South Korea), SB11 (Biocon/Samsung Bioespis), CKD 701 (Chong Kun Dang Pharmaceutical), CHS-3351 (Coherus), FYB201 (Formycon/Bioeq IP), PF582 (Hospira), Razumab (Intas Biopharmaceuticals), PDP807 (Polus Biopharm), SBS 7001 (Siam Bioscience), Xlucane (Xbrane Biopharma/Stada Arzneimeittel).

Examples of FGF receptor antagonists include CPL-043, nintedanib, BLU-554, masitinib, lenvatinib mesylate, ponatinib, lucitanib hydrochloride, regorafenib, FGFR2-ADC, BAY-1179470, regorafenib, LY-3076226, erdafitinib, FGF-401, squalamine, B-701, ENMD-2076, UCM-037, HMPL-453, sulfatinib, fenretinide, infigratinib, AZD-4547, alofanib, BAY-1163877, pirfenidone, FPA-144, RTEF-651, brivanib alaninate, dovitinib, Debio-1347, ARQ-087, OM-RCA-001, TAS-120, danusertib, ODM-203, S-49076, JNJ-42441707, INCB-054828, LY-2874455, ASP-5878, FP-1039, Loxo-103, PMX-20005, D-181, EDP-317, muparfostat sodium, AL-3818, AL-8326, ZLJ-33, KIN-4104, RG-7444, orantinib, LQN-725, Pantarin, PP-0612, AV-370, AV-369, K-983, BPS-03251, CT-400P, AM-001, PAT-PA1, TRC-093, DAPI-01, KW-2449, XL-999, ProMabin, PD-166285, EncaminC, SSR-128129, TG-100801, TBC-256, PD-089828, SU-9902, FCE-27164, and GMI-306. Additional examples of FGF or FGF receptor antagonist include, but are not limited to, GP369, BAY1187982, MFGR1877S, and FP-1039 (GSK3052230).

Examples of PDGF receptor antagonists include nilotinib, pazopanib, imatinib, X-82, nintedanib, masitinib, MG-516, DCC-2618, lenvatinib mesylate, Duta-101, olaratumab, ponatinib, lucitanib hydrochloride, pirfenidone, BLU-285, sorafenib, PK-10571, PK-453, axitinib, sunitinib, AR-13154, quizartinib dihydrochloride, cediranib, GFB-204, JI-101, dovitinib, XB-2202, ARQ-087, HLX-08, puquitinib mesylate, NT-506-ECT, famitinib, CLS-1002, KN-027, vatalanib, D-181, crenolanib, ilorasertib, AL-8326, AD-054.9, CG-026481, ZLJ-33, AbyD-3263, KN-014, orantinib, CS-2164, ARC-127, KBP-7018, AG-321, QLNC-3A6, tovetumab, amuvatinib, XV-615. mitothiorole, tandutinib, BMS-584622, ARRY-768, DCC-2157, XL-844, TAK-593, CP-673451, PD-166285, AMG-273, LY-2401401, LEO-A, GFB-111, CDP-860, AG-1295, RTKA-111, PD-089828, RPR-127963E, KI-6896, KI-6783, RPR-101511a, SU-65847, SU-65786, luteusin-C, WIN-41662, and CGP-53716. Additional example of PDGF or PDGF receptor antagonists includes, but is not limited to, Olaratumab (Lartruvo).

Examples of c-Met antagonist include AMG-208, AMG-337, AMG-458, PHA-665752, SU11274, NPS-1034, SGX-523, BMS-777607, tepotinib, BMS-794833, NVP-BVU972, MK-2461, MGCD-265, golvatinib, JNJ-38877605, BMS-754807, PF-04217903, savolitinib, crizotinib, tivantinib, cabozantinib, foretinib, capmatinib (INC280), onartuzumab, ficlatuzumab or rilotumumab. Additional examples of c-Met antagonist include, but are not limited to, Rilotumumab (AMG102), Ficlatuzumab (SCH900105), TAK-701, Onartuzumab (MetMab), and Emibetuzumab (LY-2875358).

Examples of Angiopoietin/Tie receptor antagonist include, but are not limited to, Nesvacumab (REGN910), AMG780, MEDI3617, Vanucizumab, and Trebananib (AMG386).

Recent studies have shown that anti-angiogenic drugs can de-repress ASMase/ceramide pathway to enhance ceramide-mediated endothelial apoptosis if delivered prior but close to the time of SDRT, e.g., less than two hours before SDRT (Rao et al. *Radiotherapy and oncology: journal of the European Society for Therapeutic Radiology and Oncology* 111, 88-93,2014). In some embodiments, the AAA is or has been administered about 0.5 to 48 hours, 0.5 to 24 hours, 0.5 to 12 hours, 0.5 to 10 hours, 0.5 to 5 hours, about 0.5 to 4 hours, about 0.5 to 3 hours, about 0.5 to 2 hours, about 0.5 to 1.5 hours, about 0.5 to 1 hour, 1 to 5 hours, about 1 to 4 hours, about 1 to 3 hours, about 1 to 2 hours, about 1 to 1.5 hour, 1.5 to 5 hours, about 1.5 to 4 hours, about 1.5 to 3 hours, about 1.5 to 2 hours, 2 to 5 hours, about 2 to 4 hours, about 2 to 3 hours, about 3 to 5 hours, about 3 to 4 hours, about 4 to 5 hours, about 10 to 48 hours, about 10 to 24 hours, about 10 to 12 hours, about 12 to 48 hours, about 12 to 24 hours, or about 24 to 48 hours before delivery of radiation. In some embodiments, the AAA is or has been administered no more than about 2 hours before delivery of radiation. In some embodiments, the AAA is or has been administered no more than about 1.5 hours before delivery of radiation. In some embodiments, the AAA is or has been administered no more than about 1 hour before delivery of radiation. In some embodiments, the AAA is or has been administered within a half-hour before delivery of radiation.

Other Exemplary Radiosentizing Agents, Including ASM/Cer Activating Agents

In some embodiments, the ASM/Cer activating agent is a protein kinase C (PKC) activator. Exemplary PKC activator includes, but are not limited to, phorbol 12-myristate 13-acetate (PMA), Phorbol-12,13-dibutyrate, ROPA (Resiniferonol-9,13,14-orthophenyl acetate), 1-Oleoyl-2-acetyl-sn-glycerol, (±)-1,2-Didecanoylglycerol (10:0), (±)-1,2-Dioleoylglycerol (18:1) (−)-Indolactam V, 1-Stearoyl-2-arachidonoyl-sn-glycerol, Ingenol-3-angelate, Prostratin.

In some embodiments, the ASM/Cer activating agent is tumor necrosis factor (TNF)-alpha. In some embodiments, the ASM/Cer activating agent is an agent that downregulates or inhibits the expression and/or activity of caveolin-1 (CAV1). In some embodiments, the ASM/Cer activating agent is CD95 (Fas/APO-1). In some embodiments, the ASM/Cer activating agent is lipopolysaccharide (LPS) and/or Palmitic acid (PA). In some embodiments, the ASM/Cer activating agent is lysobisphophatidic acid (LBPA) and/or phosphatidylinositol (PI).

Ceramide Compositions

In some embodiments, the ASM/Cer activating agent is a composition comprising ceramide. In some embodiments, the composition is a composition of ceramide nanoparticles or nanoliposomes (See ClinicalTrials.gov Identifier: NCT02834611; Kester et al., Biol Chem. 2015 June; 396 (6-7):737-47; and Tagaram et al., Gut. 2011 May; 60(5): 695-701).

Recombinant ASMase

In some embodiments, the ASM/Cer activating agent is a recombinant ASMase protein. Recombinant ASM (rhASM) has been manufactured for clinical use and received orphan drug status for Type B NPD in 2000. rhASM is non-toxic at high doses when administered to wild type mice (Miranda et al. *FASEB J.* 2000; 14: 1988-1995). In some embodiments, rhASM is administered intratumorally. In some embodiments, rhASM is encapsulated in a particle (e.g., a nanoparticle, a liposome, an exosome, or micelle) and administered intravenously (Aldosari et al., Eur J Pharm Biopharm. 2019 April; 137:185-195).

Ceramidase and Sphingosine Kinase Antagonists

In some embodiments, the ASM/Cer activating agent is a ceramidase (CDase) and/or sphingosine kinase antagonist.

Examples of ceramidase antagonist include, but are not limited to, Oleylethanolamide, D-NMAPPD, ceramidastin, Carmofur, Ceranib-1, Ceranib-2, B13, D-e-MAPP, LCL85, LCL464, N-oleoylethanolamine (NOE), DM102, DP24c, LCL204, LCL385, KPB-67, KPB-70, SACRAC, RBM1-12, RBM1-13, and other ceramidase antagonists. See Saied et al., Cell Physiol Biochem 2014; 34:197-212.

Examples of sphingosine kinase antagonists include, but are not limited to, SKI-II, PF-543, ABC294640, ABC294735, SK1-I (BML-258), VPC96091 and its derivatives, SLR080801, SLP7111228, MP-A08, K145, 3-(2-amino-ethyl-alkylidene)-thiazolidine-2,4-dione and 1-(2-amino-ethyl)-alkylidene-1,3-dihydro-indol-2-one derivatives, 2-piperidine thiazole derivatives, and other sphingosine kinase antagonists. See Lynth et al., Expert Opin Ther Pat. 2016 December; 26(12): 1409-1416.

Additional Radiosensitizers and their Derivatives

In some embodiments, the methods described herein comprise delivering radiation to a subject in need thereof after or simultaneously with the administration of one or more radiosensitizers and/or their derivatives.

Radiosensitizers make tumor cells more sensitive to radiation therapy. Without wishing to be bound by theory, some radiosensitizers interfere with the regulation of cell cycle checkpoints in tumor cells, especially those with DNA damage caused by radiation therapy. Some radiosensitizers may crosslink DNA strands, exacerbating DNA damage caused by radiation therapy. In some embodiments, the radiosensitizer is also an ASM/Cer activating agent. In some embodiments, a derivative of the radiosensitizer described herein is used.

In some embodiments, the radiosensitizer is a fluoropyrimidine, gemcitabine, a platinum analog such as cisplatin, NBTXR3, Nimoral, trans sodium crocetinate (TSC), NVX-108, misonidazole, metronidazole, tirapazamine, vandate or another radiosensitizer.

In some embodiments, the radiosensitizer is a fluorocarbons or its derivative. In some embodiments, the radiosensitizer is a dodecafluoropentane or its emulsion (DDFPe). In some embodiments, the DDFPe is administered as a product currently in clinical development under the name NVX-108. In some embodiments, the radiosensitizers is F-1,3-dimethyladamane, F-trimethylbicyclo[3.3.1]nonane, F-tributylamine (FC-43, 3M Company), perfluorodecalin or perfluorooctylbromide. In some embodiments, the radiosensitizer is a lower molecular weight fluorocarbon. In some embodiments, the fluorocarbon has a boiling point from about −4 degrees centigrade to about 100 degrees centigrade. In some embodiments, the fluorocarbon has a boiling point from about 20 to about 80 degrees C. In some embodiments, the fluorocarbon is selected from the group consisting of perfluorobutane, perfluoropentane, perfluorohexane, perfluoroheptane and perfluorooctane.

In some embodiments, the radiosensitizers are halogenated nucleosides or their analogs. In some embodiments, the halogenated nucleoside analogs include 5-iodo-2'-deoxyuridine (IUdR), 5-bromo-2'-deoxyuridine (BUdR), 5-iodo-2-pyrimidinone-2'-deoxyribose (IPdR), or a combination thereof. In some embodiments, the radiosensitizer may alternatively or additionally include one or more PdR analogs described in Cheng, et al., U.S. Pat. No. 5,728,684, the entirety of which is incorporated by reference herein. In some embodiments, the radiosensitizer is IPdR.

In some embodiments, the radiosensitizer is a poly-(ADP-ribose)-polymerase (PARP) inhibitor. PARP inhibitors include Olaparib, Rucaparib, Veliparib, LT 626, PJ34, GPI 21016, 4-amino-1,8-naphthalimide, 3-Aminobenzamide, and Niraparib.

In some embodiments, the radiosensitizers are nitroimidazole alkylsulfonamides. In some embodiments, the radiosensitizer is ATR Inhibitor AZD6738. In some embodiments, the radiosensitizer is a histone H3 demethylase Inhibitor (e.g., GSK-J4).

In some embodiments, the radiosensitizer is a histone deacetylase (HDAC) inhibitor. HDAC inhibitors include Vorinostat (SAHA), Entinostat (MS-275), Panobinostat (LBH589), Trichostatin A (TSA), Mocetinostat (MGCD0103), Belinostat (PXD101), Romidepsin (FK228, Depsipeptide), and MC1568.

Additional radiosensitizer agents include, but are not limited to, taxane containing at least 2 electron-affinic radiosensitizing functional groups, 2-carboxyaldehyde pyridine thiosemicarbazone compound or prodrug thereof, substituted diamines containing 2-4 electron-affinic radiosensitizing functional groups, lanthanide-based nanoparticles, platinum complexes with one radiosensitizing ligand, indazolpyrrolotriazines, anthraquinones, and monomethyl auristatin e (mmae) and derivatives thereof.

Treatments of the Present Disclosure

In some embodiments, the present disclosure provides methods of treating a tumor in a subject in need thereof comprising subdividing the total planning target volume (PTV) into two or more virtual planning target sub-volumes, wherein a first high radiation dose is delivered to a first planning target sub-volume ($PTV_{HD}$) and a second lower radiation dose is delivered to a second planning target sub-volume ($PTV_{PMDS}$).

In some embodiments, the first planning target sub-volume ($PTV_{HD}$) comprises at least 60% of the total PTV. In some embodiments, the first planning target sub-volume ($PTV_{HD}$) is between about 60% and about 95% of the total tumor volume or PTV. In some embodiments, the first planning target sub-volume ($PTV_{HD}$) is about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% of the total PTV, including all ranges and subranges therebetween. In some embodiments, the first planning target sub-volume ($PTV_{HD}$) is about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, or 40% of the total tumor volume, including all ranges and subranges therebetween.

In some embodiments, the first planning target sub-volume ($PTV_{HD}$) is at least about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, of the total tumor volume, including all ranges and subranges therebetween. Thus, in some embodiments, first planning target sub-volume ($PTV_{HD}$) is at least about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% of the total PTV or total tumor volume.

In some embodiments, the second target sub-volume ($PTV_{PMDS}$) is between about 5% and about 40% of the total PTV. In some embodiments, the second target sub-volume ($PTV_{PMDS}$) is between about 10% and about 40%, about 15% and about 40%, about 20% and about 40%, about 25% and about 40%, about 30% and about 40%, or about 35% and about 40%, of the total PTV. In some embodiments, the second target sub-volume ($PTV_{PMDS}$) is about 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 1%, 14%, 13%, 12%, 11%, 10%, 9%, 8%, 7%, 6%, or 5% of the total PTV, including all ranges and subranges therebetween. In some embodiments, the second target sub-volume ($PTV_{PMDS}$) is about 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the total tumor volume, including all ranges and subranges therebetween. Thus, in some embodiments, the second target sub-volume ($PTV_{PMDS}$) is at least about 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the total PTV or total tumor volume.

In some embodiments, the level of ischemic injury of a tumor begins to plateau after 24 Gy. However, higher radiation dosages are within the scope of the present inventions. In some embodiments, the first radiation dose (e.g., administered to $PTV_{HD}$) is between about 15 Gy and about 60 Gy. In some embodiments, the first radiation dose is between about 20 Gy and about 60 Gy, about 25 Gy and about 60 Gy, about 30 Gy and about 60 Gy, about 35 Gy and about 60 Gy, about 40 Gy and about 60 Gy, about 45 Gy and about 60 Gy, about 50 Gy and about 60 Gy, about 55 Gy and about 60 Gy, about 15 Gy and about 55 Gy, about 15 Gy and about 50 Gy, about 15 Gy and about 45 Gy, about 15 Gy and about 40 Gy, about 15 Gy and about 35 Gy, about 15 Gy and about 30 Gy, or about 15 Gy and about 25 Gy. In some embodiments, the first radiation dose is between about 15 Gy and about 30 Gy, about 20 Gy and about 30 Gy, about 25 Gy and about 30 Gy, about 15 Gy and about 25 Gy, about 15 Gy and about 20 Gy. In some embodiments, the first radiation dose is between about 18 Gy and about 24 Gy. In some embodiments, the first radiation dose is between about 20 Gy and about 24 Gy. In some embodiments, the first radiation dose is at least about 15 Gy, 16 Gy, 17 Gy, 18 Gy, 19 Gy, 20 Gy, 21 Gy, 22 Gy, 23 Gy, 24 Gy, 25 Gy, 26 Gy, 27 Gy, 28 Gy, 29 Gy, or at least about 30 Gy. In some embodiments, the first radiation dose is at least about 20 Gy. In some embodiments, the first radiation dose is at least about 24 Gy.

Thus, in some embodiments the first radiation dose is about 15 Gy, 16 Gy, 17 Gy, 18 Gy, 19 Gy, 20 Gy, 21 Gy, 22 Gy, 23 Gy, 24 Gy, 25 Gy, 26 Gy, 27 Gy, 28 Gy, 29 Gy, 30 Gy, 31 Gy, 32 Gy, 33 Gy, 34 Gy, 35 Gy, 36 Gy, 37 Gy, 38 Gy, 39 Gy, 40 Gy, 41 Gy, 42 Gy, 43 Gy, 44 Gy, 45 Gy, 46 Gy, 47 Gy, 48 Gy, 49 Gy, 50 Gy, 51 Gy, 52 Gy, 53 Gy, 54 Gy, 55 Gy, 56 Gy, 57 Gy, 58 Gy, 59 Gy, or 60 Gy, including all ranges and subranges therebetween.

In some embodiments, the present disclosure teaches the use of radiosensitizing agents to reduce the amount of necessary radiation to induce the bystander effect. In some embodiments the first radiation dose is at least about 15 Gy, 16 Gy, 17 Gy, 18 Gy, 19 Gy, 20 Gy, 21 Gy, 22 Gy, 23 Gy, 24 Gy, 25 Gy, 26 Gy, 27 Gy, 28 Gy, 29 Gy, 30 Gy, 31 Gy, 32 Gy, 33 Gy, 34 Gy, 35 Gy, 36 Gy, 37 Gy, 38 Gy, 39 Gy, 40 Gy, 41 Gy, 42 Gy, 43 Gy, 44 Gy, 45 Gy, 46 Gy, 47 Gy, 48 Gy, 49 Gy, 50 Gy, 51 Gy, 52 Gy, 53 Gy, 54 Gy, 55 Gy, 56 Gy, 57 Gy, 58 Gy, 59 Gy, or 60 Gy.

In some embodiments, the total radiation dose disclosed for the first radiation dose is administered in a single session (i.e. SDRT), and is not fractionated across multiple sessions. In some embodiments, the SDRT-PMDS dose-sculpting method can be used in one or more radiation doses administered as part of SABR therapy. In some embodiments, the first radiation dose reduces the amount of radiation required to treat the remaining tumor portions (e.g., the second tumor volume) through a bystander effect (e.g., AMSase-mediated radiosensitization). In such embodiments, the effective dose for the total tumor volume or total PTV is reduced compared to the effective dose for tumors receiving the same radiation dose across the entirety of the tumor volume.

In some embodiments, the second radiation dose is less than the toxicity threshold of an adjacent OAR. Threshold radiation doses for multiple organs are provided in Tables 1A-1B, excerpted from Benedict et al., Stereotactic body radiation therapy: The report of AAPM Task Group 101. Med. Phys. 37(8), August 2010.

In some embodiments, the $PTV_{PMDS}$ sub-volume is adjacent to an OAR. In some embodiments, the $PTV_{PMDS}$ sub-volume is adjacent to a dose limiting OAR. In some embodiments, the $PTV_{PMDS}$ sub-volume overlaps with an OAR or portion thereof. In some embodiments, the $PTV_{PMDS}$ sub-volume overlaps with a dose limiting OAR or portion thereof. A person having skill in the art will recognize however, that in some embodiments, the shaping of the radiation dose to conform with tumor shape can result in other sub volumes of the PTV receiving a lower radiation dose than the radiation dose delivered to the $PTV_{HD}$ (e.g., due to the penumbra radiation fall off of the radiation beam used for the $PTV_{HD}$). In some embodiments, the additional PTV sub-volumes receiving lower radiation that are not adjacent or overlapping with the OAR are additional PTV sub volumes (i.e. $PTV_{SV3-SVxx}$). In some embodiments, these additional PTV sub-volumes receiving lower radiation doses are considered part of the $PTV_{PMDS}$. Thus, in some embodiments, the $PTV_{PMDS}$ encompasses portions of the total PTV that are non-adjacent or distal to an OAR. In some embodiments, the $PTV_{PMDS}$ sub-volume encompasses portions of the total PTV that are non-adjacent or distal to a dose limiting OAR. In some embodiments, the $PTV_{PMDS}$ sub-volume does not overlap with an OAR or portion thereof. In some embodiments, the $PTV_{PMDS}$ sub-volume does not overlap with a dose limiting OAR or portion thereof.

In some embodiments, the radiation dose delivered to the $PTV_{PMDS}$ is a fall-off dose from the radiation dose delivered to the $PTV_{HD}$. Thus in some embodiments, the radiation dose administered to the $PTV_{PMDS}$ is not homogenous, but is instead delivered as dose reduction gradient starting from the high (e.g., 24 Gy) radiation dose delivered to the $PTV_{HD}$, and ending in the distal portion of the whole tumor PTV encountering the OAR. In some embodiments, the radiation dose delivered to the $PTV_{PMDS}$ comprises the penumbra or "penumbral dose" from the radiation beam. In some embodiments, the dose reduction gradient is designed so as to minimize radiation exposure of the OAR, such that the distal portion of the PTV corresponds to the tumor tissue closest to the OAR and received the lowest radiation exposure. In such embodiments, the radiation dose delivered to the distal portion of the PTV is referred to as the "distal surface isodose".

In some embodiments, the second radiation dose is less than about 23 Gy. In some embodiments, the second radiation dose is between about 12 Gy and about 23 Gy. In some embodiments, the second radiation dose is between about 18 Gy and about 23 Gy. In some embodiments, the second radiation dose is less than about 18 Gy. In some embodiments, the second radiation dose is between about 12 Gy and about 18 Gy. In some embodiments, the second radiation dose is less than about 12 Gy. In some embodiments, the second radiation dose is between about 10 Gy and about 18 Gy. In some embodiments, the second radiation dose is between about 11 Gy and about 18 Gy, about 12 Gy and about 18 Gy, about 13 Gy and about 18 Gy, about 14 Gy and about 18 Gy, about 15 Gy and about 18 Gy, about 16 Gy and about 18 Gy, about 17 Gy and about 18 Gy, about 10 Gy and about 17 Gy, about 10 Gy and about 16 Gy, about 10 Gy and about 15 Gy, about 10 Gy and about 14 Gy, about 10 Gy and about 13 Gy, about 10 Gy and about 12 Gy, or between about 10 Gy and about 11 Gy. In some embodiments, the second radiation dose is less than about 18 Gy, 17 Gy, 16 Gy, 15 Gy, 14 Gy, 13 Gy, 12 Gy, 11 Gy, or less than about 10 Gy. In some embodiments, the second radiation dose is less than about 18 Gy. In some embodiments the second radiation dose is about 1 Gy, 2 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy, or 20 Gy including all ranges and subranges therebetween.

In some embodiments, the bystander effect triggered by the first radiation dose reduces the amount of radiation required to treat the second tumor volume. In some embodiments, the second radiation dose is between about 10% and about 50% less than the first radiation dose. In some embodiments, the second radiation dose is between about 15% and about 50% less than the first radiation dose, about 20% and about 50% less than the first radiation dose, about 25% and about 50% less than the first radiation dose, about 30% and about 50% less than the first radiation dose, about 35% and about 50% less than the first radiation dose, about 40% and about 50% less than the first radiation dose, about 45% and about 50% less than the first radiation dose, about 10% and about 45% less than the first radiation dose, about 10% and about 40% less than the first radiation dose, about 10% and about 35% less than the first radiation dose, about 10% and about 30% less than the first radiation dose, about 10% and about 25% less than the first radiation dose, about 10% and about 20% less than the first radiation dose, about 10% and about 15% less than the first radiation dose. In some embodiments, the second radiation dose is at least about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% less than the first radiation dose.

In some embodiments, the first radiation dose is between about 18 Gy and about 24 Gy and the second radiation dose is between about 10 Gy and about 18 Gy. In some embodiments, the first radiation dose is at least about 20 Gy and the second radiation dose is between about 10 Gy and about 18 Gy. In some embodiments, the first radiation dose is at least about 22 Gy and the second radiation dose is between about 10 Gy and about 18 Gy. In some embodiments, the first radiation dose is at least about 24 Gy and the second radiation dose is between about 10 Gy and about 18 Gy. In some embodiments, the first radiation dose is between about 18 Gy and about 24 Gy and the second radiation dose is about 16 Gy. In some embodiments, the first radiation dose is between about 18 Gy and about 24 Gy and the second radiation dose is about 18 Gy. In some embodiments, the first radiation dose is about 24 Gy and the second radiation dose is about 16 Gy.

As discussed above, in some embodiments, the $PTV_{PMDS}$ is exposed to a steep dose gradient to fulfil dose/volume constraints of an OAR. Persons having skill in the art will recognize that, in some embodiments, such a dose gradient would not result in a homogenous radiation dosage at the $PTV_{PMDS}$. Thus, in some embodiments, the dose delivered to the $PTV_{PMDS}$, as used herein is the lowest dose received by a tumor cell within the $PTV_{PMDS}$ (e.g., as measured by D95 or D99 values).

In some embodiments, the radiation dose delivered to 99% (D99) of the second planning target sub-volume ($PTV_{PMDS}$ or $PTV_{V2}$) (the $PTV_{V2}$-D99 or $PTV_{PMDS}$-D99) is at least about 10% to about 40% lower than the radiation dose covering 99% (D99) of the first planning target sub-volume ($PTV_{HD}$ or $PTV_{V1}$) (the $PTV_{V1}$-D99 or $PTV_{HD}$-D99). In some embodiments, the $PTV_{V2}$-D99 is at least about 15% to about 40%, about 20% to about 40%, about 25% to about 40%, about 30% to about 40%, about 35% to about 40%, about 10% to about 35%, about 10% to about 30%, about 10% to about 25%, about 10% to about 20%, or about 10% to about 15% lower than the $PTV_{V1}$-D99. In some embodiments, the $PTV_{V2}$-D99 is at least about 10% to about 30%, about 15% to about 30%, about 20% to about 30%, about 25% to about 30%, about 10% to about 25%, about 10% to about 20%, or about 10% to about 15% lower than the $PTV_{V1}$-D99.

In some embodiments, the $PTV_{V2}$-D99 radiation dose is at least about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% less than the $PTV_{V1}$-D99 radiation dose.

In some embodiments, the radiation dose covering 95% (D95) of the second planning target sub-volume ($PTV_{V2}$) (the $PTV_{V2}$-D95 or $PTV_{PMDS}$-D95) is at least about 10% to about 40% lower than the radiation dose covering 95% (D95) of the first planning target sub-volume ($PTV_{V1}$) (the $PTV_{V1}$-D95 or $PTV_{HD}$-D95). In some embodiments, the $PTV_{V2}$-D95 is at least about 15% to about 40%, about 20% to about 40%, about 25% to about 40%, about 30% to about 40%, about 35% to about 40%, about 10% to about 35%, about 10% to about 30%, about 10% to about 25%, about 10% to about 20%, or about 10% to about 15% lower than the $PTV_{V1}$-D95. In some embodiments, the $PTV_{V2}$-D95 is at least about 10% to about 30%, about 15% to about 30%, about 20% to about 30%, about 25% to about 30%, about 10% to about 25%, about 10% to about 20%, or about 10% to about 15% lower than the $PTV_{V1}$-D95.

In some embodiments, the $PTV_{V2}$-D95 radiation dose is at least about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% less than the $PTV_{V1}$-D95 radiation dose.

In some embodiments, treatment of tumors according to the methods provided herein reduce the incidence of local relapse by at least 10% compared to administration of fractionated radiotherapy. In some embodiments, treatment of tumors according to the methods provided herein reduce the incidence of local relapse by at least 15%, 20%, 25%, or 30% compared to administration of fractionated radiotherapy.

Radiation Sources

Radiotherapy methods described herein may include radiation produced by an X-ray beam, an electron beam, or a proton beam produced by a linear accelerator. The radiotherapy intended in the present methods may be carried out through a protocol which is generally employed in this technical field and known to those skilled in the art. For example, the radiotherapy includes radiation of cesium, iridium, iodine, or cobalt. In some embodiments, the radiotherapy may be systemic radiation (to acute leukemia, malignant lymphoma, and a certain type of solid cancer), but is preferably locally focused on site(s); i.e., tumor sites and solid cancer tissues (abdomen, lung, liver, lymph nodes, head, etc.).

Radiation can be delivered using a variety of machines known in the art, including but not limited to x-ray machines, gamma machines, linear accelerators (LINAC), particle accelerators, and circular or cyclic RF accelerators. Particle accelerators include electrostatic particle accelerators, electrodynamic particle accelerators, and electromagnetic particle accelerators (e.g., magnetic induction accelerators). Circular or cyclic RF accelerators include microtrons, betatrons, cyclotrons, synchrocyclotrons and isochronous cyclotrons, synchrotrons, electron synchrotrons, storage rings, and FFAG accelerators.

Standard X-ray machines include superficial x-ray machines and orthovoltage X-ray machines. Examples include but are not limited to X-rad machines (Precision X-Ray), MultiRad machines (Precision X-Ray) or RAD source machines (Precision X-Ray).

In some embodiments, the radiation is administered using a Linear accelerator (LINAC) machine. LINAC machines use X-rays (photons) and are commonly used to treat tumors both in the brain and other parts of the body. LINACs accelerate electrons using a tuned-cavity waveguide, in which the RF power creates a standing wave. Some LINACs have short, vertically mounted waveguides, while higher energy machines tend to have a horizontal, longer waveguide and a bending magnet to turn the beam vertically towards the patient. Medical LINACs use monoenergetic electron beams between 4 and 25 MeV, giving an X-ray output with a spectrum of energies up to and including the electron energy when the electrons are directed at a high-density (such as tungsten) target. The electrons or X-rays can be used to treat both benign and malignant disease. The LINAC produces a reliable, flexible and accurate radiation beam. Various types of linac accelerators are available: some provide X-rays only in the low megavoltage range (4 or 6 MV), while others provide both X-rays and electrons at various megavoltage energies. A typical modern high-energy linac will provide two photon energies (6 and 18 MV) and several electron energies (e.g., 6, 9, 12, 16 and 22 MeV) (Radiation Oncology Physics: A Handbook for Teachers and Students E. B. PODGORSAK). See International Publication No. WO 2019/106667 A1. More exotic particles, such as protons, neutrons, heavy ions and negative mesons, all produced by special accelerators, may be also used. Exemplary LINAC machines include the CyberKnife® (Accuray, Inc.), PRIMUS™ (Siemens), Elekta Synergy® (Elekta), and TrueBeam® (Varian). Elekta Precise Systems (Elekta), ONCOR (Siemens), TomoTherapy Machines, Elekta Versa HD (Elekta), Varian 21/23 series with OBI and RapidArc, Varian Triology with RapidArc, Cyberknife M6, CyberKnife VSI, Cyberknife G4 & VSI, Elekta Infinity, Varian iX, Varian Trilogy, Basic Varian 21/23 Series, Basic Varian 600CD/6EX. See also International Publication No. WO 2019/106667.

In some embodiments, the radiation is administered using a gamma machine. Gamma machines include various radioactive sources such as Caesium-137, Cobalt-60 or Iridium-192. Examples of Caesium-137 Gamma radiation devices include, but are not limited to, BIOBEAM GM 2000/3000/8000 that generates between 2.5-5 Gy/min or Gammacell 1000 Elite/3000 Elan that generate between 3.5-14 Gy/min. In some embodiments, the radiation is administered using a Gamma Knife machine. A Gamma Knife typically contains 201 cobalt-60 sources of approximately 30 curies (1.1 TBq), each placed in a hemispheric array in a heavily shielded assembly. The device aims gamma radiation through a target point in the patient's brain. The patient wears a specialized helmet that is surgically fixed to the skull, so that the brain tumor remains stationary at the target point of the gamma rays. Exemplary Gamma Knife machines include the Leksell Gamma Knife® Perfexion™ (Elekta) and the Gamma Knife® C™ (Elekta). See also U.S. Publication No. 2011/0160513 A1.

In some embodiments, the radiation is administered using Proton beam therapy (also known as charged particle radiosurgery). Proton beam therapy uses protons, rather than X-rays to treat tumors. Exemplary Proton beam machines include the MEVION S250i™ with HYPERSCAN™ (MEVION medical systems), MEVION S250mx™ (MEVION medical systems), Hitachi Probeat-V Proton Beam Therapy System, ProBeam 360 deg Proton Therapy System (Varian), ProBeam® Compact Single-Room Proton Therapy Solution (Varian), ProBeam® Compact Multiple-Room Proton Therapy Solution (Varian), and Eclipse™ for Proton (Varian).

Systems for the Present Disclosure and Computer System Hardware

In some embodiments, the present disclosure teaches systems or devices capable of carrying out the SDRT-PMDS treatment methods disclosed herein. In some embodiments, the systems of the present disclosure comprise a) an imaging device; b) a radiation source; and c) an electronic compute device ("electronic device"). The electronic device can include one or more memories and one or more processors operatively coupled to at least one of the one or more memories, and configured to execute instructions stored on the at least one of the one or more memories, the processor configured to carry out the SDRT-PMDS method disclosed herein.

Figure 2:
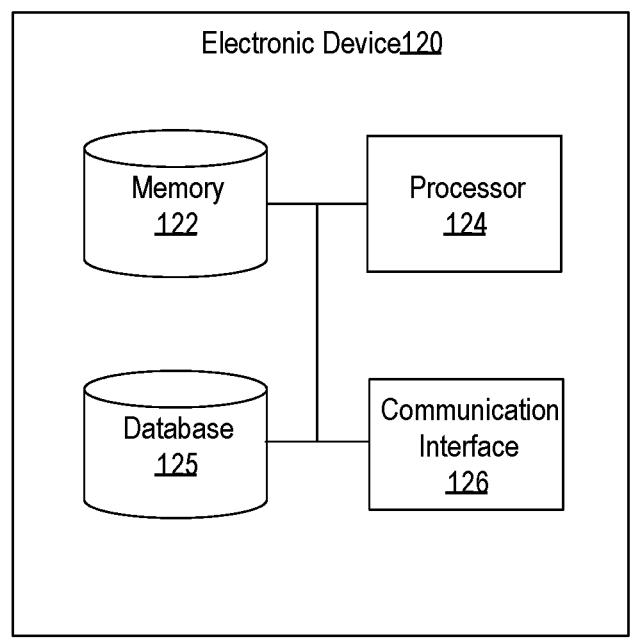

By way of example, FIGS. 1 and 2 illustrate a system 100 configured to provide the SDRT-PMDS treatment methods described herein, according to an embodiment. While various components, elements, features, and/or functions may be described below, it should be understood that they have been presented by way of example only and not limitation. Those skilled in the art will appreciate that changes may be made to the form and/or features of the system 100 without altering the ability of the system 100 to perform the function of providing the SDRT-PMDS treatment methods described herein.

The system 100 can include at least an imaging device 110, a radiation source 115, and an electronic compute device 120 which are in communication via a network 105. As described in further detail herein, in some implementations, the system 100 can be implemented such that the imaging device 110 captures one or more images of a target tumor. In some instances, the imaging device 110 can also capture one or more images of an OAR in contact with, adjacent to, or otherwise near the target tumor. The electronic compute device 120 can define a total planning target volume ($PTV_{TOTAL}$) including a first planning target volume ($PTV_{HD}$) and a second planning target volume ($PTV_{PMDS}$). The electronic compute device 120 can define a SDRT-PMDS radiotherapy treatment plan and can send to the radiation source 115 a signal indicative of an instruction to deliver radiation doses to the $PTV_{TOTAL}$ in accordance with the SDRT-PMDS radiotherapy treatment plan.

The network 105 can be any type of network(s) such as, for example, a local area network (LAN), a wireless local area network (WLAN), a virtual network such as a virtual local area network (VLAN), a wide area network (WAN), a metropolitan area network (MAN), a worldwide interoperability for microwave access network (WiMAX), a telephone network (such as the Public Switched Telephone Network (PSTN) and/or a Public Land Mobile Network (PLMN)), an intranet, the Internet, an optical fiber (or fiber optic)-based network, a cellular network, and/or any other suitable network. Moreover, the network 105 and/or one or more portions thereof can be implemented as a wired and/or wireless network. In some implementations, the network 105 can include one or more networks of any type such as, for example, a wired or wireless LAN and the Internet.

The imaging device 110 can be any suitable machine, device, and/or system. For example, the imaging device 110 can be any of those described in detail above. In some embodiments, the imaging device 110 can be a computed tomography (CT) machine. In some embodiments, the imaging device 110 can be a magnetic resonance imaging (MRI) machine, a positron emission tomography (PET) machine, an ultrasonic imaging machine, and/or any other suitable imaging machine. In some embodiments, the imaging device 110 can be a machine capable of capturing images via any combination of imaging modalities (e.g., a CT scan, a MRI scan, a PET scan, an ultrasound scan, and/or the like). In some implementations, the imaging device 110 can be in communication with the radiation source 150 and/or the electronic device 120 via the network 105. In some implementations, the imaging device 110 can be included in a machine that further includes at least one of the radiation source 115 and/or the electronic device 120.

The radiation source 115 can be any suitable machine, device, and/or system. For example, the radiation source 115 can be any of those described in detail above. In some implementations, the radiation source 115 can be in communication with the imaging device 110 and/or the electronic device 120 via the network 105. In some implementations, the radiation source 115 can be included in a machine that further includes at least one of the imaging device 110 and/or the electronic device 120.

The electronic compute device 120 ("electronic device") can be any suitable hardware-based computing device configured to send and/or receive data via the network 105 and configured to receive, process, define, and/or store data such as, for example, one or more images, radiotherapy treatment plans, patient profiles, etc. In some embodiments, the electronic device 120 can be, for example, a PC, device, a workstation, a server device or a distributed network of server devices, a virtual server or machine, and/or the like. In some embodiments, the electronic device 120 can be a smartphone, a tablet, a laptop, and/or the like. The components of the electronic device 120 can be contained within a single housing or machine or can be distributed within and/or between multiple machines.

As shown in FIG. 2, the electronic device 120 can include at least a memory 122, a processor 124, and a communication interface 126. The memory 122, the processor 124, and the communication interface 126 can be connected and/or electrically coupled (e.g., via a system bus or the like) such that electric and/or electronic signals may be sent between the memory 122, the processor 124, and the communication interface 126. The electronic device 120 can also include and/or can otherwise be operably coupled to a database 125 configured, for example, to store data associated with files accessible via the network 105, as described in further detail herein.

The memory 122 of the electronic device 120 can be, for example, a RAM, a memory buffer, a hard drive, a ROM, an EPROM, a flash memory, and/or the like. The memory 122 can be configured to store, for example, one or more software modules and/or code that can include instructions that can cause the processor 124 to perform one or more processes, functions, and/or the like (e.g., processes, functions, etc. associated with performing the SDRT-PMDS treatment methods described herein). In some implementations, the memory 122 can be physically housed and/or contained in or by the electronic device 120. In other implementations, the memory 122 and/or at least a portion thereof can be operatively coupled to the electronic device 120 and/or at least the processor 124. In such implementations, the memory 122 can be, for example, included in and/or distributed across one or more devices such as, for example, server devices, cloud-based computing devices, network computing devices, and/or the like.

The processor 124 can be a hardware-based integrated circuit (IC) and/or any other suitable processing device configured to run or execute a set of instructions and/or code stored, for example, in the memory 122. For example, the processor 124 can be a general purpose processor, a central processing unit (CPU), an accelerated processing unit (APU), an application specific integrated circuit (ASIC), a network processor, a front end processor, a field programmable gate array (FPGA), a programmable logic array (PLA), and/or the like. The processor 124 can be in communication with the memory 122 via any suitable interconnection, system bus, circuit, and/or the like. As described in further detail herein, the processor 124 can include any number of engines, processing units, cores, etc. configured to execute code, instructions, modules, processes, and/or functions associated with performing the SDRT-PMDS treatment methods described herein.

The communication interface 126 can be any suitable hardware-based device in communication with the processor 124 and the memory 122 and/or any suitable software stored in the memory 122 and executed by the processor 124. In some implementations, the communication interface 126 can be configured to communicate with the network 105 (e.g., any suitable device in communication with the network 105). The communication interface 126 can include one or more wired and/or wireless interfaces, such as, for example, a network interface card (NIC). In some implementations, the NIC can include, for example, one or more Ethernet interfaces, optical carrier (OC) interfaces, asynchronous transfer mode (ATM) interfaces, one or more wireless radios (e.g., a WiFi® radio, a Bluetooth® radio, etc.), and/or the like. As described in further detail herein, in some implementations, the communication interface 126 can be configured to send data to and/or receive data from at least the imaging device 110, the radiation source 115, and/or any other suitable device(s) (e.g., via the network 105).

The memory 122 and/or at least a portion thereof can include and/or can be in communication with one or more data storage structures such as, for example, one or more databases (e.g., the database 125) and/or the like. In some implementations, the database 125 can be configured to store data associated with the SDRT-PMDS treatment methods described herein. The database 125 can be any suitable data storage structure(s) such as, for example, a table, a repository, a relational database, an object-oriented database, an object-relational database, a structured query language (SQL) database, an extensible markup language (XML) database, and/or the like. In some embodiments, the database 125 can be disposed in a housing, rack, and/or other physical structure including at least the memory 122, the processor 124, and/or the communication interface 126. In other embodiments, the electronic device 120 can include and/or can be operably coupled to any number of databases.

Although the electronic device 120 is shown and described with reference to FIG. 1 as being a single device, in other embodiments, the electronic device 120 can be implemented as any suitable number of devices collectively configured to perform as the electronic device 120. For example, the electronic device 120 can include and/or can be collectively formed by any suitable number of server devices or the like. In some embodiments, the electronic device 120 can include and/or can be collectively formed by a client or mobile device (e.g., a smartphone, a tablet, and/or the like) and a server, which can be in communication via the network 105. In some embodiments, the electronic device 120 can be a virtual machine, virtual private server, and/or the like that is executed and/or run as an instance or guest on a physical server or group of servers. In some such embodiments, the electronic device 120 can be stored, run, executed, and/or otherwise implemented in a cloud-computing environment. Such a virtual machine, virtual private server, and/or cloud-based implementation can be similar in at least form and/or function to a physical machine. Thus, the electronic device 120 can be implemented as one or more physical machine(s) or as a virtual machine run on a physical machine.

Although not shown in FIGS. 1 and 2, the electronic device 120 can also include and/or can be in communication with any suitable user interface. For example, in some embodiments, a user interface of the electronic device 120 can be a display such as, for example, a cathode ray tube (CRT) monitor, a liquid crystal display (LCD) monitor, a light emitting diode (LED) monitor, and/or the like. In some instances, the display can be a touch sensitive display or the like (e.g., the touch sensitive display of a smartphone, tablet, wearable device, and/or the like). In some instances, the display can provide the user interface for a software application (e.g., a mobile application, internet web browser, and/or the like) that can allow the user to manipulate the electronic device 120. In other implementations, the user interface can be any other suitable user interface such as a mouse, keyboard, display, and/or the like.

Figure 3:
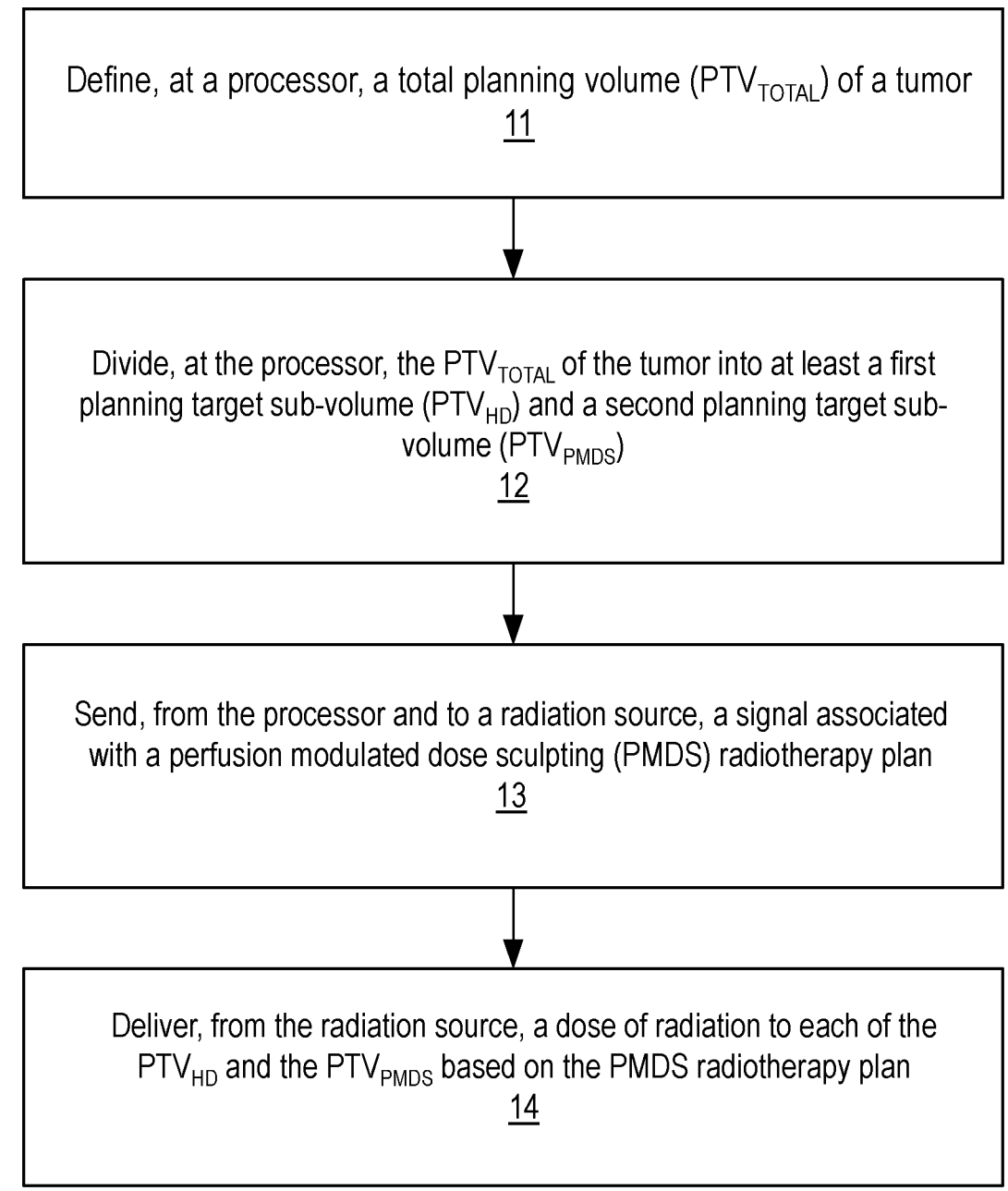
FIG. 3 is a flowchart illustrating a method of treating a tumor in a subject in need thereof, according to an embodiment.

The system 100 can be configured to provide any of the SDRT-PMDS treatment methods described herein. For example, FIG. 3 is a flowchart illustrating a method 10 of treating a tumor in a subject in need thereof. The method 10 can be performed by the system 100 described above with reference to FIGS. 1 and 2 or can be performed by any other suitable system and/or device. In some implementations, the method 10 includes defining, at a processor (e.g., the processor 124), a total planning target volume ($PTV_{TOTAL}$) of the tumor, at 11. The processor can be included in an electronic device such as, for example, the electronic device 120. In some embodiments, the system functions unsupervised. In some embodiments the system is supervised.

In some implementations, the processor can define the $PTV_{TOTAL}$ can be based, at least in part on one or more images of the tumor and/or the tissue or organs surrounding the tumor. For example, in some embodiments, an imaging device (e.g., the imaging device 110) can be configured to capture one or more images of at least the tumor. The imaging device, for example, can be a machine configured to perform a CT scan, an MRI scan, a PET scan, ultrasonic imaging, and/or any other suitable imaging modality. The imaging can be performed pre-operatively (e.g., prior to providing the SDRT-PMDS treatment) or during the SDRT-PMDS treatment (e.g., in real-time or substantially in real-time). In some embodiments, an electronic device that includes the processor can receive the one or more images from the imaging device and can define a composite and/or model of the tumor based on the one or more images. For example, in some instances, the electronic device can be configured to generate and/or define a 3D model of the tumor based at least in part on the one or more images. In some instances, the 3D model can further include at least a portion of an organ at risk (OAR) that is in contact with the tumor or that is within a threshold distance of the tumor associated with an undesirable level of radiation being delivered to the OAR during treatment, as described in detail above. In some implementations, the $PTV_{TOTAL}$ can be based on data other than data associated with the one or more images.

As mentioned above, in some implementations, an imaging device can be used to perform scans and/or to otherwise capture images of the tumor and/or the subject prior to the radiotherapy being provided to the subject. These images can be used to define the $PTV_{TOTAL}$ and/or one or more treatment options prior to providing the radiotherapy. In some such implementations, the imaging device (or a different imaging device) can be used to confirm the characteristics of the tumor at the time of the radiotherapy still correspond to the $PTV_{TOTAL}$ defined using the previous scans and/or images. In other words, in some instances, the system can be configured to define a radiotherapy (SDRT-PMDS) treatment plan prior to providing the SDRT-PMDS treatment. In some implementations, data associated with pre-planned treatments, treatment characteristics, treatment profiles, and/or the like can be stored in a database (e.g., the database 125) and subsequently can be retrieved during treatment.

The processor divides the virtual $PTV_{TOTAL}$ of the tumor into at least a first virtual planning target sub-volume ($PTV_{HD}$) and a second virtual planning target sub-volume ($PTV_{PMDS}$), at 12. As described in detail above, the $PTV_{HD}$ can be a sub-volume of the tumor in which it is desirable to deliver a high dosage of radiation and the $PTV_{PMDS}$ can be a sub-volume of the tumor in which it is desirable to deliver a dosage that is less than the dosage delivered to the $PTV_{HD}$. In some implementations, the $PTV_{TOTAL}$ can be divided into the $PTV_{HD}$ and the $PTV_{PMDS}$ based at least in part on a user input. For example, in some instances, a user (e.g., a doctor) can provide an input into the electronic device that is indicative of one or more instructions associated with how and/or where to divide the $PTV_{TOTAL}$. As a specific example, in some instances, the electronic device can be configured to present the 3D model of the tumor (e.g., a 3D model of $PTV_{TOTAL}$) on a display of the electronic device. In such instances, the user can, for example, select, draw, and/or otherwise indicate on the 3D model a volume corresponding to the $PTV_{HD}$ and a volume corresponding to the $PTV_{PMDS}$. As such, the processor can divide the $PTV_{TOTAL}$ in accordance with the input provided by the user. In other instances, the processor can execute one or more instructions or code stored, for example, in the memory of the electronic device that can include a set of predefined rules and/or conditions that dictate and/or control the division of the $PTV_{TOTAL}$ into any desirable number of sub-volumes. In this example, the predefined rules and/or conditions can dictate the division of the $PTV_{TOTAL}$ into $PTV_{HD}$ and $PTV_{PMDS}$. Whether the result of user input or the execution of a set of predefined rules and/or conditions, in some implementations, the processor can be configured to define a SDRT-PMDS radiotherapy plan that defines at least one characteristic of the radiotherapy to be delivered to the $PTV_{TOTAL}$ (collectively formed by the $PTV_{HD}$ and the $PTV_{PMDS}$). In some implementations, the processor can be configured to define a SDRT-PMDS radiotherapy plan that defines all or substantially all of the characteristics of the radiotherapy to be delivered to the tumor.

The processor sends, to a radiation source, a signal associated with the SDRT-PMDS radiotherapy plan, at 13. In some implementations, for example, the signal can be indicative of an instruction to provide radiotherapy to the tumor in accordance with the SDRT-PMDS radiotherapy plan. Accordingly, the radiation source delivers a dose of radiation to each of the $PTV_{HD}$ and the $PTV_{PMDS}$ based on the SDRT-PMDS radiotherapy plan, at 14.

For example, in some implementations, the processor can the SDRT-PMDS radiotherapy plan that defines the dosage, dosage range, or dosage gradient to be delivered to each of the $PTV_{HD}$ and the $PTV_{PMDS}$. For example, in some instances, the dosage to be delivered to the $PTV_{HD}$ of the tumor can be a relatively high dosage of radiation such as an ablative dosage, as described in detail above. In some instances, the dosage to be delivered to the $PTV_{PMDS}$ of the tumor can be a relatively low dosage of radiation and/or can be a dosage gradient that is configured to be below a threshold level of radiation at areas and/or volume of the tumor that are in contact with, adjacent to, and/or otherwise near the OAR. As an example, in some instances, the dose of radiation covering 95% of the $PTV_{PMDS}$ ($PTV_{PMDS}$-D95) can be lower than the dose of radiation covering 95% of the $PTV_{HD}$ ($PTV_{HD}$-D95) and lower than the dose of radiation covering 95% of the total PTV ($PTV_{TOTAL}$-D95) that is desired to treat the tumor. In some instances, the dosage and/or dosage gradient to be delivered to the $PTV_{PMDS}$ and/or to the $PTV_{PMDS}$-D95 can be based at least in part on a sensitivity of the OAR. In some instances, the dosage and/or characteristics associated with the dosage delivered to each of the $PTV_{HD}$ and the $PTV_{PMDS}$ can be based on or in accordance with any of those described in detail above.

While the system 100 is described above as being configured to perform a SDRT-PMDS treatment method such as, for example, the method 10, in some implementations, the system 100 can be configured to perform any suitable functions associated with and/or in addition to a SDRT-PMDS treatment method. For example, in some embodiments, the electronic device 120 and/or the processor 124 thereof can be configured to define data associated with treatment parameters, profiles, regimens, plans, profiles, etc. based on one or more characteristics associated with a tumor, an OAR, and/or the like. In some implementations, this data can be stored in the database 125 and retrieved when defining a new treatment plan and/or when providing a SDRT-PMDS treatment. In some implementations, the data can be used to determine whether a given tumor is suitable for any of the SDRT-PMDS treatment methods described herein. Moreover, in some implementations, the database 125 and/or memory 122 of the electronic device 120 can be configured to store historical data associated with proposed treatment plans, treatment outcomes, treatment success rates, and/or the like that can be used, for example, to provide outcome predictions and/or anticipated recovery probabilities. For example, in some implementations the processor 124 can be configured to define a $PTV_{TOTAL}$ for a given tumor and can compare data associated with the $PTV_{TOTAL}$ to historical data stored in the database 125 that is associated with the $PTV_{TOTAL}$ for other (e.g., similar) tumors. As such, the system 100 can be configured to provide treatment recommendations and/or can be configured to predict treatment outcomes associated with treating any given tumor, any given type of tumor, any given set of characteristics associated with a tumor, and/or the like.

Some embodiments described herein relate to a computer storage product with a non-transitory computer-readable medium (e.g., memories or one or more memories) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, an FPGA, an ASIC, and/or the like. Software modules (executed on hardware) can be expressed in a variety of software languages (e.g., computer code), including C, C++, Java™, Ruby, Visual Basic™, Python™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools, and/or combinations thereof (e.g., Python™). Additional examples of computer code include, but are not limited to, control signals, encrypted code, and compressed code.

Clinical Indications

In particular embodiments, the methods described herein can be used in the treatment of various types of solid tumors. Examples of solid tumors include, but are not limited to tumors of the following organs: the skin, breast, brain, cervix, testis, heart, lung, gastrointestinal tract, genitourinary tract, liver, bone, nervous system, reproductive system, and adrenal glands.

Malignant tumors which can be treated by methods described herein can be used in the treatment of cancer, including carcinomas, lymphomas, blastomas, sarcomas (including liposarcomas, osteogenic sarcomas, angiosarcomas, endotheliosarcomas, leiomyosarcomas, chordomas, lymphangiosarcomas, lymphangioendotheliosarcomas, rhabdomyosarcomas, fibrosarcomas, myxosarcomas, chondrosarcomas), neuroendocrine tumors, mesotheliomas, synoviomas, schwannomas, meningiomas, adenocarcinomas, and melanomas. Additional tumors which can be treated by methods described herein include without limitation adrenal tumors (e.g., adrenocortical carcinoma), anal, bile duct, bladder, bone tumors (e.g., Ewing's sarcoma, osteosarcoma, malignant fibrous histiocytoma), brain/CNS tumors (e.g., astrocytoma, glioma, glioblastoma), childhood tumors (e.g., atypical teratoid/rhabdoid tumor, germ cell tumor, embryonal tumor, ependymoma), breast tumors (including without limitation ductal carcinoma in situ carcinoma), cervical tumors, colon/rectum tumors, endometrial tumors, esophageal tumors, eye tumors (e.g., melanoma, retinoblastoma), gallbladder tumors, gastrointestinal tumors, kidney tumors (e.g., renal cell, Wilms' tumor), heart tumors, head and neck tumors, laryngeal and hypopharyngeal tumors, liver tumors, lung tumors, oral tumors (e.g., lip, mouth, salivary gland), mesothelioma, nasopharyngeal tumors, neuroblastomas, ovarian tumors, pancreatic tumors, peritoneal tumors, pituitary tumors, prostate tumors, rhabdomyosarcomas, salivary gland tumors, sarcomas (e.g., Kaposi's sarcoma), skin tumors (e.g., squamous cell carcinoma, basal cell carcinoma, melanoma), small intestine tumors, stomach tumors, soft tissue sarcomas (such as fibrosarcoma), testicular tumors, thymic tumors, thyroid tumors, parathyroid tumors, uterine tumors (including without limitation endometrial, fallopian tube), and vaginal tumors and the metastases thereof. In some embodiments, the tumor is selected from the group consisting of breast, lung, GI tract, skin, and soft tissue tumors.

More particular examples of cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, lymphoma, multiple myeloma, Waldenstrom's macroglobulinemia, myelodysplastic disease, heavy chain disease, neuroendocrine tumors, Schwannoma, and other carcinomas, as well as head and neck cancer.

It is to be understood that the description above as well as the examples that follow are intended to illustrate, and not limit, the scope of the invention. Other aspects, advantages and modifications within the scope of the invention will be apparent to those skilled in the art to which the invention pertains.

EXAMPLES

Example 1: Perfusion Modulated Tumor Dose Sculpting (PMDS) to Match Serial Organ Constraints in Radioablation by Single Dose Radiotherapy Materials and Methods Patients: Studies described herein employed a database of a recently published clinical phase II study of 175 consecutive patients with oligometastatic (OM) disease undergoing radioablation (Greco et al., Phenotype-Oriented Ablation of Oligometastatic Cancer with Single Dose Radiation Therapy. Int J Radiat Oncol Biol Phys. 2019). Studies described herein comprised a total of 577 lesions treated with an ablative intent, as long as the patient maintained an oligometastatic status (i.e., an absence of widespread dissemination defined as ≥6 concomitant lesions on follow-up PET/CT scanning). Observations were restricted to clinical and therapeutic variables affecting local tumor control.

Treatment planning and delivery: All lesions were planned for radioablation with CT and [$^{18}$F]fluorodeoxyglucose positron emission tomography scans ([$^{18}$F]FDG-PET/CT), with the exception of prostate OM lesions which were also planned with the PET tracer [$^{68}$Ga]Prostate Specific Membrane Antigen (PSMA-PET/CT). Co-registered PET/CT images were used to outline the gross tumor volume (GTV) and clinical tumor volume (CTV). 4D-CT scanning was employed in mobile lesions to design an internal target volume (ITV) added to the GTV to compensate for respiratory target motion according to the RTOG 0236 guidelines. The PTV was obtained with a 3 mm isotropic margin added to the GTV or ITV. OARs were expanded with isotropic margins to produce planning risk volumes (PRVs) as indicated by ICRU Report 83 (DeLuca et al., ICRU Report 83: Prescribing, recording, and reporting photon-beam intensity-modulated radiation therapy (IMRT) Journal of the ICRU 2010; 10(1):1-93). Treatment planning was carried out with the Eclipse software (Varian Medical Systems, Palo Alto, CA) using 2-4 co-planar VMAT 6 MV or 10 MV FFF beams. The beam orientations were chosen to minimize OAR involvement. Plans were calculated using heterogeneity corrections to ensure appropriate dose calculation.

Dose Sculpting: Dose sculpting was performed using VMAT technology. Dose fall-off can be engineered regardless of beam energy, with ~30% and ~50% reductions achievable within 5 mm and 10 mm, respectively, by deploying ≥3 VMAT arcs, with some dependence on target volume (Brito et al., Modeling the target dose fall-off in IMRT and VMAT planning techniques for cervical SBRT. Med Dosim. 2018; 43(1):1-10). In extreme cases, up to 12%/mm dose fall-off can be achieved.

Treatment Protocols: 3 treatment plans were utilized in the studies described herein: a baseline SDRT treatment protocol, an SDRT-PMDS protocol, and a hypofractionated SBRT protocol. All plans underwent strict QA testing with a pretreatment dry-run using ArcCHECK (Sun Nuclear Corp., Melbourne, FL). Gamma analysis values at the 3%/3 mm≥90% were considered acceptable. The EDGE/TrueBeam STx platforms (Varian Medical Systems, Palo Alto, CA) equipped with an ExactCouch (6-degrees of freedom, 6 DoF) system were used for treatment delivery. Treatment was started following accurate CBCT matching and target realignment via the 6 DoF couch.

(a) Baseline SDRT Protocol: The planning objectives of the baseline protocol included compliance to all institutional OAR dose/volume constraints and plan normalization such that at least 95% of the PTV received 100% of the prescription dose of 24 Gy (PTV D95≥24 Gy) with an isotropic dose gradient around the PTV.

(b) SDRT-PMDS Protocol: When the PTV penumbra did not comply with an adjacent serial organ dose/volume constraint, the SDRT-PMDS dose-sculpting technique was employed at the discretion of the treating physician, reducing the dose coverage in the PMDS sub-volume ($PTV_{PMDS}$) as required to comply with the OAR constraints. SDRT-PMDS technique divided the total PTV into at least 2 PTV sub-volumes: a dominant PTV sub-volume (PTV high dose or $PTV_{HD}$) and a minor PTV sub-volume wherein the dose was reduced to comply with the adjacent OAR dose/volume constraints ($PTV_{PMDS}$).

(c) Hypofractionated SBRT protocol: When neither baseline SDRT treatment plan nor the SDRT-PMDS technique complied with the serial organ dose/volume constraints, treatment planning was diverted to a non-toxic 3×9 Gy hypofractionated SBRT protocol.

Endpoints: Local tumor response was assessed according to the PERCIST (PET Response in Solid Tumors) guidelines, using PET/CT scans, at 3 and 6 months post-treatment, and at 6 months intervals thereafter. Actuarial local relapse-free survival (LRFS) and cumulative incidence of local recurrences of treated lesions were calculated based on events occurring for each lesion independently, and calculated from the date of the radio-ablative exposure. Acute and late toxicities were scored based on the NIH Common Terminology Criteria for Adverse Events Guidelines, version 4.0.

Statistical analysis: Time to local failure was calculated from the day of treatment. GTV, baseline standard uptake value ($SUV_{MAX}$), OM lesion histology, target site, use of systemic therapy before treatment or post-ablation, the PTV-D95, the near minimum dose to the entire PTV (PTV-D99), the mean dose to the PTV and its standard deviation, the volume of the PTV covered by the prescription dose (V100), and the homogeneity index (HI) were tested as variables effecting local control. Death without recurrence was regarded as a competing risk and the Gray test was used to calculate the cumulative incidence of failures. Actuarial analysis was calculated using the Kaplan-Meier method, and univariate analysis was performed to compare the association of relevant variables using the Cox proportional hazards regression method. Hazard ratio (HR), 95% confidence intervals (CI), and chi-square scores statistical computations were performed using the GraphPad Prism 7.0 software (Prism Inc, Reston, VA).

Results—Patients and Lesions Treated by Radioablation

Lesion characteristics are shown in Table 2. A total of 436 lesions were treated with an SDRT, of which 149 (34%) lesions were planned with the SDRT-PMDS technique, defined as a PTV-D99<23 Gy. In addition, 141 OM lesions were treated with 3×9 Gy SBRT, because a 24 Gy SDRT treatment plan (without or with a PMDS component) in compliance with the dose/volume constraints of adjacent serial OARs could not be generated. Hence, in 290/577 (50%) of the lesions, treatment planning and delivery were primarily driven by a requirement to comply with serial OAR dose/volume restrictions

TABLE 2

Lesion characteristics

|  |  | All (N = 436) | LC[#] (N = 403) | LR[##] (N = 33) |
|---|---|---|---|---|
| Histology | Prostate | 117 (27) | 114 (28) | 3 (9) |
|  | NSCLC | 76 (18) | 66 (16) | 10 (30) |
|  | Colon cancer | 67 (15) | 55 (14) | 12 (37) |
|  | Breast | 56 (13) | 54 (14) | 2 (6) |
|  | Renal cell cancer | 20 (5) | 20 (5) |  |
|  | Ovarian | 14 (3) | 14 (3) |  |
|  | Sarcoma | 13 (3) | 13 (3) |  |
|  | Pancreatic | 10 (2) | 10 (2) |  |
|  | Bladder | 11 (3) | 8 (2) | 3 (9) |
|  | Melanoma | 4 (1) | 4 (1) |  |
|  | Other histology | 48 (12) | 45 (12) | 3 (9) |
| Lesion site | Bone | 147 (34) | 140 (35) | 7 (21) |
|  | Lymph-nodes | 125 (28) | 116 (29) | 9 (27) |
|  | Lung | 90 (21) | 83 (20) | 7 (21) |
|  | Liver | 35 (8) | 32 (8) | 3 (9) |
|  | Soft Tissues | 39 (9) | 32 (8) | 7 (21) |
| Systemic therapy | Yes | 362 (83) | 330 (82) | 32 (97) |
|  | No | 74 (17) | 73 (18) | 1 (3) |
| Pre-SDRT systemic Tx | Yes | 311 (71) | 284 (65) | 27 (82) |
|  | No | 125 (29) | 119 (35) | 6 (18) |
| Post-SDRT systemic Tx | Yes | 241(50) | 222 (51) | 19 (58) |
|  | No | 195 (50) | 181 (49) | 14 (42) |

[#]LC = Local control
[##]LR = Local relapse

Results—Radioablation of OM Lesions with 24 Gy SDRT

Figure 4:
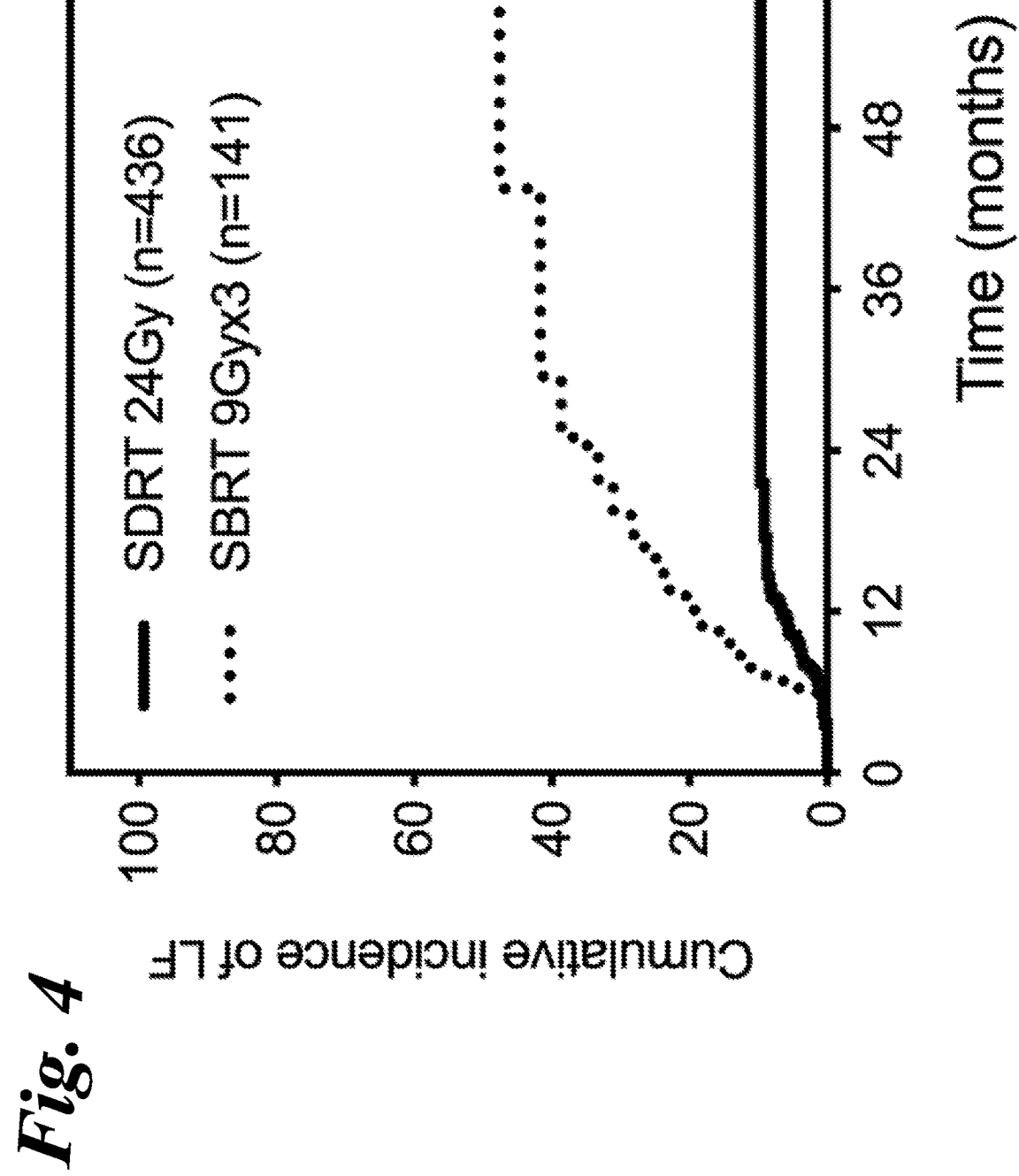
FIG. 4 illustrates cumulative incidence of local failure of traditional 24 Gy SDRT-treated vs. 3×9 Gy SBRT-treated lesions.
Figure 5B:
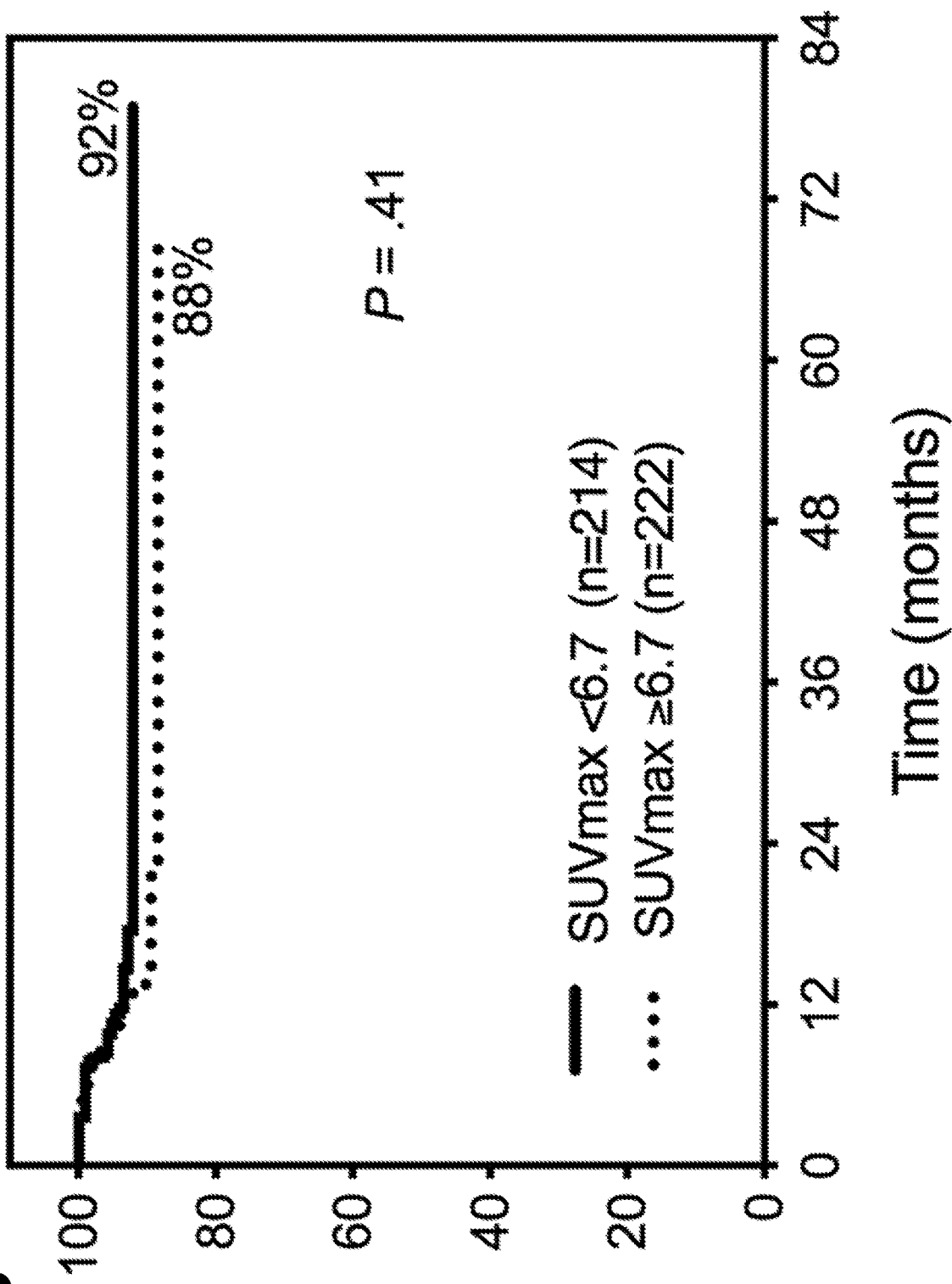
Figure 6A:
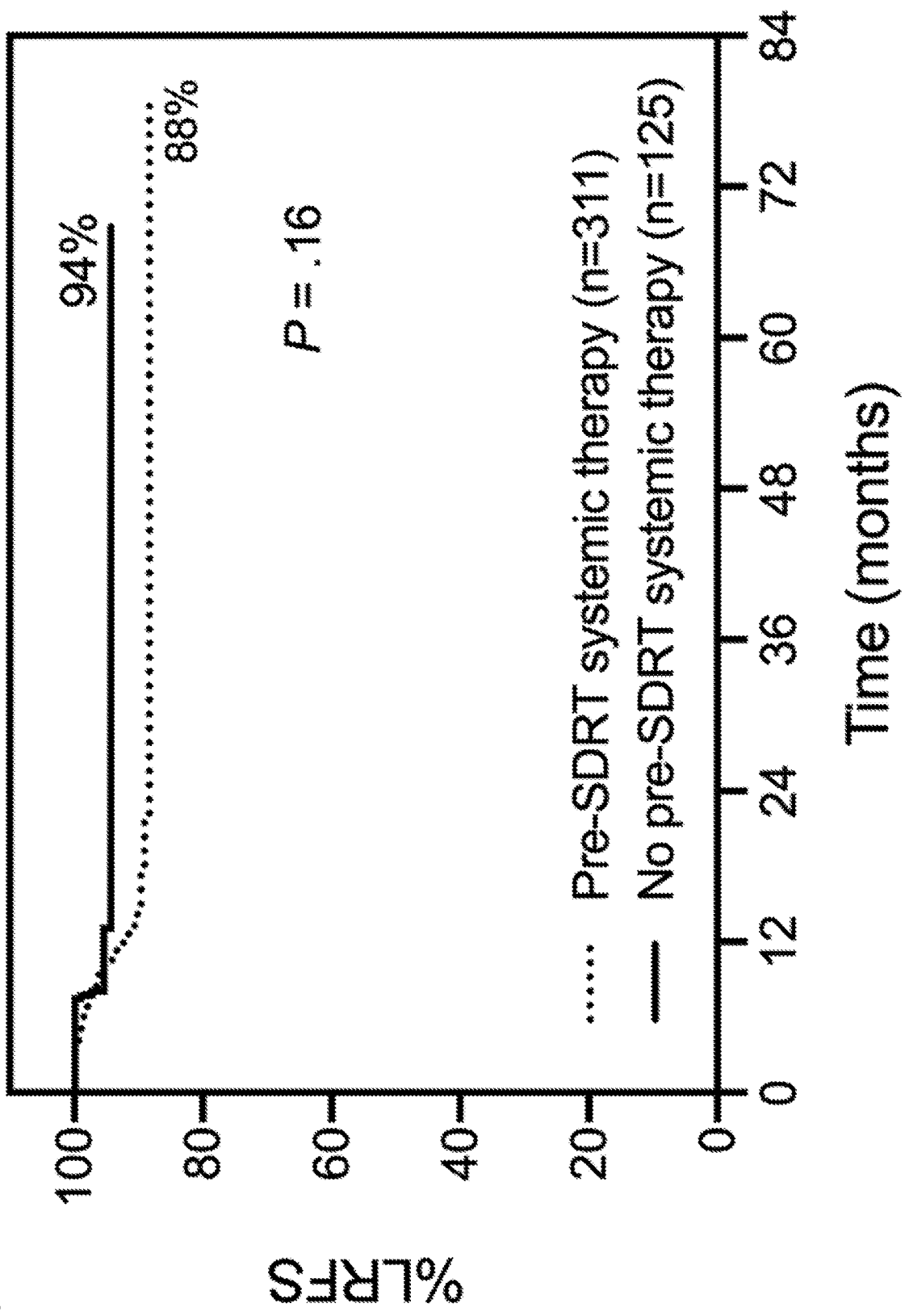
FIG. 6A-FIG. 6B illustrate the effect of systemic (chemotherapy or hormonal) therapy on LRFS of OM lesions treated with 24 Gy SDRT.
Figure 6B:
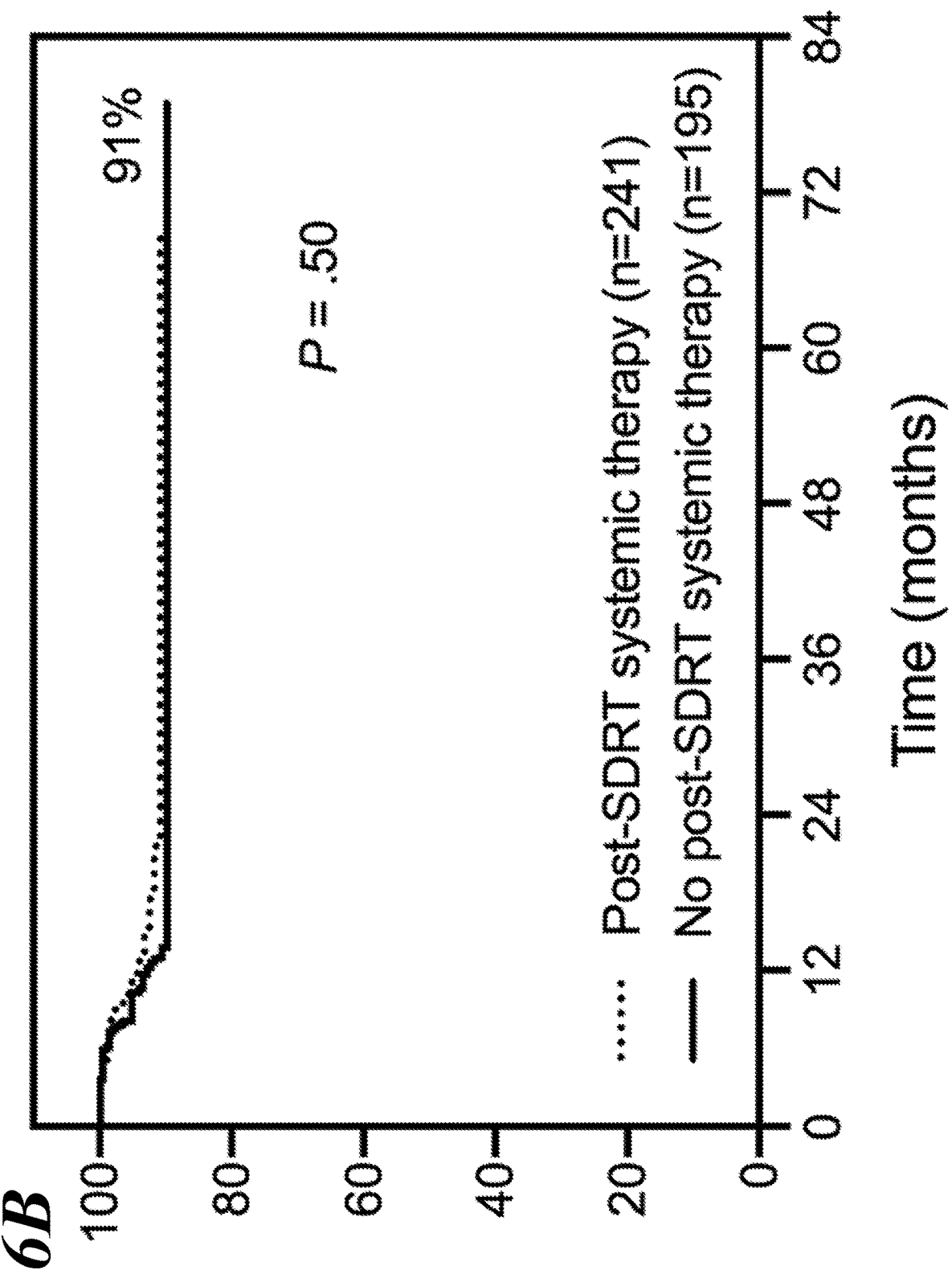

As shown in FIG. 4, the actuarial cumulative incidence of local relapse of lesions treated with 24 Gy SDRT and SDRT-PMDS combined was 900 at 5 years (a total of 33/436 LRs occurring within 6-24 months). In contrast, a total of 49/141 LRs were observed in the 3×9 Gy hypofractionated SBRT group, yielding an actuarial cumulative 5-year local relapse rate of 4800 (FIG. 4; P<0.0001). Univariate analyses of variables affecting LRFS post SDRT 24 Gy treatment showed that pre-ablation GTV was not associated with a risk of LR when binary partitioning dichotomization using median GTV (4.2 $cm^3$) as a cut-off point (FIG. 5A; actuarial 5-years LRFS of 91% and 90%, respectively, P=0.40). Similarly, there was no correlation of pre-ablation baseline PET $SUV_{MAX}$ with dichotomized at the median $SUV_{MAX}$ value of 6.7 (FIG. 5B; P=0.72). OM target site did not have a statistically significant correlation with LRFS (P=0.24, not shown). In addition, systemic therapy did not impact LRFS, given either before SDRT (FIG. 6A, P=0.16) or as adjuvant post-SDRT (FIG. 6B, P=0.38). Finally, GM lesion histology did not impact LRFS (P=0.06; not shown). Radioablation with SDRT was not associated in this series with grade ≥2 acute or late toxicities. A total of 55/175 patients (35%) experienced Grade 1 acute toxicity not requiring symptomatic therapy. Follow-up for the entire study cohort ranged between 3.0 and 78.9 (median 37.7) months.

Results—Effect of SDRT-PMDS on Local Control

Figure 7:
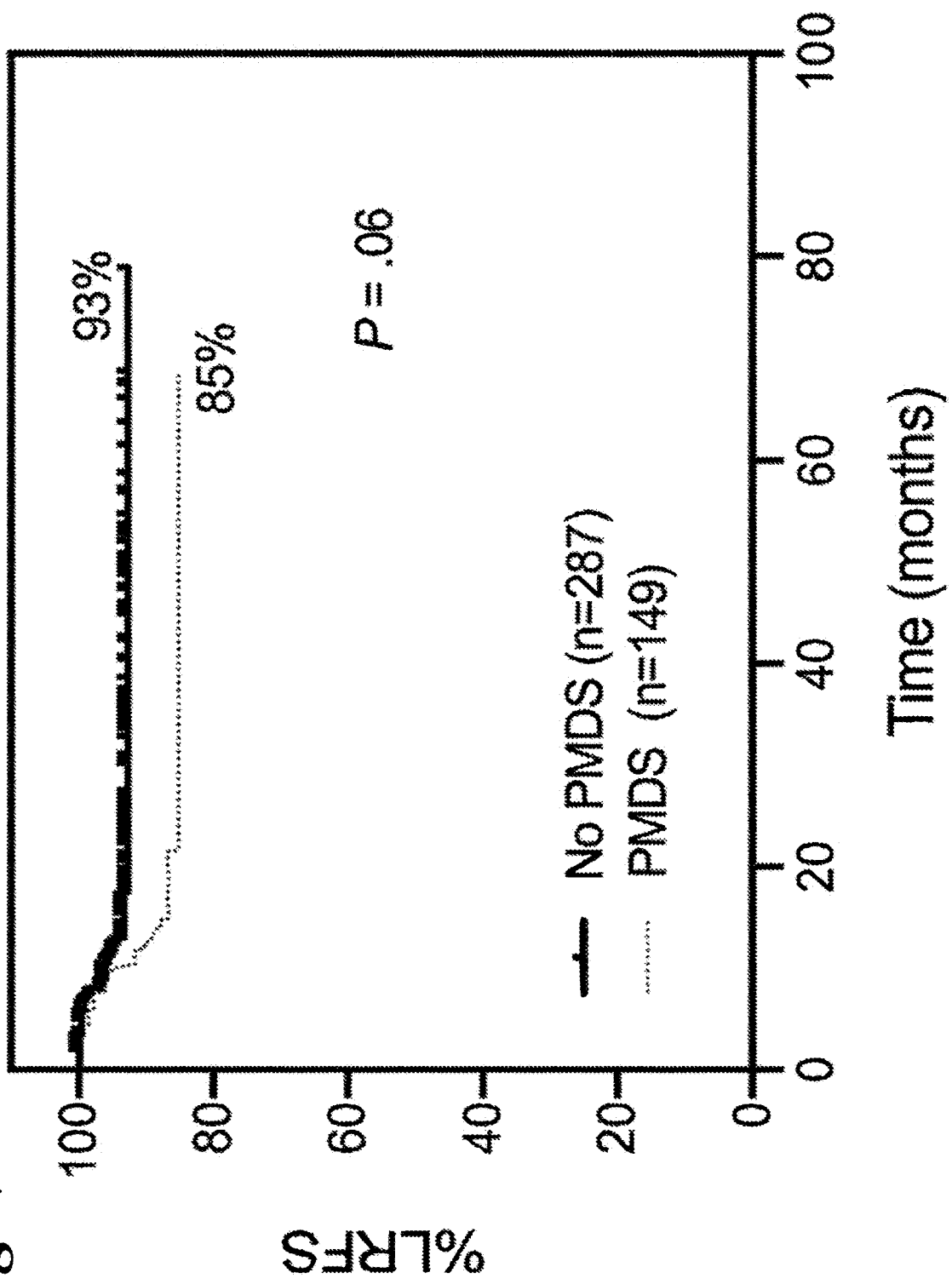
FIG. 7 illustrates LRFS of OM lesions treated with 24 Gy SDRT without employing the perfusion-mediated dose sculpting (PMDS) compared with LRFS of lesions employing the SDRT-PMDS technique to comply with the tolerance of an adjacent critical normal organ at risk (OAR).

As shown in Table 3A, 287/436 (66%) SDRT-treated lesions were treated by 24 Gy SDRT alone (no PMDS), serving as a baseline control group for evaluation of the SDRT-PMDS group. The PTV-D99 for these 24 Gy SDRT-treated lesions was ≥23 Gy (Table 3A). Local relapses occurred in the 24 Gy SDRT-treated category in 17/287 lesions and were associated with technical or machine uncertainties, yielding an actuarial 5-years LRFS rate of 93% (Table 3A and FIG. 7). SDRT-PMDS was employed in 149 (34%) lesions, associated with a reduction of the whole-tumor PTV-D99 to <23 Gy (Table 3B). Local relapses occurred in 16/149 in the SDRT-PMDS lesions (Table 3A), yielding an actuarial 5-year LRFS of 85%, boarder-line statistically different from the outcome in the 24 Gy SDRT alone group (P=0.06; FIG. 7).

TABLE 3A

Treatment Characteristics and Outcomes—SDRT 24 Gy, No PMDS

|  | # Lesions | PTV-D99 (Gy) | | |
|---|---|---|---|---|
|  |  | Mean | Median | Range |
| Total | 287 | 24.2 | 24.1 | 23.4-26.3 |
| Local Control | 270/287 (94%) | 24.2 | 24.1 | 23.4-26.3 |
| Relapses | 17/287 (6%) | 24.2 | 24 | 24-24.4 |

TABLE 3B

Treatment Characteristics and Outcomes—PMDS

|  | # Lesions | PTV-D99 (Gy) | | |
|---|---|---|---|---|
|  |  | Mean | Median | Range |
| Total | 149 | 17.2 | 17.8 | 8.30-22.5 |
| Local Control | 133/149 (89%) | 17.3 | 17.9 | 8.30-22.5 |
| Relapses | 16/149 (11%) | 16.9 | 17.9 | 8.30-22.1 |

Figure 8A:
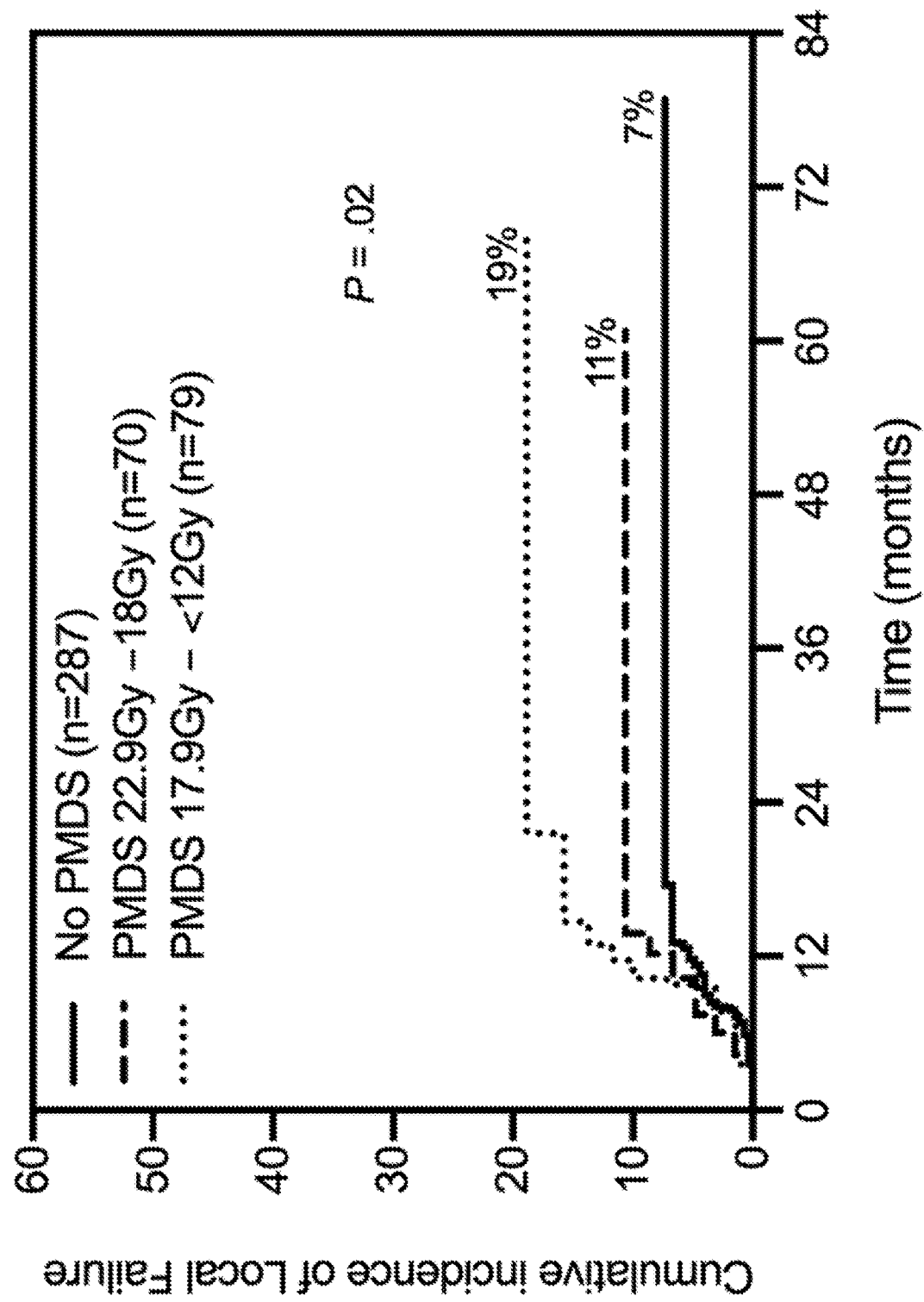
FIG. 8A-FIG. 8B illustrate the cumulative incidence of local failure following 24 Gy SDRT alone compared with SDRT-PMDS treated OM tumors. The prescribed $PTV_{HD}$ for lesions treated with SDRT-PMDS was 24 Gy.

Further analysis of the SDRT-PMDS group showed two dose-sculpted subgroups, one comprising 70 lesions undergoing moderate dose sculpting ($PTV_{PMDS}$ D99=22.5 Gy-18 Gy), and a second group comprising 79 lesions undergoing a more intensive dose sculpting ($PTV_{PMDS}$ D99=17.9 Gy-≤12 Gy) (Table 4). FIG. 8A shows that the actuarial cumulative incidence of LR in the PMDS 22.5 Gy-18 Gy group was 11%, statistically not different from the LR rate of 6% observed in lesions treated with 24 Gy SDRT alone (P=0.36). In contrast, the PMDS 17.9 Gy-≤12 Gy group yielded a significantly higher actuarial cumulative LR incidence of 19% (FIG. 8A; P=0.02).

TABLE 4

Moderate vs. Intensive PMDS dose sculpting

|  | # Lesions | PTV-D99 (Gy) | | |
|---|---|---|---|---|
|  |  | Mean | Median | Range |
| Moderate PMDS dose sculpting | | | | |
| Total | 70 | 20.5 | 20.6 | 18-22.5 |
| Local Control | 64 (91%) | 20.6 | 20.6 | 18-22.5 |
| Relapses | 6 (9%) | 20.2 | 19.8 | 18.5-22.1 |
| Intensive PMDS dose sculpting | | | | |
| Total | 79 | 13.7 | 14.7 | 8.3-17.9 |
| Local Control | 69 (87%) | 13.6 | 14.7 | 8.3-18 |
| Relapses | 10 (13%) | 14.6 | 15.4 | 8.3-17.9 |

Figure 8B:
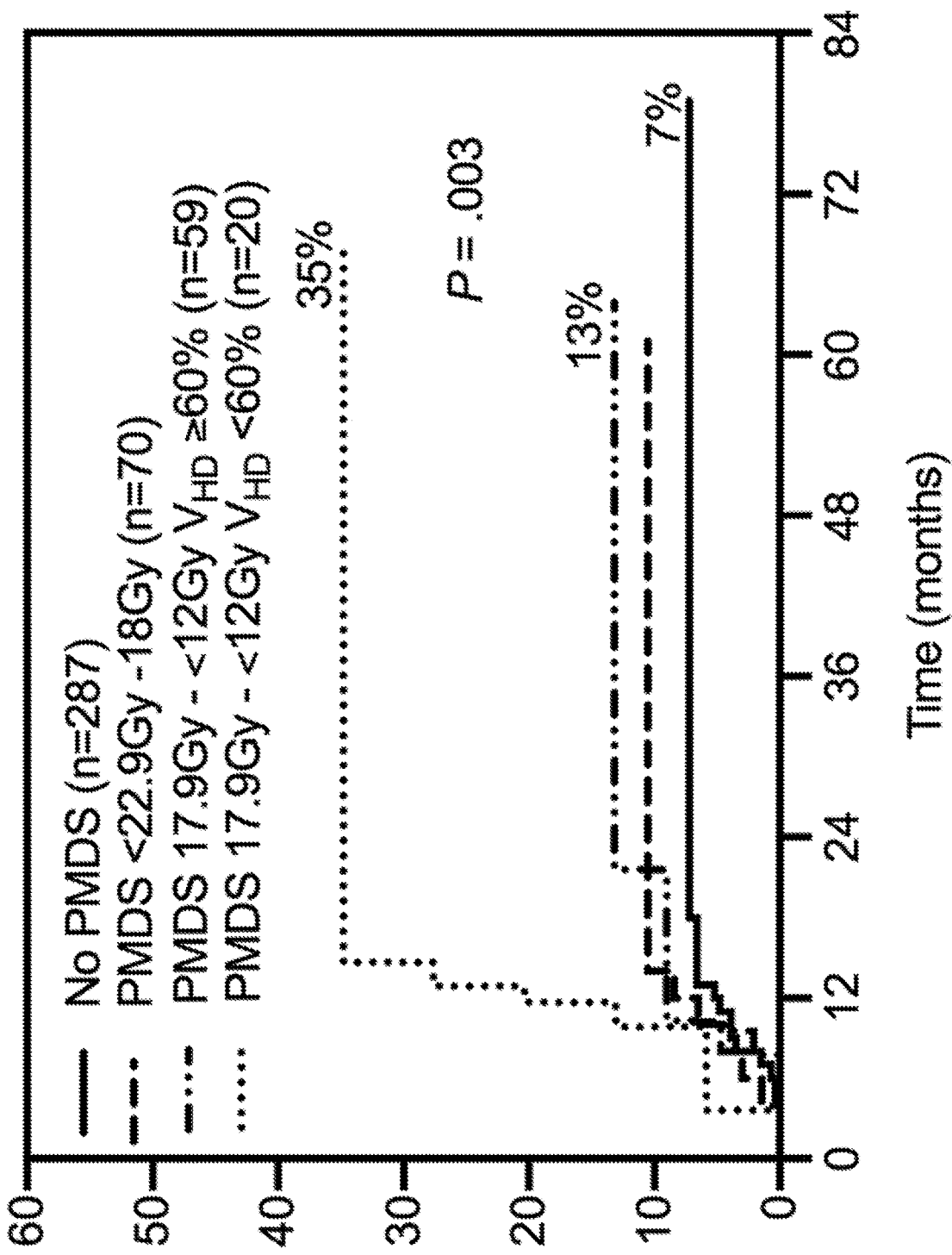

However, as shown in FIG. 8B and Table 5, LR incidence in the intensive PMDS dose sculpting group (PTV-D99=17.9 Gy-≤12 Gy) was dependent on the $PTV_{HD}$ volume treated to the 24 Gy isodose (V100). When the $PTV_{HD}$ V100 was ≥60% of the whole PTV, the actuarial cumulative incidence of LR was 13% and was not significantly different from the LR incidence of the control group of lesions treated with 24 Gy SDRT alone (FIG. 8, P=0.11). In contrast, when the $PTV_{HD}$ V100 was ≤60% of the whole PTV, the actuarial cumulative incidence of LR nearly doubled to a rate of 1355 (FIG. 8, P=0.003).

TABLE 5

Impact of PTV V100

|  | # Lesions | Mean | Median | Range |
|---|---|---|---|---|
| $PTV_{HD}$ V100 ≥ 60% PTV | | | | |
| Total | 59 | 15.2 | 14.4 | 8.3-17.9 |
| Local Control | 54 (92%) | 14.3 | 15.2 | 8.3-17.9 |
| Relapses | 5 (8%) | 14.8 | 15.8 | 8.3-17.9 |
| $PTV_{HD}$ V100 < 60% PTV | | | | |
| Total | 20 | 10.5 | 11.8 | 8.4-17.9 |
| Local Control | 15 (75%) | 10.9 | 10.1 | 8.4-17.3 |
| Relapses | 5 (25%) | 14.6 | 15.1 | 10.3-15.1 |

Results—SDRT-PMDS Case Report

Figure 9A:
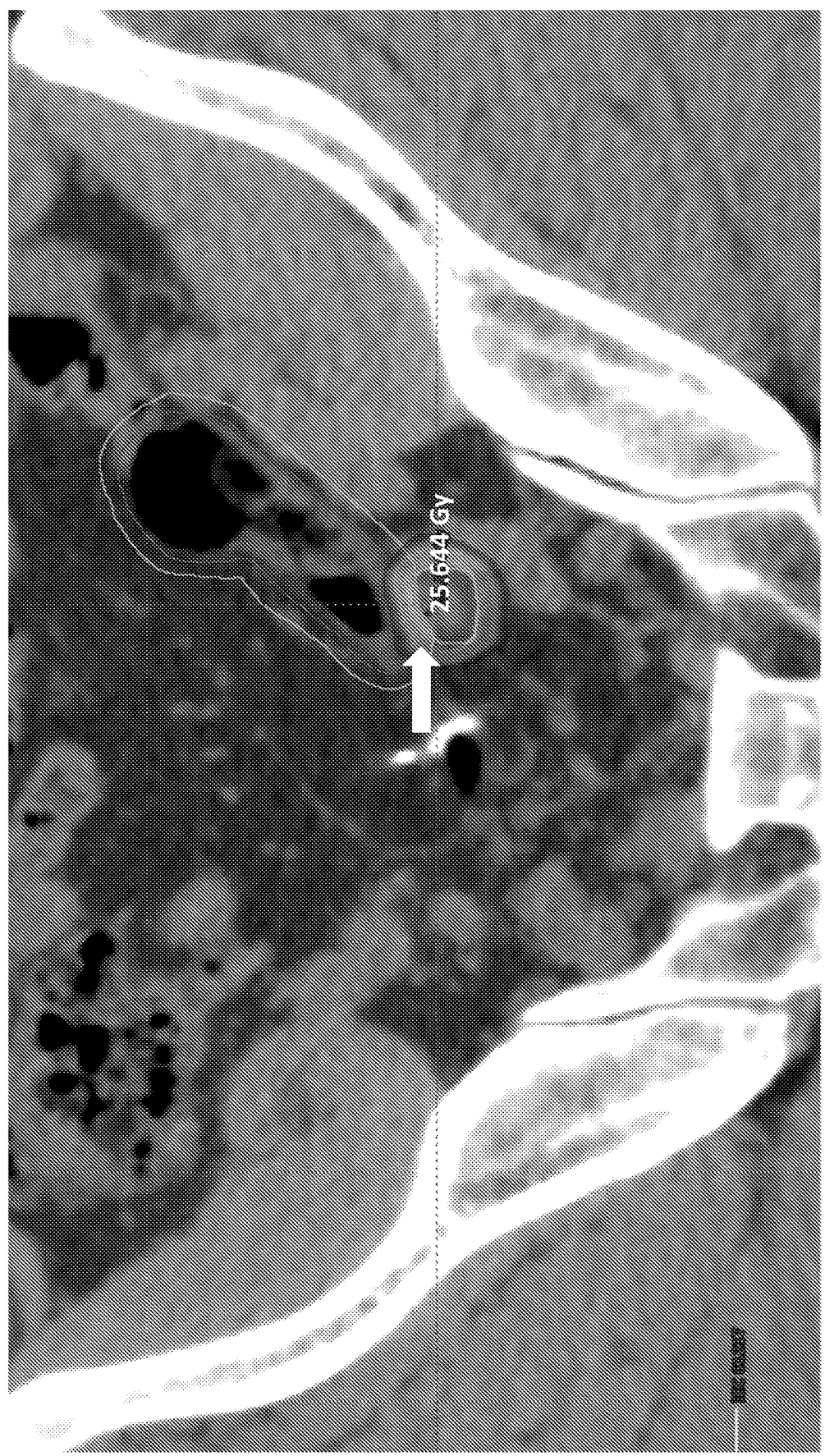
FIG. 9A-FIG. 9C illustrates SDRT-PMDS of a metastatic pelvic lymph-node. The PTV was obtained with an isotropic 3 mm expansion from the FDG-PET derived GTV. The whole PTV measures 2.2 cm$^3$.
Figure 9B:
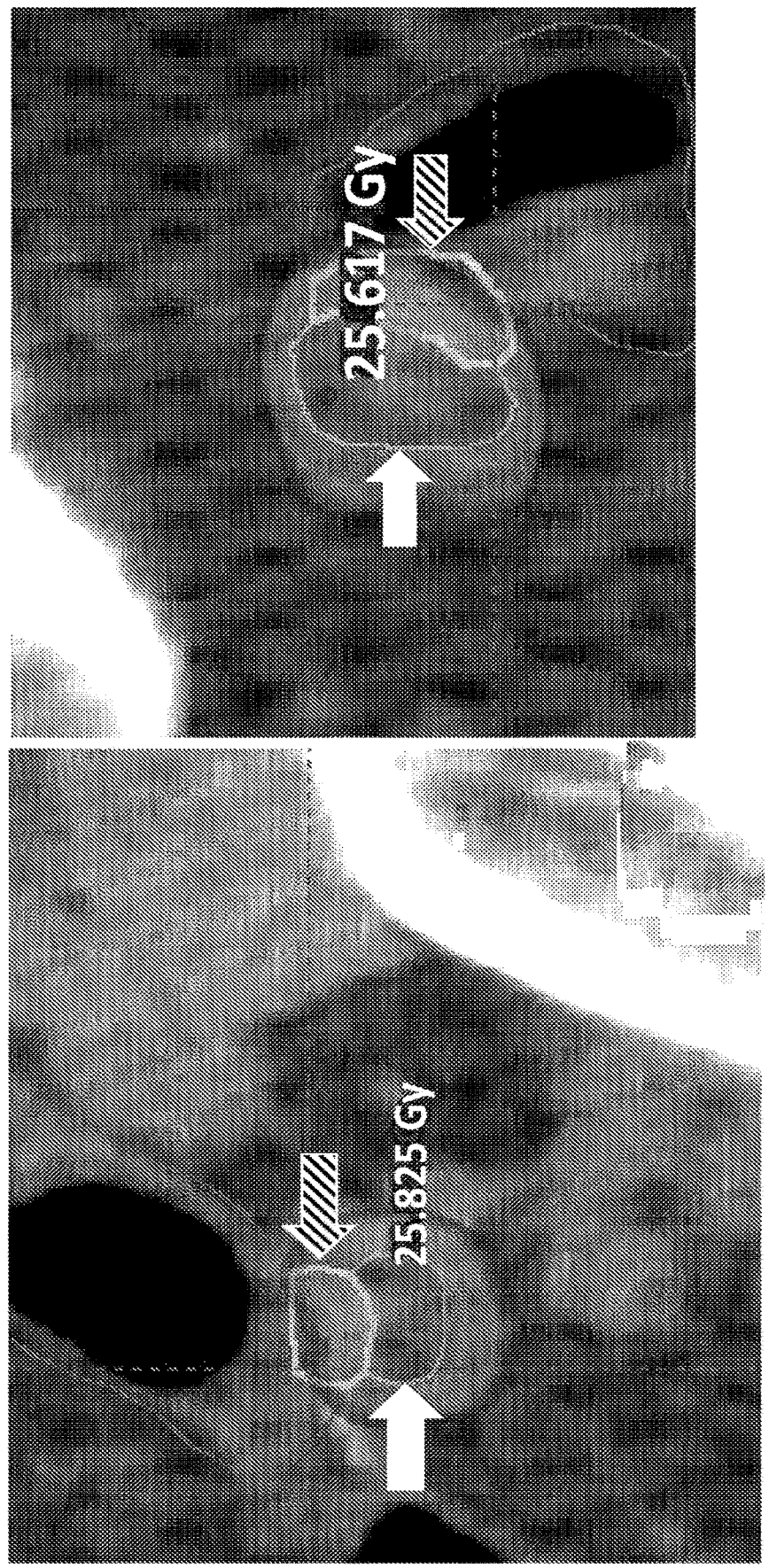
Figure 9C:
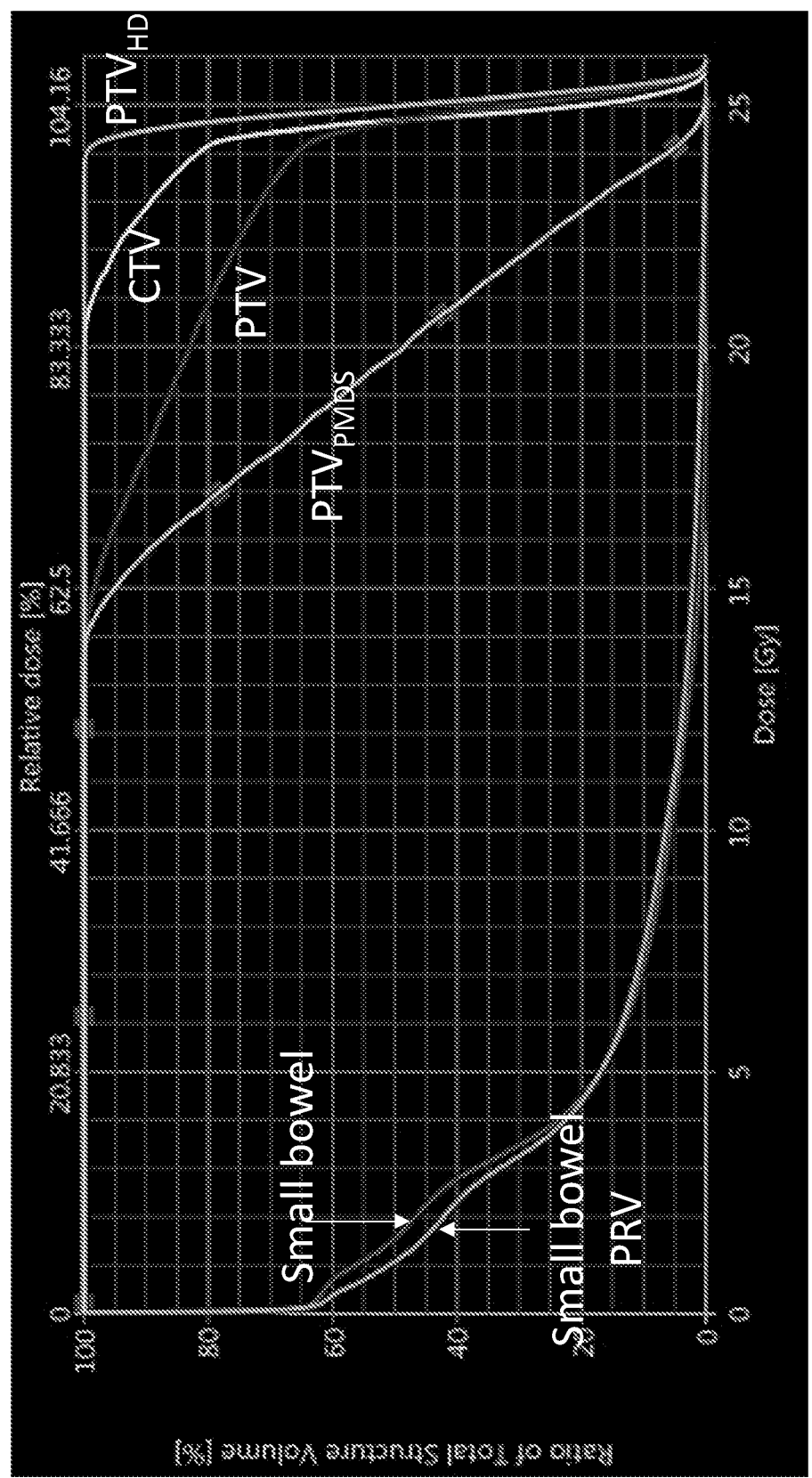

FIGS. 9A-9C presents one of the SDRT-PMDS 17.9 Gy-≤12 Gy cases. An isolated FDG-avid left pelvic lymph-node from a colorectal primary provided an indication for OM ablative radiotherapy. Treatment planning was performed on a fused PET/CT image acquired with the patient positioned in a vacuum pillow (FIGS. 9A and 9B). The GTV of the involved lymph-node was derived from the area of intense tracer uptake and expanded into a PTV with an isotropic 3 mm margin. The PTV overlap with the sigmoid PRV (obtained with a 3 mm expansion of the gross OAR contour) was utilized to generate the $PTV_{PMDS}$ sub-volume. A steep dose gradient was planned within the $PTV_{PMDS}$ to fulfill a $D_{MAX}$ of 14 Gy restriction to the gross OAR. The overall PTV measured 2.2 cm$^3$, while the $PTV_{PMDS}$ sub-volume measured 0.7 cm$^3$ (31% of the overall PTV). Despite a significant compromise in dose of the total PTV (D50=24.6 Gy; D2=25.2 Gy; D98=15.2 Gy), the lesion was free of FDG-PET evidence of relapse at 37 months. FIG. 9C shows the DVHs of the pertinent volumes. The $PTV_{HD}$ has a D95 of 24.3 Gy (D50=24.9 Gy; D2=25.6 Gy; D98=24.2 Gy) with a relatively homogeneous dose distribution with a $D_{max}$ of 106.6% of the prescription dose. The CTV is fully covered by the 21 Gy isodose line (D50=24.7 Gy; D2=25.4 Gy; D98=21.2 Gy). However, the $PTV_{PMDS}$ displays a pronounced inhomogeneity (D50=19.8 Gy; D2=24.5 Gy; D98=14.5 Gy) in order to fulfill the normal tissue constraints for the sigmoid at a $D_{MAX}$ of 14.5 Gy with a dose gradient of 42% within 4 mm of the PRV, from the distal edge of the $PTV_{HD}$ penumbra to the contour of the sigmoid. As described above, the resulting dose distribution on the overall PTV is highly inhomogeneous with a D95 of only 16.3 Gy.

Example 2: SDRT-PMDS in Combination with ASMase/Ceramide Activating Agents

The methods described above in Example 1 are further modified to administer a Radiosensitizing Agent (e.g., ASMase/Ceramide activating agent) to patients prior to or concurrently with the administration of radiation. Patients treated with SDRT or SDRT-PMDS are administered the appropriate doses of an ASMase/Ceramide activating agent 24 hours or less prior to radiation administration or concurrently with radiation administration. The Radiosensitizing Agent (e.g ASMase/Ceramide activating agent) can be selected from a vector comprising a polynucleotide encoding the ASMase protein, one or more anti-angiogenic agents, a compositions comprising ceramide, or a recombinant ASMase protein.

These experiments are expected to show that administration of Radiosensitizing agent (e.g., ASMase/Ceramide activating agent) prior to or concurrently with radiation enhance the sensitivity of the tumor to radiation, for example by decreasing the radiation dose delivered to the $PTV_{HD}$ and/or $PTV_{PMDS}$ in order to treat the tumor.

Figure 10A:
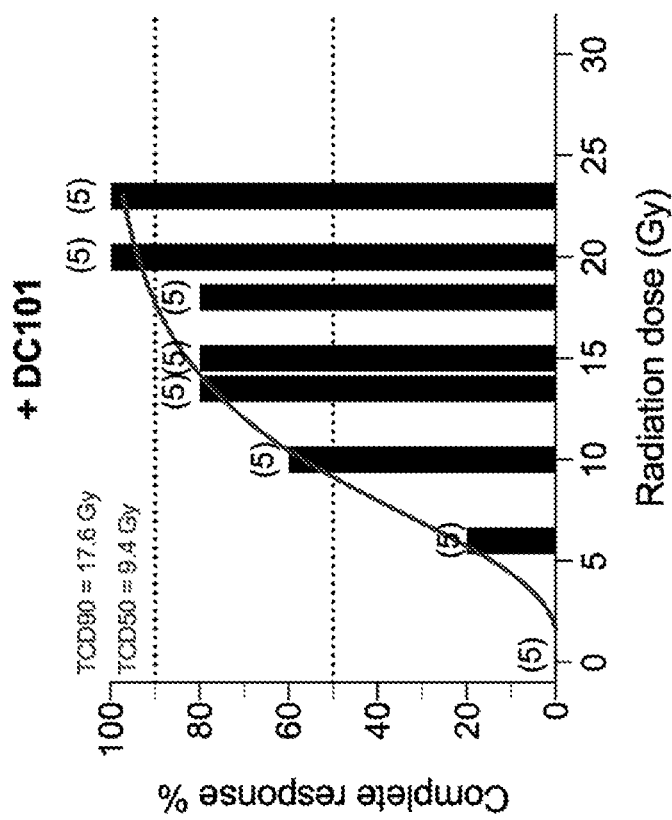
FIG. 10A-FIG. 10C illustrate SDRT radiation dose-response in the presence or absence of the radio-sensitizing agent DC101.
Figure 10B:
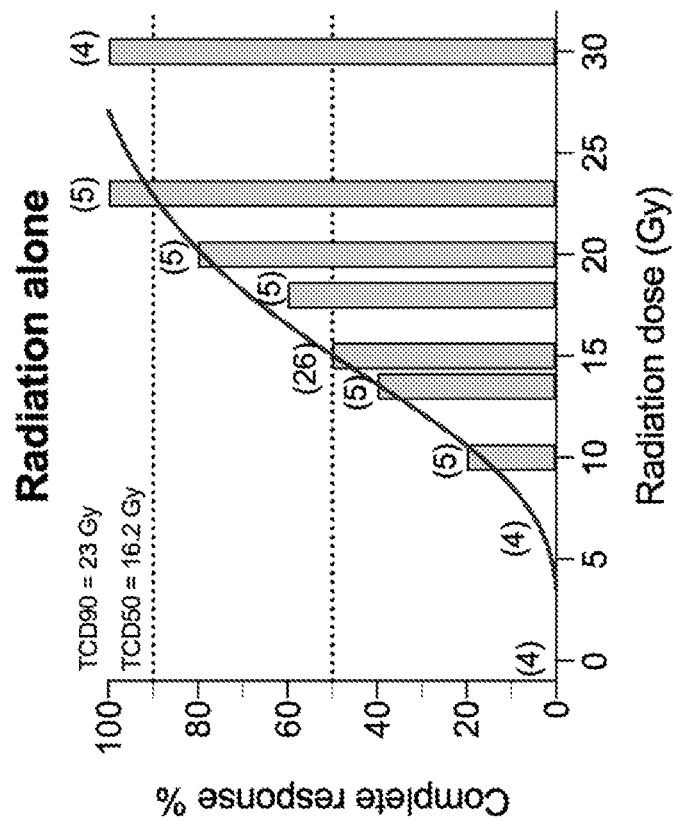
Figure 10C:
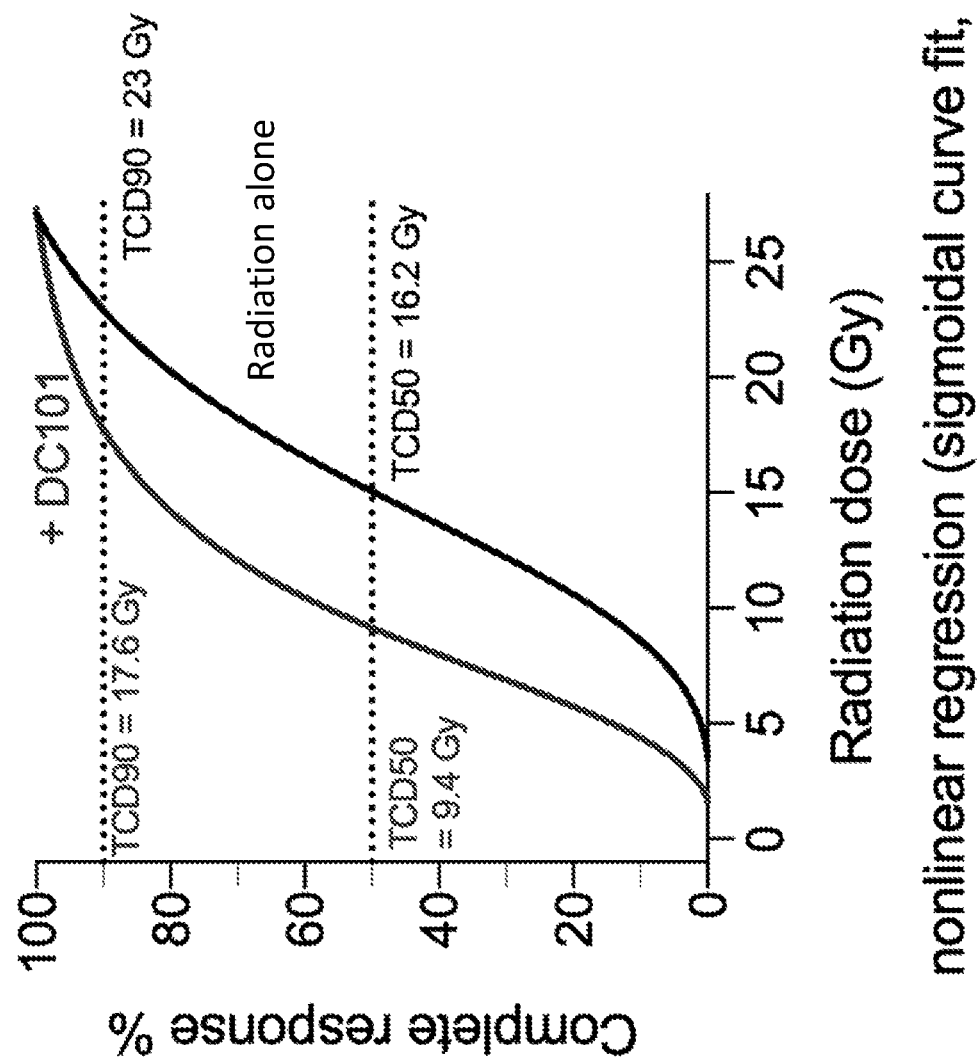

Example 3: Radio-Sensitizing Agents Increase the Effectiveness of SDRT and Reduce the Radiation Dose Necessary for $PTV_{HD}$ Biological Response The effect of an AAA (a radio-sensitizing agent) on the radiation dose-response of SDRT was evaluated using a MCA/129 fibrosarcomas mouse model. Briefly, each mouse received a single dose radiotherapy (SDRT) at the indicated radiation dose, either alone (FIG. 10A) or with a sphingolipid-timed delivery of an anti-angiogenic agent (DC101, an anti-mouse VEGFR-2 monoclonal antibody) prior to SDRT (FIG. 10B), and the percentages of MCA/129 fibrosarcomas undergoing complete response were recorded. FIG. 10C shows a comparison of the fitted curves of radiation dose-response for these two groups. The results showed that, compared to SDRT alone, timed delivery of an anti-angiogenic agent caused significant radiosensitization in the clinical dose range. Specifically, the radiation dose that induced 50% complete response (TCD50) was shifted from 16.2 Gy for radiation alone to 9.4 Gy for radiation in combination with timed delivery of the anti-angiogenic agent.

Figure 11:
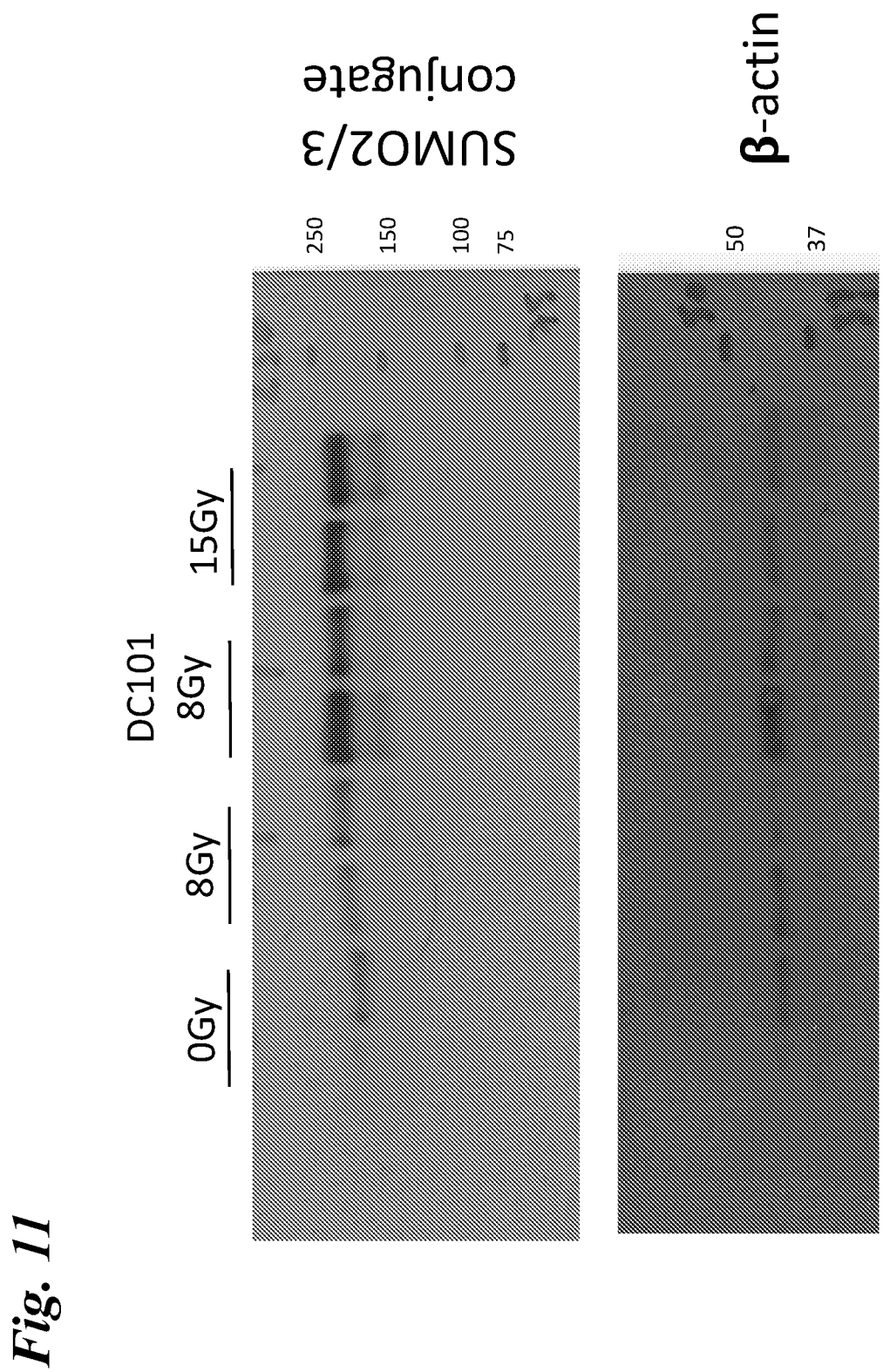
FIG. 11 is a Western blot analysis of tumour extracts after treatment of indicated dose of SDRT (0 Gy, 8 Gy and 15 Gy) and optional DC101 anti-angiogenic agent. Upper panel shows high-molecular weight SUMO2/3 conjugates (>75 kDa) and lower panel shows β-actin as loading control. Two samples are analysed for each treatment condition.

We also measured the cellular levels of SUMO2/3 conjugates, an indicator of the effectiveness of SDRT, and its expected effects on DNA repair. As shown in FIG. 11, sphingolipid-timed delivery of the anti-angiogenic agent DC101 significantly increased the level of SUMO2/3 conjugate at 8 Gy radiation dose, which was comparable to the level of SUMO2/3 conjugate at 15 Gy radiation dose without the addition of DC101. Therefore, addition of the anti-angiogenic agent DC101 converted an 8 Gy dose SDRT to an isoeffective dose of 15 Gy for SDRT alone, as measured by the Sumo stress response.

FURTHER NUMBERED EMBODIMENTS

Further embodiments of the instant invention are provided in the numbered embodiments below:

Embodiment 1

A method of treating a tumor in a subject in need thereof, said tumor comprising: a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$); wherein the method comprises delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$, and wherein the dose of radiation delivered to the $PTV_{PMDS}$ is insufficient to treat the tumor when delivered to the entirety of the $PTV_{TOTAL}$.

Embodiment 2

The method of Embodiment 1, wherein the $PTV_{HD}$ comprises at least 60% of the $PTV_{TOTAL}$.

Embodiment 3

The method of Embodiment 1, wherein the $PTV_{HD}$ comprises at least 60% of the tumor's total volume.

Embodiment 4

The method of any one of Embodiments 1-3, wherein the $PTV_{PMDS}$ comprises 40% or less of the $PTV_{TOTAL}$.

Embodiment 5

The method of any one of Embodiments 1-4, wherein the $PTV_{PMDS}$ comprises at least 5% of the $PTV_{TOTAL}$.

Embodiment 6

The method of any one of Embodiments 1-4, wherein the $PTV_{PMDS}$ comprises at least 5% of the tumor's total volume.

Embodiment 7

The method of any one of Embodiments 1-6, wherein the tumor is adjacent to a dose limiting organ at risk (OAR).

Embodiment 8

The method of Embodiment 7, wherein the OAR is a serial OAR.

Embodiment 9

The method of any one of Embodiments 1-8, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, or at least 26 Gy.

Embodiment 10

The method of Embodiment 9, wherein the dose of radiation delivered to the $PTV_{HD}$ is between about 22 Gy and about 25 Gy.

Embodiment 11

The method of any one of Embodiments 1-10, wherein the dose of radiation delivered to the $PTV_{PMDS}$ is less than about 23 Gy.

Embodiment 12

The method of any one of Embodiments 1-10, wherein the dose of radiation delivered to the $PTV_{PMDS}$ is between about 12 Gy and 23 Gy.

Embodiment 13

The method of any one of Embodiments 1-10, wherein the dose of radiation delivered to the $PTV_{PMDS}$ is less than about 18 Gy.

Embodiment 14

The method of any one of Embodiments 1-10, wherein the dose of radiation delivered to the $PTV_{PMDS}$ is between about 12 Gy and 18 Gy.

Embodiment 15

The method of any one of Embodiments 1-10, wherein the dose of radiation delivered to the $PTV_{PMDS}$ is less than about 12 Gy.

Embodiment 16

The method of any one of Embodiments 1-15, wherein the dose of radiation delivered to the $PTV_{PMDS}$ is at least 10% lower than the dose of radiation delivered to the $PTV_{HD}$.

Embodiment 17

The method of any one of Embodiments 1-15, wherein the dose of radiation delivered to the $PTV_{PMDS}$ is between about 10% and about 50% lower than the dose of radiation delivered to the $PTV_{HD}$.

Embodiment 18

The method of any one of Embodiments 1-15, wherein the dose of radiation delivered to the $PTV_{PMDS}$ is at least 50% lower than the dose of radiation delivered to the $PTV_{HD}$.

Embodiment 19

The method of any one of Embodiments 1-18, wherein the dose of radiation delivered to 99% of the $PTV_{PMDS}$ ($PTV_{PMDS}$-D99) is at least 20% lower than the dose of radiation delivered to 99% of the $PTV_{HD}$ ($PTV_{HD}$-D99).

Embodiment 20

The method of any one of Embodiments 1-18, wherein the dose of radiation delivered to 95% of the $PTV_{PMDS}$ ($PTV_{PMDS}$-D95) is at least 20% lower than the dose of radiation delivered to 95% of the $PTV_{HD}$ ($PTV_{HD}$-D95).

Embodiment 21

The method of any one of Embodiments 1-20, wherein the method reduces incidence of local relapse compared to fractionated radiotherapy methods.

Embodiment 22

The method of any one of Embodiments 1-21, wherein the dose of radiation delivered to the $PTV_{HD}$ and the dose of radiation delivered to the $PTV_{PMDS}$ are delivered in the same treatment session.

Embodiment 23

The method of any one of Embodiments 1-22, wherein the dose of radiation delivered to the $PTV_{HD}$ and the dose of radiation delivered to the $PTV_{PMDS}$ are delivered simultaneously in the same treatment session.

Embodiment 23.1

The method of any one of Embodiments 1-22, wherein the radiation is delivered from a radiation source selected from the group consisting of an x-ray emitter, an electron beam emitter, a proton beam emitter, and a linear accelerator.

Embodiment 23.2

The method of any one of Embodiments 1-22, wherein the radiation is delivered from a radiation source comprising a radioactive element selected from the group consisting of radioactive cesium, iridium, iodine, cobalt, and combinations thereof.

Embodiment 24

A system for treating a tumor comprising: a) a radiation source; and b) an electronic device, the electronic device including at least a memory and a processor operatively coupled to the memory and configured to execute instructions stored on the memory, the processor configured to: i) define a total planning target volume ($PTV_{TOTAL}$) comprising the tumor's total volume, wherein said $PTV_{TOTAL}$ comprises a first planning target sub-volume ($PTV_{HD}$) and a second planning target sub-volume ($PTV_{PMDS}$); ii) define a radiotherapy treatment plan for said $PTV_{TOTAL}$; and iii) send, to the radiation source, a signal indicative of an instruction to deliver radiation doses to the $PTV_{TOTAL}$, wherein the dose of radiation delivered to the $PTV_{PMDS}$ is less the dose of radiation delivered to the $PTV_{HD}$; wherein the dose of radiation delivered to the $PTV_{PMDS}$ is insufficient to treat the tumor when delivered to the entirety of the $PTV_{TOTAL}$.

Embodiment 25

The system of Embodiment 24, wherein the radiation source is selected from the group consisting of an x-ray emitter, an electron beam emitter, a proton beam emitter, and a linear accelerator.

Embodiment 26

The system of Embodiment 24, wherein the radiation source comprises a radioactive element selected from the group consisting of radioactive cesium, iridium, iodine, cobalt, and combinations thereof.

Embodiment 27

The system of any one of Embodiments 24-26, wherein the $PTV_{HD}$ comprises at least 60% of the $PTV_{TOTAL}$.

Embodiment 28

The system of any one of Embodiments 24-26, wherein the $PTV_{HD}$ comprises at least 60% of the tumor's total volume.

Embodiment 29

The system of any one of Embodiments 24-27, wherein the $PTV_{PMDS}$ comprises 40% or less of the $PTV_{TOTAL}$.

Embodiment 30

The system of any one of Embodiments 24-29, wherein the $PTV_{PMDS}$ comprises at least 5% of the $PTV_{TOTAL}$.

Embodiment 31

The system of any one of Embodiments 24-29, wherein the $PTV_{PMDS}$ comprises at least 5% of the tumor's total volume.

Embodiment 32

The system of any one of Embodiments 24-31, wherein the tumor is adjacent to a dose limiting organ at risk (OAR).

Embodiment 33

The system of Embodiment 32, wherein the OAR is a serial OAR.

Embodiment 34

The system of any one of Embodiments 24-33, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, or at least 26 Gy.

Embodiment 35

The system of Embodiment 34, wherein the dose of radiation delivered to the $PTV_{HD}$ is between about 22 Gy and about 25 Gy.

Embodiment 36

The system of any one of Embodiments 24-35, wherein the dose of radiation delivered to the $PTV_{PMDS}$ is less than about 23 Gy.

Embodiment 37

The system of any one of Embodiments 24-35, wherein the dose of radiation delivered to the $PTV_{PMDS}$ is between about 12 Gy and 23 Gy.

Embodiment 38

The system of any one of Embodiments 24-35, wherein the dose of radiation delivered to the $PTV_{PMDS}$ is less than about 18 Gy.

Embodiment 39

The system of any one of Embodiments 24-35, wherein the dose of radiation delivered to the $PTV_{PMDS}$ is between about 12 Gy and 18 Gy.

Embodiment 40

The system of any one of Embodiments 24-35, wherein the dose of radiation delivered to the $PTV_{PMDS}$ is less than about 12 Gy.

Embodiment 41

The system of any one of Embodiments 24-40, wherein the dose of radiation delivered to the $PTV_{PMDS}$ is at least about 10% lower than the dose of radiation delivered to the $PTV_{HD}$.

Embodiment 42

The system of any one of Embodiments 24-40, wherein the dose of radiation delivered to the $PTV_{PMDS}$ is between about 10% and 50% lower than the dose of radiation delivered to the $PTV_{HD}$.

Embodiment 43

The system of any one of Embodiments 24-40, wherein the dose of radiation delivered to the $PTV_{PMDS}$ is at least 50% lower than the dose of radiation delivered to the $PTV_{HD}$.

Embodiment 44

The system of any one of Embodiments 24-43, wherein the dose of radiation delivered to 99% of the $PTV_{PMDS}$ ($PTV_{PMDS}$-D99) is at least 20% lower than the dose of radiation delivered to 99% of the $PTV_{HD}$ ($PTV_{HD}$-D99).

Embodiment 45

The system of any one of Embodiments 24-43, wherein the dose of radiation delivered to 95% of the $PTV_{PMDS}$ ($PTV_{PMDS}$-D95) is at least 20% lower than the dose of radiation delivered to 95% of the $PTV_{HD}$ ($PTV_{HD}$-D95).

Embodiment 46

The system of any one of Embodiments 24-45, wherein the dose of radiation delivered to the $PTV_{HD}$ and the dose of radiation delivered to the $PTV_{PMDS}$ are delivered in the same treatment session.

Embodiment 47

The system of any one of Embodiments 24-46, wherein the dose of radiation delivered to the $PTV_{HD}$ and the dose of radiation delivered to the $PTV_{PMDS}$ are delivered simultaneously in the same treatment session.

Embodiment 48

The system of any one of Embodiments 24-27, wherein the electronic device is in communication with the radiation source via a network.

Embodiment 49

The system of any one of Embodiments 24-47, wherein the electronic device and the radiation source are included in a single machine.

Embodiment 50

The system of any one of Embodiments 24-49, further comprising: an imaging device configured to capture one or more images of the tumor, wherein the processor is configured to define the $PTV_{TOTAL}$ based at least in part on the one or more images of the tumor captured by the imaging device.

Embodiment 51

The system of Embodiment 50, wherein the imaging device and the radiation source are included in the same machine.

Embodiment 51.1

The system of Embodiments 50 or 51, wherein the imaging device and the electronic device are included in the same machine.

Embodiment 51.2

The system of Embodiment 50 or 51, wherein the imaging device is in communication with the electronic device via a network.

Embodiment 52

A method of treating a tumor in a subject in need thereof comprising: defining, at a processor, a total planning target volume ($PTV_{TOTAL}$) of the tumor; dividing, at the processor, the $PTV_{TOTAL}$ of the tumor into at least a first planning target sub-volume ($PTV_{HD}$) and a second planning target sub-volume ($PTV_{PMDS}$); sending, from the processor and to a radiation source, a signal associated with a perfusion modulated dose sculpting (PMDS) radiotherapy plan; and delivering, from the radiation source, a dose of radiation to each of the $PTV_{HD}$ and the $PTV_{PMDS}$ based on the PMDS radiotherapy plan, wherein the dose of radiation covering 95% of the $PTV_{PMDS}$ ($PTV_{PMDS}$-D95) is lower than the dose of radiation covering 95% of the $PTV_{HD}$ ($PTV_{HD}$-D95) and wherein the $PTV_{PMDS}$-D95 is lower than the dose of radiation covering 95% of the total PTV ($PTV_{TOTAL}$-D95) required to treat the tumor.

Embodiment 53

The method of Embodiment 52, wherein the $PTV_{HD}$ comprises at least 60% of the total $PTV_{TOTAL}$.

Embodiment 54

The method of Embodiment 52, wherein the $PTV_{HD}$ comprises at least 60% of the tumor.

Embodiment 55

The method of any one of Embodiments 52-54, wherein the $PTV_{PMDS}$ comprises 40% or less of the $PTV_{TOTAL}$.

Embodiment 56

The method of any one of Embodiments 52-55, wherein the $PTV_{PMDS}$ comprises at least 5% of the $PTV_{TOTAL}$.

Embodiment 57

The method of any one of Embodiments 52-55, wherein the $PTV_{PMDS}$ comprises at least 5% of the tumor.

Embodiment 58

The method of any one of Embodiments 52-57, wherein the tumor is adjacent to a dose limiting organ at risk (OAR).

Embodiment 59

The method of Embodiment 58, wherein the OAR is a serial OAR.

Embodiment 60

The method of any one of Embodiments 52-59, wherein the $PTV_{HD}$-D95 is at least 18 Gy, at least 19 Gy, at least 20 Gy, at least 21 Gy, at least 22 Gy, at least 23 Gy, at least 24 Gy, at least 25 Gy, or at least 26 Gy.

Embodiment 61

The method of Embodiment 60, wherein the $PTV_{HD}$-D95 is between about 22 Gy and about 25 Gy.

Embodiment 62

The method of any one of Embodiments 52-61, wherein the $PTV_{PMDS}$-D95 is less than about 23 Gy.

Embodiment 63

The method of any one of Embodiments 52-61, wherein the $PTV_{PMDS}$-D95 is between about 12 Gy and 23 Gy.

Embodiment 64

The method of any one of Embodiments 52-61, wherein the $PTV_{PMDS}$-D95 is less than about 18 Gy.

Embodiment 65

The method of any one of Embodiments 52-61, wherein the $PTV_{PMDS}$-D95 is between about 12 Gy and 18 Gy.

Embodiment 66

The method of any one of Embodiments 52-61, wherein the $PTV_{PMDS}$-D95 is less than about 12 Gy.

Embodiment 67

The method of any one of Embodiments 52-66, wherein the $PTV_{PMDS}$-D95 is at least 10% lower than the $PTV_{HD}$-D95.

Embodiment 68

The method of any one of Embodiments 52-66, wherein the $PTV_{PMDS}$-D95 is between about 10% and about 50% lower than the $PTV_{HD}$-D95.

Embodiment 69

The method of any one of Embodiments 52-66, wherein the $PTV_{PMDS}$-D95 is at least 50% lower than the $PTV_{HD}$-D95.

Embodiment 70

The method of any one of Embodiments 52-69, wherein the $PTV_{PMDS}$-D95 is at least 10% lower than the $PTV_{TOTAL}$-D95 required to treat the tumor.

Embodiment 71

The method of any one of Embodiments 52-69, wherein the $PTV_{PMDS}$-D95 is between about 10% and about 50% lower than the $PTV_{TOTAL}$-D95 required to treat the tumor.

Embodiment 72

The method of any one of Embodiments 52-69, wherein the $PTV_{PMDS}$-D95 is at least 50% lower than the $PTV_{TOTAL}$-D95 required to treat the tumor.

Embodiment 73

The method of any one of Embodiments 52-72, wherein the method reduces incidence of local relapse compared to fractionated radiotherapy methods.

Embodiment 74

The system of any one of Embodiments 52-73, wherein the doses of radiation are delivered to the $PTV_{HD}$ and the $PTV_{PMDS}$ in the same treatment session.

Embodiment 75

The method of any one of Embodiments 52-74, wherein the doses of radiation are delivered to the $PTV_{HD}$ and the $PTV_{PMDS}$ simultaneously in the same treatment session.

Embodiment 76

The method of any one of Embodiments 52-75, wherein sending the signal from the processor to the radiation source includes sending the signal via a network.

Embodiment 77

The method of any one of Embodiments 52-75, wherein the processor is included in an electronic device having at least the processor and a memory; and wherein the electronic device and the radiation source are included in a single machine.

Embodiment 78

The method of any one of Embodiments 52-77, further comprising: capturing one or more images of the tumor via an imaging device; and sending, from the imaging device and to the processor, data associated with the one or more images; wherein the processor is configured to define the $PTV_{TOTAL}$ based at least in part on the data associated with the one or more images of the tumor.

Embodiment 79

The method of Embodiment 78, wherein the imaging device and the radiation source are included in the same machine.

Embodiment 80

The method of Embodiments 78 or 79, wherein the processor is included in an electronic device having at least the processor and a memory; and wherein the electronic device and the imaging device are included in a single machine.

Embodiment 81

The method of Embodiment 78 or 79, wherein the imaging device is in communication with the electronic device via a network.

Another set of embodiments (Embodiment_B) of the instant invention are provided in the numbered embodiments below:

Embodiment_B1

A method of treating a tumor in a subject in need thereof, said tumor comprising: a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$); wherein the method comprises delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$, and wherein the dose of radiation delivered to the $PTV_{PMDS}$ is insufficient to treat the tumor when delivered to the entirety of the $PTV_{TOTAL}$.

Embodiment_B2

The method of Embodiment_B1, wherein the $PTV_{HD}$ comprises at least 60% of the $PTV_{TOTAL}$.

Embodiment_B3

The method of Embodiment_B1, wherein the $PTV_{HD}$ comprises at least 60% of the tumor's total volume.

Embodiment_B4

The method of any one of Embodiment_Bs 1-3, wherein the $PTV_{PMDS}$ comprises 40% or less of the $PTV_{TOTAL}$.

Embodiment_B5

The method of any one of Embodiment_Bs 1-4, wherein the $PTV_{PMDS}$ comprises at least 5% of the $PTV_{TOTAL}$.

Embodiment_B6

The method of any one of Embodiment_Bs 1-4, wherein the $PTV_{PMDS}$ comprises at least 5% of the tumor's total volume.

Embodiment_B7

The method of any one of Embodiment_Bs 1-6, wherein the tumor is adjacent to a dose limiting organ at risk (OAR).

Embodiment_B8

The method of Embodiment_B7, wherein the OAR is a serial OAR.

Embodiment_B9

The method of any one of Embodiment_Bs 1-8, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, or at least 26 Gy.

Embodiment_B10

The method of Embodiment_B9, wherein the dose of radiation delivered to the $PTV_{HD}$ is between about 22 Gy and about 25 Gy.

Embodiment_B11

The method of any one of Embodiment_Bs 1-10, wherein the dose of radiation delivered to the $PTV_{PMDS}$ is less than about 23 Gy.

Embodiment_B12

The method of any one of Embodiment_Bs 1-10, wherein the dose of radiation delivered to the $PTV_{PMDS}$ is between about 12 Gy and 23 Gy.

Embodiment_B13

The method of any one of Embodiment_Bs 1-10, wherein the dose of radiation delivered to the $PTV_{PMDS}$ is less than about 18 Gy.

Embodiment_B14

The method of any one of Embodiment_Bs 1-10, wherein the dose of radiation delivered to the $PTV_{PMDS}$ is between about 12 Gy and 18 Gy.

Embodiment_B15

The method of any one of Embodiment_Bs 1-10, wherein the dose of radiation delivered to the $PTV_{PMDS}$ is less than about 12 Gy.

Embodiment_B16

The method of any one of Embodiment_Bs 1-15, wherein the dose of radiation delivered to the $PTV_{PMDS}$ is at least 10% lower than the dose of radiation delivered to the $PTV_{HD}$.

Embodiment_B17

The method of any one of Embodiment_Bs 1-15, wherein the dose of radiation delivered to the $PTV_{PMDS}$ is between about 10% and about 50% lower than the dose of radiation delivered to the $PTV_{HD}$.

Embodiment_B18

The method of any one of Embodiment_Bs 1-15, wherein the dose of radiation delivered to the $PTV_{PMDS}$ is at least 50% lower than the dose of radiation delivered to the $PTV_{HD}$.

Embodiment_B19

The method of any one of Embodiment_Bs 1-18, wherein the dose of radiation delivered to 99% of the $PTV_{PMDS}$ ($PTV_{PMDS}$-D99) is at least 20% lower than the dose of radiation delivered to 99% of the $PTV_{HD}$ ($PTV_{HD}$-D99).

Embodiment_B20

The method of any one of Embodiment_Bs 1-18, wherein the dose of radiation delivered to 95% of the $PTV_{PMDS}$ ($PTV_{PMDS}$-D95) is at least 20% lower than the dose of radiation delivered to 95% of the $PTV_{HD}$ ($PTV_{HD}$-D95).

Embodiment_B21

The method of any one of Embodiment_Bs 1-20, wherein the method reduces incidence of local relapse compared to fractionated radiotherapy methods.

Embodiment_B22

The method of any one of Embodiment_Bs 1-21, wherein the dose of radiation delivered to the $PTV_{HD}$ and the dose of radiation delivered to the $PTV_{PMDS}$ are delivered in the same treatment session.

Embodiment_B23

The method of any one of Embodiment_Bs 1-22, wherein the dose of radiation delivered to the $PTV_{HD}$ and the dose of radiation delivered to the $PTV_{PMDS}$ are delivered simultaneously in the same treatment session.

Embodiment_B24

The method of any one of Embodiment_Bs 1-23, wherein the method further comprises administering a radio-sensitizing agent to the subject prior to delivering the radiation to the subject.

Embodiment_B25

A method of treating a tumor in a subject in need thereof, said tumor comprising: a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$); wherein the method comprises administering a radio-sensitizing agent to the subject; and delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$, and wherein the dose of radiation delivered to the $PTV_{PMDS}$ is insufficient to treat the tumor when delivered to the entirety of the $PTV_{TOTAL}$ in the absence of the radio-sensitizing agent.

Embodiment_B26

A method of treating a tumor in a subject in need thereof, said tumor comprising: a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$); wherein the method comprises delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$; and wherein the dose of radiation delivered to the $PTV_{PMDS}$ is insufficient to treat the tumor when delivered to the entirety of the $PTV_{TOTAL}$, wherein the subject had previously been administered a radio-sensitizing agent prior to delivering the radiation to the subject.

Embodiment_B27

The method of any one of Embodiment_Bs 24-26, wherein the radio-sensitizing agent is an ASMase/Ceramide activating agent selected from a vector comprising a polynucleotide encoding the ASMase protein, an anti-angiogenic agent (AAA), a composition comprising ceramide, a recombinant ASMase protein, a ceramidase antagonist, and a sphingosine kinase antagonist.

Embodiment_B27.1

The method of any one of Embodiment_Bs 24-26, wherein the radio-sensitizing agent is an ASMase/Ceramide activating agent selected from a protein kinase C (PKC) activator, TNF-alpha, an agent that downregulates or inhibits the expression and/or activity of caveolin-1 (CAV1), CD95 (Fas/APO-1), lipopolysaccharide (LPS), Palmitic acid (PA), lysobisphophatidic acid (LBPA), and phosphatidylinositol (PI).

Embodiment_B27.2

The method of any one of Embodiment_Bs 24-26, wherein the radio-sensitizing agent is a radiosensitizer selected from the group consisting of fluoropyrimidine, gemcitabine, a platinum analog such as cisplatin, NBTXR3, Nimoral, trans sodium crocetinate (TSC), NVX-108, misonidazole, metronidazole, tirapazamine, vandate, nitroimidazole alkylsulfonamides, ATR inhibitor AZD6738, taxane containing at least 2 electron-affinic radiosensitizing functional groups, 2-carboxyaldehyde pyridine thiosemicarbazone compound or prodrug thereof, substituted diamines containing 2-4 electron-affinic radiosensitizing functional groups, lanthanide-based nanoparticles, platinum complexes with one radiosensitizing ligand, indazolpyrrolotriazines, anthraquinones, and monomethyl auristatin e (mmae) and derivatives thereof.

Embodiment_B27.3

The method of any one of Embodiment_Bs 24-26, wherein the radio-sensitizing agent is a radiosensitizer selected from the group consisting of a fluorocarbon, a halogenated nucleoside or its analog, a poly-(ADP-ribose)-polymerase (PARP) inhibitor, a histone H3 demethylase inhibitor, and a histone deacetylase (HDAC) inhibitor.

Embodiment_B27.4

The method of any one of Embodiment_Bs 24-26, wherein the radio-sensitizing agent is a polynucleotide encoding the ASMase protein.

Embodiment_B27.5

The method of Embodiment_B27.4, wherein the polynucleotide encoding the ASMase protein is a messenger RNA.

Embodiment_B28

The method of Embodiment_B27, wherein the vector is a nucleic acid vector selected from a replicon, a plasmid, a cosmid, a phagemid, a transposon, a bacterial artificial chromosome, a yeast artificial chromosome, or a viral vector.

Embodiment_B29

The method of Embodiment_B28, wherein the viral vector is selected from an adenoviral vector, an adenovirus-associated viral vector, a retroviral vector, or a lentiviral vector.

Embodiment_B30

The method of any one of Embodiment_Bs 27-29, wherein the polynucleotide encoding the ASMase protein is operably linked to a promoter sequence.

Embodiment_B31

The method of Embodiment_B30, wherein the promoter is an endothelial cell specific promoter selected from the endoglin promoter, the fins-like tyrosine kinase-1 (Flt-1) promoter, the intercellular adhesion molecule-2 (ICAM-2) promoter, the von Willebrand factor (vWF) promoter, the tyrosine kinase with immunoglobulin and epidermal growth factor homology domains (TIE) promoter, the kinase-like domain receptor (KDR) promoter, the cadherin 5 (CDH5) promoter, the P-selectin promoter, the preproendothelin-1 (PPE-1) promoter, the platelet endothelial cell adhesion molecule-1 (PECAM-1) promoter, the VE-cadherin (VECD) promoter, or modified or synthetic versions thereof.

Embodiment_B32

The method of Embodiment_B31, wherein the promoter is a modified PPE-1 promoter and is the PPE1-3× promoter.

Embodiment_B33

The method of any one of Embodiment_Bs 28-32, wherein the vector further comprises one or more enhancer sequences that drive expression of the ASMase protein in angiogenic cells.

Embodiment_B34

The method of Embodiment_B33, wherein the enhancer is selected from hypoxia-inducible factor-1α (HIF-1α) binding motifs or MEF2 binding motifs.

Embodiment_B35

The method of Embodiment_B27, wherein vector is a non-nucleic acid vector selected from a nanoparticle, an exosome, a liposome, and a lipoplex.

Embodiment_B36

The method of Embodiment_B27, wherein the radiosensitizing agent is an mRNA polynucleotide encoding for ASMase.

Embodiment_B37

The method of Embodiment_B27, wherein the radio-sensitizing agent is an anti-angiogenic agent (AAA).

Embodiment_B37.1

The method of Embodiment_B37, wherein the AAA is an antagonist against one or more angiogenic growth factors and/or their receptors.

Embodiment_B37.2

The method of Embodiment_B37.1, wherein the antagonist is an antagonist against one or more angiogenic growth factors selected from FGF family growth factors, VEGF family growth factors, PDGF family growth factors, HGF family growth factors and Angiopoietin family growth factors.

Embodiment_B37.3

The method of Embodiment_B37.1, wherein the antagonist is an antagonist against one or more angiogenic growth factor receptors selected from a VEGF receptor, an FGF receptor, a PDGF receptor, c-Met, and a Tie family receptor.

Embodiment_B37.4

The method of any one of Embodiment_Bs 37.1-37.3, wherein the antagonist is a small molecule.

Embodiment_B37.5

The method of any one of Embodiment_Bs 37.1-37.3, wherein the antagonist is an antibody or antigen-binding fragment thereof.

Embodiment_B37.6

The method of any one of Embodiment_Bs 37.1-37.3, wherein the antagonist is a Fab, a scFv, or a variant of scFv.

Embodiment_B37.7

The method of any one of Embodiment_Bs 37-37.6, wherein the AAA is a short-acting AAA.

Embodiment_B37.8

The method of Embodiment_B37, wherein the anti-angiogenic agent is selected from ADH-1, Anginex (betapep-25), Axitinib (Inlyta®), AZD4547, Bevacizumab (Avastin®), Bortezomib, Brivanib, anti-BV8 antibodies, Cabozantinib (Cometriq®), Cediranib, Celecoxib, (AZD-2171 or Recentin), Cilengitide, Dasatinib, Dacinostat, Dovitinib, DX-2400, Everolimus (Afinitor®), Gossypol, JNJ-28312141, Lenalidomide (Revlimid®), Levatinib mesylate (Lenvima®), Nintedanib, NVP-AUY922, Pazopanib (Votrient®), PI-88, Ponatinib (Iclusig), Ramucirumab (Cyramza®), Regorafenib (Stivarga®), Repertaxin, Sorafenib (Nexavar®), Sunitinib (Sutent®), SU6668 (Oratinib), Thalidomide (Synovir, Thalomid®), Tipifarnib, Vatalanib, Vandetanib (Caprelsa®), Volociximab, Ziv-aflibercept (Zaltrap®), Zoledronic acid, and Semaxanib.

Embodiment_B38

The method of any one of Embodiment_Bs 27-27.3 and 37-37.8, wherein the radio-sensitizing agent is administered between 0.5 hours and 48 hours, 0.5 hours and 24 hours, 0.5 hours and 12 hours, 0.5 hours and 4 hours, or 0.5 hours and 2 hours prior to radiation delivery.

Embodiment_B39

The method of any one of Embodiment_Bs 27-27.3 and 37-37.8, wherein the subject has previously been administered the radio-sensitizing agent between 0.5 hours and 48 hours, 0.5 hours and 24 hours, 0.5 hours and 12 hours, 0.5 hours and 4 hours, or 0.5 hours and 2 hours prior to radiation delivery.

Embodiment_B40

The method of Embodiment_B27, wherein the composition comprising ceramide is a composition of ceramide nanoliposomes.

Embodiment_B40.1

The method of Embodiment_B27, wherein the ceramide is C16:0 ceramide, C18:0 ceramide, or a combination thereof.

Embodiment_B41

The method of any one of Embodiment_Bs 24-40.1, wherein the radio-sensitizing agent is administered to the subject prior to or simultaneously with the delivery of radiation.

Embodiment_B42

The method of any one of Embodiment_Bs 24-40, wherein the radiation dose delivered to the $PTV_{PMDS}$ is at least 10% lower than the dose of radiation required to be delivered to the $PTV_{PMDS}$ in the absence of the radio-sensitizing agent.

Embodiment_B42.1

The method of any one of Embodiment_Bs 24-40, wherein the radiation dose delivered to the $PTV_{HD}$ is at least 10% lower than the dose of radiation required to be delivered to the $PTV_{HD}$ in the absence of the radio-sensitizing agent.

Embodiment_B43

A system for treating a tumor comprising: (a) a radiation source; (b) one or more memories; and (c) one or more processors operatively coupled to at least one of the one or more memories and configured to execute instructions stored on the at least one of the one or more memories, the processor configured to: (i) define a total planning target volume ($PTV_{TOTAL}$) comprising the tumor's total volume, wherein said $PTV_{TOTAL}$ comprises a first planning target sub-volume ($PTV_{HD}$) and a second planning target sub-volume ($PTV_{PMDS}$); and (ii) send, to the radiation source, a signal indicative of an instruction to deliver radiation doses to the $PTV_{TOTAL}$, wherein the dose of radiation delivered to the $PTV_{PMDS}$ is less the dose of radiation delivered to the $PTV_{HD}$; wherein the dose of radiation delivered to the $PTV_{PMDS}$ is insufficient to treat the tumor when delivered to the entirety of the $PTV_{TOTAL}$.

Embodiment_B44

The system of Embodiment_B43, wherein the radiation source is selected from the group consisting of an x-ray emitter, an electron beam emitter, a proton beam emitter, and a linear accelerator.

Embodiment_B44.1

The system of Embodiment_B43, wherein the radiation source is an ionizing radiation source.

Embodiment_B45

The system of Embodiment_B43, wherein the radiation source comprises a radioactive element selected from the group consisting of radioactive cesium, iridium, iodine, cobalt, and combinations thereof.

Embodiment_B46

The system of any one of Embodiment_Bs 43-45, wherein the $PTV_{HD}$ comprises at least 60% of the $PTV_{TOTAL}$.

Embodiment_B47

The system of any one of Embodiment_Bs 43-45, wherein the $PTV_{HD}$ comprises at least 60% of the tumor's total volume.

Embodiment_B48

The system of any one of Embodiment_Bs 43-46, wherein the $PTV_{PMDS}$ comprises 40% or less of the $PTV_{TOTAL}$.

Embodiment_B49

The system of any one of Embodiment_Bs 43-48, wherein the $PTV_{PMDS}$ comprises at least 5% of the $PTV_{TOTAL}$.

Embodiment_B50

The system of any one of Embodiment_Bs 43-48, wherein the $PTV_{PMDS}$ comprises at least 5% of the tumor's total volume.

Embodiment_B51

The system of any one of Embodiment_Bs 43-50, wherein the tumor is adjacent to a dose limiting organ at risk (OAR).

Embodiment_B52

The system of Embodiment_B51, wherein the OAR is a serial OAR.

Embodiment_B53

The system of any one of Embodiment_Bs 43-52, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, or at least 26 Gy.

Embodiment_B54

The system of Embodiment_B34, wherein the dose of radiation delivered to the $PTV_{HD}$ is between about 22 Gy and about 25 Gy.

Embodiment_B55

The system of any one of Embodiment_Bs 43-54, wherein the dose of radiation delivered to the $PTV_{PMDS}$ is less than about 23 Gy.

Embodiment_B56

The system of any one of Embodiment_Bs 43-54, wherein the dose of radiation delivered to the $PTV_{PMDS}$ is between about 12 Gy and 23 Gy.

Embodiment_B57

The system of any one of Embodiment_Bs 43-54, wherein the dose of radiation delivered to the $PTV_{PMDS}$ is less than about 18 Gy.

Embodiment_B58

The system of any one of Embodiment_Bs 43-54, wherein the dose of radiation delivered to the $PTV_{PMDS}$ is between about 12 Gy and 18 Gy.

Embodiment_B59

The system of any one of Embodiment_Bs 43-54, wherein the dose of radiation delivered to the $PTV_{PMDS}$ is less than about 12 Gy.

Embodiment_B60

The system of any one of Embodiment_Bs 43-59, wherein the dose of radiation delivered to the $PTV_{PMDS}$ is at least about 10% lower than the dose of radiation delivered to the $PTV_{HD}$.

Embodiment_B61

The system of any one of Embodiment_Bs 43-59, wherein the dose of radiation delivered to the $PTV_{PMDS}$ is between about 10% and 50% lower than the dose of radiation delivered to the $PTV_{HD}$.

Embodiment_B62

The system of any one of Embodiment_Bs 43-59, wherein the dose of radiation delivered to the $PTV_{PMDS}$ is at least 50% lower than the dose of radiation delivered to the $PTV_{HD}$.

Embodiment_B63

The system of any one of Embodiment_Bs 43-62, wherein the dose of radiation delivered to 99% of the $PTV_{PMDS}$ ($PTV_{PMDS}$-D99) is at least 20% lower than the dose of radiation delivered to 99% of the $PTV_{HD}$ ($PTV_{HD}$-D99).

Embodiment_B64

The system of any one of Embodiment_Bs 43-62, wherein the dose of radiation delivered to 95% of the $PTV_{PMDS}$ ($PTV_{PMDS}$-D95) is at least 20% lower than the dose of radiation delivered to 95% of the $PTV_{HD}$ ($PTV_{HD}$-D95).

Embodiment_B65

The system of any one of Embodiment_Bs 43-64, wherein the dose of radiation delivered to the $PTV_{HD}$ and the dose of radiation delivered to the $PTV_{PMDS}$ are delivered in the same treatment session.

Embodiment_B66

The system of any one of Embodiment_Bs 43-65, wherein the dose of radiation delivered to the $PTV_{HD}$ and the dose of radiation delivered to the $PTV_{PMDS}$ are delivered simultaneously in the same treatment session.

Embodiment_B67

A method of treating a tumor in a subject in need thereof comprising: defining a total planning target volume ($PTV_{TOTAL}$) of the tumor; dividing the $PTV_{TOTAL}$ of the tumor into at least a first planning target sub-volume ($PTV_{HD}$) and a second planning target sub-volume ($PTV_{PMDS}$); and delivering a dose of radiation to each of the $PTV_{HD}$ and the $PTV_{PMDS}$, wherein the dose of radiation covering 95% of the $PTV_{PMDS}$ ($PTV_{PMDS}$-D95) is lower than the dose of radiation covering 95% of the $PTV_{HD}$ ($PTV_{HD}$-D95) and wherein the $PTV_{PMDS}$-D95 is lower than the dose of radiation covering 95% of the total PTV ($PTV_{TOTAL}$-D95) required to treat the tumor.

Embodiment_B68

The method of Embodiment_B67, wherein the $PTV_{HD}$ comprises at least 60% of the total $PTV_{TOTAL}$.

Embodiment_B69

The method of Embodiment_B67, wherein the $PTV_{HD}$ comprises at least 60% of the tumor.

Embodiment_B70

The method of any one of Embodiment_Bs 67-69, wherein the $PTV_{PMDS}$ comprises 40% or less of the $PTV_{TOTAL}$.

Embodiment_B71

The method of any one of Embodiment_Bs 67-70, wherein the $PTV_{PMDS}$ comprises at least 5% of the $PTV_{TOTAL}$.

Embodiment_B72

The method of any one of Embodiment_Bs 67-70, wherein the $PTV_{PMDS}$ comprises at least 5% of the tumor.

Embodiment_B73

The method of any one of Embodiment_Bs 67-72, wherein the tumor is adjacent to a dose limiting organ at risk (OAR).

Embodiment_B74

The method of Embodiment_B73, wherein the OAR is a serial OAR.

Embodiment_B75

The method of any one of Embodiment_Bs 67-74, wherein the $PTV_{HD}$-D95 is at least 18 Gy, at least 19 Gy, at least 20 Gy, at least 21 Gy, at least 22 Gy, at least 23 Gy, at least 24 Gy, at least 25 Gy, or at least 26 Gy.

Embodiment_B76

The method of Embodiment_B75, wherein the $PTV_{HD}$-D95 is between about 22 Gy and about 25 Gy.

Embodiment_B77

The method of any one of Embodiment_Bs 67-76, wherein the $PTV_{PMDS}$-D95 is less than about 23 Gy.

Embodiment_B78

The method of any one of Embodiment_Bs 67-76, wherein the $PTV_{PMDS}$-D95 is between about 12 Gy and 23 Gy.

Embodiment_B79

The method of any one of Embodiment_Bs 67-76, wherein the $PTV_{PMDS}$-D95 is less than about 18 Gy.

Embodiment_B80

The method of any one of Embodiment_Bs 67-76, wherein the $PTV_{PMDS}$-D95 is between about 12 Gy and 18 Gy.

Embodiment_B81

The method of any one of Embodiment_Bs 67-76, wherein the $PTV_{PMDS}$-D95 is less than about 12 Gy.

Embodiment_B82

The method of any one of Embodiment_Bs 67-81, wherein the $PTV_{PMDS}$-D95 is at least 10% lower than the $PTV_{HD}$-D95.

Embodiment_B83

The method of any one of Embodiment_Bs 67-81, wherein the $PTV_{PMDS}$-D95 is between about 10% and about 50% lower than the $PTV_{HD}$-D95.

Embodiment_B84

The method of any one of Embodiment_Bs 67-81, wherein the $PTV_{PMDS}$-D95 is at least 50% lower than the $PTV_{HD}$-D95.

Embodiment_B85

The method of any one of Embodiment_Bs 67-84, wherein the $PTV_{PMDS}$-D95 is at least 10% lower than the $PTV_{TOTAL}$-D95 required to treat the tumor.

Embodiment_B86

The method of any one of Embodiment_Bs 67-84, wherein the $PTV_{PMDS}$-D95 is between about 10% and about 50% lower than the $PTV_{TOTAL}$-D95 required to treat the tumor.

Embodiment_B87

The method of any one of Embodiment_Bs 67-84, wherein the $PTV_{PMDS}$-D95 is at least 50% lower than the $PTV_{TOTAL}$-D95 required to treat the tumor.

Embodiment_B88

The method of any one of Embodiment_Bs 67-87, wherein the method reduces incidence of local relapse compared to fractionated radiotherapy methods.

Embodiment_B89

The system of any one of Embodiment_Bs 67-88, wherein the doses of radiation are delivered to the $PTV_{HD}$ and the $PTV_{PMDS}$ in the same treatment session.

Embodiment_B90

The method of any one of Embodiment_Bs 67-89, wherein the doses of radiation are delivered to the $PTV_{HD}$ and the $PTV_{PMDS}$ simultaneously in the same treatment session.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of treating a tumor in a subject in need thereof, said tumor comprising:
a total planning target volume ($PTV_{TOTAL}$) comprising the tumor's total volume, wherein the $PTV_{TOTAL}$ comprises a first planning target sub-volume ($PTV_{HD}$) and a second planning target sub-volume ($PTV_{PMDS}$), wherein the $PTV_{PMDS}$ comprises at least 5% of the tumor's total volume;
wherein the method comprises delivering a radiation dose to each of the $PTV_{PMDS}$ and $PTV_{HD}$, wherein the dose of radiation delivered to the $PTV_{PMDS}$ is lower than the dose of radiation delivered to the $PTV_{HD}$, and
wherein the dose of radiation delivered to the $PTV_{PMDS}$ is insufficient to treat the tumor when delivered to the entirety of the $PTV_{TOTAL}$, optionally wherein:
the method reduces incidence of local relapse compared to fractionated radiotherapy methods, or
the tumor is adjacent to a dose limiting organ at risk (OAR), optionally wherein the OAR is a serial OAR, or
the radiation is delivered from a radiation source comprising a radioactive element selected from the group consisting of radioactive cesium, iridium, iodine, cobalt, and combinations thereof, or
the radiation is delivered from a radiation source selected from the group consisting of an x-ray emitter, an electron beam emitter, a proton beam emitter, and a linear accelerator.

2. The method of claim 1, wherein the $PTV_{HD}$ comprises at least 60% of the $PTV_{TOTAL}$ or wherein the $PTV_{HD}$ comprises at least 60% of the tumor's total volume.

3. The method of claim 1, wherein the $PTV_{PMDS}$ comprises 40% or less of the $PTV_{TOTAL}$ or wherein the $PTV_{PMDS}$ comprises at least 5% of the $PTV_{TOTAL}$.

4. The method of claim 1, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, at least 26 Gy, or between about 22 Gy and about 25 Gy; or
wherein the dose of radiation delivered to the $PTV_{PMDS}$ is less than about 23 Gy, less than about 18 Gy, less than about 12 Gy, between about 12 Gy and 23 Gy, or between about 12 Gy and 18 Gy; or
wherein the dose of radiation delivered to the $PTV_{PMDS}$ is at least 10% lower than the dose of radiation delivered to the $PTV_{HD}$, or is between about 10% and about 50% lower than the dose of radiation delivered to the $PTV_{HD}$, or is at least 50% lower than the dose of radiation delivered to the $PTV_{HD}$; or
wherein the dose of radiation delivered to the $PTV_{HD}$ and the dose of radiation delivered to the $PTV_{PMDS}$ are delivered in the same treatment session or are delivered simultaneously in the same treatment session.

5. The method of claim 1, wherein the dose of radiation delivered to 99% of the $PTV_{PMDS}$ is at least 20% lower than the dose of radiation delivered to 99% of the $PTV_{HD}$ or wherein the dose of radiation delivered to 95% of the $PTV_{PMDS}$ is at least 20% lower than the dose of radiation delivered to 95% of the $PTV_{HD}$.

6. The method of claim 1, wherein the method further comprises administering a radio-sensitizing agent to the subject prior to delivering the radiation to the subject, optionally wherein the radio-sensitizing agent is an ASMase/Ceramide activating agent selected from a vector comprising a polynucleotide encoding the ASMase protein, an anti-angiogenic agent (AAA), a composition comprising ceramide, a recombinant ASMase protein, a ceramidase antagonist, and a sphingosine kinase antagonist; or the radio-sensitizing agent is an ASMase/Ceramide activating agent selected from a protein kinase C (PKC) activator, TNF-alpha, an agent that downregulates or inhibits the expression and/or activity of caveolin-1 (CAV1), CD95 (Fas/APO-1), lipopolysaccharide (LPS), Palmitic acid (PA), lysobisphophatidic acid (LBPA), and phosphatidylinositol (PI); or the radio-sensitizing agent is selected from the group consisting of fluoropyrimidine, gemcitabine, a platinum analog such as cisplatin, NBTXR3, Nimoral, trans sodium crocetinate (TSC), NVX-108, misonidazole, metronidazole, tirapazamine, vandate, nitroimidazole alkylsulfonamides, ATR inhibitor AZD6738, taxane containing at least 2 electron-affinic radiosensitizing functional groups, 2-carboxyaldehyde pyridine thiosemicarbazone compound or prodrug thereof, substituted diamines containing 2-4 electron-affinic radiosensitizing functional groups, lanthanide-based nanoparticles, platinum complexes with one radiosensitizing ligand, indazolpyrrolotriazines, anthraquinones, and monomethyl auristatin e (mmae) and derivatives thereof, or the sensitizing agent is selected from the group consisting of a fluorocarbon, a halogenated nucleoside or its analog, a poly-(ADP-ribose)-polymerase (PARP) inhibitor, a histone H3 demethylase inhibitor, and a histone deacetylase (HDAC) inhibitor.

7. A system comprising:
a) a radiation source; and
b) an electronic device, the electronic device including at least a memory and a processor operatively coupled to the memory and configured to execute instructions stored on the memory, the processor configured to:
  i) define a total planning target volume ($PTV_{TOTAL}$) comprising the tumor's total volume, wherein said $PTV_{TOTAL}$ comprises a first planning target sub-volume ($PTV_{HD}$) and a second planning target sub-volume ($PTV_{PMDS}$), wherein the $PTV_{PMDS}$ comprises at least 5% of the tumor's total volume;
  ii) define a radiotherapy treatment plan for said $PTV_{TOTAL}$; and
  iii) send, to the radiation source, a signal indicative of an instruction to deliver radiation doses to the $PTV_{TOTAL}$, wherein the dose of radiation delivered to the $PTV_{PMDS}$ is less the dose of radiation delivered to the $PTV_{HD}$;
wherein the dose of radiation delivered to the $PTV_{PMDS}$ is insufficient to treat the tumor when delivered to the entirety of the $PTV_{TOTAL}$, optionally wherein the tumor is adjacent to a dose limiting organ at risk (OAR), optionally wherein the OAR is a serial OAR.

8. The system of claim 7, wherein the radiation source is selected from the group consisting of an x-ray emitter, an electron beam emitter, a proton beam emitter, and a linear accelerator or wherein the radiation source comprises a radioactive element selected from the group consisting of radioactive cesium, iridium, iodine, cobalt, and combinations thereof.

9. The system of claim 7, wherein the $PTV_{HD}$ comprises at least 60% of the $PTV_{TOTAL}$ or wherein the $PTV_{HD}$ comprises at least 60% of the tumor's total volume.

10. The system of claim 7, wherein the $PTV_{PMDS}$ comprises 40% or less of the $PTV_{TOTAL}$ or wherein the $PTV_{PMDS}$ comprises at least 5% of the $PTV_{TOTAL}$.

11. The system of claim 7, wherein the dose of radiation delivered to the $PTV_{HD}$ is at least 18 Gy, at least 19 Gy, at least 20 Gy, at least 21 Gy, at least 22 Gy, at least 23 Gy, at least 24 Gy, at least 25 Gy, at least 26 Gy, or between about 22 Gy and about 25 Gy; or wherein the dose of radiation delivered to the $PTV_{PMDS}$ is less than about 23 Gy, less than about 18 Gy, less than about 12 Gy, between about 12 Gy and 23 Gy, or between about 12 Gy and 18 Gy; or wherein the dose of radiation delivered to the $PTV_{PMDS}$ is at least 10% lower than the dose of radiation delivered to the $PTV_{HD}$, or is between about 10% and about 50% lower than the dose of radiation delivered to the $PTV_{HD}$, or is at least 50% lower than the dose of radiation delivered to the $PTV_{HD}$; or wherein the dose of radiation delivered to the $PTV_{HD}$ and the dose of radiation delivered to the $PTV_{PMDS}$ are delivered in the same treatment session or are delivered simultaneously in the same treatment session.

12. The system of claim 7, wherein the dose of radiation delivered to 99% of the $PTV_{PMDS}$ is at least 20% lower than the dose of radiation delivered to 99% of the $PTV_{HD}$ or wherein the dose of radiation delivered to 95% of the $PTV_{PMDS}$ is at least 20% lower than the dose of radiation delivered to 95% of the $PTV_{HD}$.

13. The system of claim 7, further comprising:
an imaging device configured to capture one or more images of the tumor,
wherein the processor is configured to define the $PTV_{TOTAL}$ based at least in part on the one or more images of the tumor captured by the imaging device, optionally wherein
the electronic device and the radiation source are included in a single machine; or
the electronic device is in communication with the radiation source via a network; or
wherein the imaging device and the radiation source are included in the same machine; or
wherein the imaging device and the electronic device are included in the same machine; or
wherein the imaging device is in communication with the electronic device via a network.

14. A method of treating a tumor in a subject in need thereof comprising:
defining, at a processor, a total planning target volume ($PTV_{TOTAL}$) of the tumor;
dividing, at the processor, the $PTV_{TOTAL}$ of the tumor into at least a first planning target sub-volume ($PTV_{HD}$) and a second planning target sub-volume ($PTV_{PMDS}$), wherein the $PTV_{PMDS}$ comprises at least 5% of the tumor's total volume;
sending, from the processor and to a radiation source, a signal associated with a perfusion modulated dose sculpting (PMDS) radiotherapy plan; and
delivering, from the radiation source, a dose of radiation to each of the $PTV_{HD}$ and the $PTV_{PMDS}$ based on the PMDS radiotherapy plan,
wherein the dose of radiation covering 95% of the $PTV_{PMDS}$ is lower than the dose of radiation covering 95% of the $PTV_{HD}$ and wherein the dose of radiation covering 95% of the $PTV_{PMDS}$ is lower than the dose of radiation covering 95% of the total PTV required to treat the tumor, optionally wherein the method reduces incidence of local relapse compared to fractionated radiotherapy methods or the tumor is adjacent to a dose limiting organ at risk (OAR), optionally wherein the OAR is a serial OAR.

15. The method of claim 14, wherein the $PTV_{HD}$ comprises at least 60% of the total $PTV_{TOTAL}$ or wherein the $PTV_{HD}$ comprises at least 60% of the tumor's total volume.

16. The method of claim 14, wherein the $PTV_{PMDS}$ comprises 40% or less of the $PTV_{TOTAL}$ or wherein the $PTV_{PMDS}$ comprises at least 5% of the $PTV_{TOTAL}$.

17. The method of claim 14, wherein the dose of radiation delivered to 95% of the $PTV_{HD}$ is at least 18 Gy, at least 19 Gy, at least 20 Gy, at least 21 Gy, at least 22 Gy, at least 23 Gy, at least 24 Gy, at least 25 Gy, at least 26 Gy, or between about 22 Gy and about 25 Gy, or wherein the dose of radiation delivered to 95% of the $PTV_{PMDS}$ is less than about 23 Gy, less than about 18 Gy, less than about 12 Gy, between about 12 Gy and 23 Gy or between about 12 Gy and 18 Gy; or wherein the dose of radiation delivered to 95% of the $PTV_{PMDS}$ is at least 10% lower than the dose of radiation delivered to 95% of the $PTV_{HD}$ or is between about 10% and about 50% lower than the dose of radiation delivered to 95% of the $PTV_{HD}$, or is at least 50% lower than the dose of radiation delivered to 95% of the $PTV_{HD}$; or wherein the dose of radiation delivered to 95% of the $PTV_{PMDS}$ is at least 10% lower than the dose of radiation delivered to 95% of the $PTV_{TOTAL}$ required to treat the tumor, is between about 10% and about 50% lower than the dose of radiation delivered to 95% of the $PTV_{TOTAL}$ required to treat the tumor, or is at least 50% lower than the dose of radiation delivered to 95% of the $PTV_{TOTAL}$ required to treat the tumor; or wherein the doses of radiation are delivered to the $PTV_{HD}$ and the $PTV_{PMDS}$ in the same treatment session or are delivered to the $PTV_{HD}$ and the $PTV_{PMDS}$ simultaneously in the same treatment session.

18. The method of claim 14, wherein sending the signal from the processor to the radiation source includes sending the signal via a network, or wherein the processor is included in an electronic device having at least the processor and a memory and wherein the electronic device and the radiation source are included in a single machine.

19. The method of claim 14, further comprising:

capturing one or more images of the tumor via an imaging device; and sending, from the imaging device and to the processor, data associated with the one or more images;

wherein the processor is configured to define the $PTV_{TOTAL}$ based at least in part on the data associated with the one or more images of the tumor, optionally wherein the imaging device and the radiation source are included in the same machine; or wherein the processor is included in an electronic device having at least the processor and a memory, and wherein the electronic device and the imaging device are included in a single machine; or the imaging device is in communication with the electronic device via a network.

20. A method of defining a perfusion modulated dose sculpting (PMDS) radiotherapy plan for treating a tumor in a subject in need thereof, the method comprising:

defining, at a processor, a total planning target volume ($PTV_{TOTAL}$) of the tumor;

dividing, at the processor, the $PTV_{TOTAL}$ of the tumor into at least a first planning target sub-volume ($PTV_{HD}$) and a second planning target sub-volume ($PTV_{PMDS}$), wherein the $PTV_{PMDS}$ comprises at least 5% of the tumor's total volume;

defining a dose of radiation for each of the $PTV_{HD}$ and the $PTV_{PMDS}$; and defining the PMDS radiotherapy plan for treating the tumor wherein the dose of radiation covering 95% of the $PTV_{PMDS}$ is lower than the dose of radiation covering 95% of the $PTV_{HD}$ and wherein the dose of radiation covering 95% of the $PTV_{PMDS}$ is lower than the dose of radiation covering 95% of the total PTV required to treat the tumor.

* * * * *